US008609830B2

(12) United States Patent
Jackson et al.

(10) Patent No.: US 8,609,830 B2
(45) Date of Patent: Dec. 17, 2013

(54) METHODS AND COMPOSITIONS FOR RNA INTERFERENCE

(75) Inventors: Aimee L. Jackson, Seattle, WA (US); Steven R. Bartz, Seattle, WA (US); Julja Burchard, Mount Vernon, WA (US); Janell M. Schelter, Bellevue, WA (US); Peter S. Linsley, Seattle, WA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1503 days.

(21) Appl. No.: 10/557,219

(22) PCT Filed: May 17, 2004

(86) PCT No.: PCT/US2004/015439
§ 371 (c)(1),
(2), (4) Date: Jan. 26, 2007

(87) PCT Pub. No.: WO2005/018534
PCT Pub. Date: Mar. 3, 2005

(65) Prior Publication Data
US 2007/0149468 A1    Jun. 28, 2007

Related U.S. Application Data

(60) Provisional application No. 60/471,392, filed on May 16, 2003, provisional application No. 60/515,223, filed on Oct. 27, 2003.

(51) Int. Cl.
*C07H 21/00* (2006.01)
(52) U.S. Cl.
USPC ......... 536/24.5; 536/24.31; 536/24.1; 702/19
(58) Field of Classification Search
None
See application file for complete search history.

(56) References Cited

U.S. PATENT DOCUMENTS

| | | | |
|---|---|---|---|
| 5,510,270 A | 4/1996 | Fodor | |
| 5,539,083 A | 7/1996 | Cook | |
| 5,545,522 A | 8/1996 | Van Gelder | |
| 5,556,752 A | 9/1996 | Lockhart | |
| 5,569,588 A | 10/1996 | Ashby | |
| 5,578,832 A | 11/1996 | Trulson | |
| 5,716,785 A | 2/1998 | Van Gelder | |
| 5,891,636 A | 4/1999 | Van Gelder | |
| 6,028,189 A | 2/2000 | Blanchard | |
| 6,040,138 A | 3/2000 | Lockhart | |
| 6,132,997 A | 10/2000 | Shannon | |
| 6,203,987 B1 | 3/2001 | Friend | |
| 6,218,122 B1 | 4/2001 | Friend | |
| 6,271,002 B1 | 8/2001 | Linsley | |
| 6,351,712 B1 | 2/2002 | Stoughton | |
| 6,506,559 B1 | 1/2003 | Fire | |
| 6,801,859 B1 | 10/2004 | Friend | |
| 7,013,221 B1 | 3/2006 | Friend | |
| 2002/0016216 A1 | 2/2002 | Kobayashi | |
| 2002/0086356 A1 | 7/2002 | Tuschl | |
| 2002/0182590 A1 | 12/2002 | Strange | |
| 2003/0226098 A1 | 12/2003 | Wang | |
| 2004/0143399 A1 | 7/2004 | Wang | |
| 2004/0248299 A1* | 12/2004 | Jayasena et al. ............ 435/455 |
| 2004/0259247 A1* | 12/2004 | Tuschl et al. ............... 435/375 |

FOREIGN PATENT DOCUMENTS

| | | |
|---|---|---|
| EP | 0 534858 A1 | 3/1993 |
| WO | WO 98/38329 | 9/1998 |
| WO | WO 98/41531 | 9/1998 |
| WO | WO 99/58708 | 11/1999 |
| WO | WO 99/59037 | 11/1999 |
| WO | WO 99/66067 | 12/1999 |
| WO | WO 00/24936 | 5/2000 |
| WO | WO 00/39336 | 7/2000 |
| WO | WO 02/16650 | 2/2002 |
| WO | WO 02/18464 | 3/2002 |
| WO | WO 02/44321 * | 6/2002 |
| WO | WO 02/44399 | 6/2002 |
| WO | WO 03/006477 | 1/2003 |
| WO | WO 2005/042708 | 5/2005 |

OTHER PUBLICATIONS

Scherer et al. Approaches for the Sequence-specific knockdown of mRNA (Nat. Biotechnol., 2003, 21(12), pp. 1457-1465).*
Mahato et al. Modulation of gene expression by antisense and antigene oligodeoxynucleotides and small interfering RNA. Expert Opin. Deliv. 2005, vol. 2(1): 3-28.*
Lin et al. siRNA mediated off-target gene silencing triggered by a 7 nt complementation. Nucleic Acids Research vol. 33, 2005: 4527-4535.*
Saxena et al. Small RNAs with imperfect match to endogenous mRNA repress translation. JBC 2003: 44312-44319.*
Snove et al. Many commonly used siRNAs risk off-target activity. Biochemical and Biophysical Research Communications 2-4: 256-263.*
U.S. Appl. No. 09/364,751, filed Jul. 30, 1999, Friend.
U.S. Appl. No. 60/227,966, filed Aug. 25, 2000, Shoemaker et al.
U.S. Appl. No. 60/515,180, filed Oct. 27, 2003, Jackson et al.

(Continued)

*Primary Examiner* — Kimberly Chong
(74) *Attorney, Agent, or Firm* — Christensen O'Connor Johnson Kindness PLLC

(57) ABSTRACT

The invention provides methods and compositions for gene silencing by RNA interference. In particular, the invention provides methods for gene silencing or RNA knockdown using small interfering RNAs (siRNAs) having partial sequence homology to its target gene. The invention also provides methods for identifying common and/or differential responses to a plurality of different siRNAs targeting a gene. The invention also provides methods for evaluating the relative activity of the two strands of an siRNA. The invention further provides methods of designing siRNAs for gene silencing. The invention further provides methods of using siRNAs as therapeutics for treatment of diseases.

41 Claims, 21 Drawing Sheets

(56) References Cited

OTHER PUBLICATIONS

Blanchard et al., 1996, "High-density oligonucleotide arrays," Biosensors & Bioelectronics vol. 11: 687-690.
Blanchard et al., 1996, "Sequence to array: Probing the genome's secrets," Nature Biotechnology vol. 14: 1649.
Blanchard, "Synthetic DNA Arrays," Rosetta Reference Library # 230: 1-16.
Brummelkamp et al., 2002, "A System for Stable Expression of Short Interfering RNAs in Mammalian Cells," Science vol. 296: pp. 550-552.
Chirgwin et al., 1979, "Isolation of biologically active ribonucleic acid from sources enriched in ribonuclease," Biochemistry 18:5294-5299.
"Small RNAs Make Big Splash," 2002, Breakthrough Online—Science vol. 298: 2296-2297.
de Wildt et al., 2000, "Antibody arrays for high-throughput screening of antibody-antigen interactions," Nature Biotechnology vol. 18: 989-994.
DeRisi et al., 1996, "Use of a cDNA microarray to analyse gene expression patterns in human cancer," Nature Genetics 14:457-460.
Duggan et al., 1999, "Expression profiling using cDNA microarrays," Nature Genetics Supplement vol. 21: 10-14.
Egholm et al., 1993, "PNA hybridizes to complementary oligonucleotides obeying the Watson-Crick hydrogen-bonding rules," Nature 365:566-568.
Elbashir et al., 2001, "RNA interference is mediated by 21- and 22-nucleotide RNAs," Genes & Development 15: 188-200.
Elbashir et al., 2001, "Duplexes of 21—nucleotide RNAs mediate RNA interference in cultured mammalian cells," Nature vol. 411: 494-498.
Elbashir et al., 2001, "Functional anatomy of siRNAs for mediating efficient RNAi in *Drosophila melanogaster* embryo lysate," The EMBO Journal vol. 20: 6877-6888.
Elbashir et al., 2002, "Analysis of gene function in somatic mammalian cells using small interfering RNAs," Methods 26: 199-213.
Ferguson et al., 1996, "A fiber-optic DNA biosensor microarray for the analysis of gene expression," Nature Biotechnology 14:1681-1684.
Fodor et al., 1991, "Light-directed, spatially addressable parallel chemical synthesis," Science 251:767-773.
Froehler et al., 1986, "Synthesis of DNA via deoxynucleoside H-phosphonate intermediates," Nucleic Acids Research 14:5399-5407.
Goffeau et al., 1996, "Life with 6000 genes," Science 274:546-567.
Grishok et al., 2001, "Genes and Mechanisms Related to RNA Interference Regulate Expression of the Small Temporal RNAs that Control *C. elegans* Developmental Timing," Cell, vol. 106: 23-34.
Gygi et al., 1999, "Quantitative analysis of complex protein mixtures using isotope-coded affinity tags," Nature Biotechnology vol. 17: 994-999.
Hammond et al., 2001, "Argonaute2, a Link Between Genetic and Biochemical Analyses of RNAi," Science vol. 293: 1146-1150.
Hannon, 2002, "RNA interference," Nature vol. 418: 244-251.
Holen ct al., 2002, "Positional effects of short interfering RNAs targeting the human coagulation trigger Tissue Factor," Nucleic Acids Research, vol. 30 No. 8: 1757-1766.
Hughes et al., 2001, "Expression profiling using microarrays fabricated by an ink-jet oligonucleotide synthesizer," Nature Biotechnology vol. 19: 342-347.
Hutvágner et al., 2001, "A Cellular Function for the RNA-Interference Enzyme Dicer in the Maturation of the let-7 Small Temporal RNA," Science, vol. 293: 834-838.
Hutvágner et al., 2002, "A microRNA in a Multiple-Turnover RNAi Enzyme Complex," Science vol. 297: 2056-2060.
Ketting et al., 2001, "Dicer functions in RNA interference and in synthesis of small RNA involved in development timing in *C. elegans*," Genes & Development 15: 2654-2659.
Lander, 1996, "The new genomics: Global views of biology," Science 274:536-539.

Lau et al., 2001, "An Abundant Class of Tiny RNAs with Probable Regulatory Roles in *Caenorhabditis elegans*," Science 294: 858-862.
Lee et al., 1993, "The *C. elegans* Heterochronic Gene lin-4 Encodes Small RNAs with Antisense Complementarity to lin-14," Cell, vol. 75:843-854.
Lee et al., 2001, "An Extensive Class of Small RNAs in *Caenorhabditis elegans*," Science 294: 862-864.
Lewis et al., 2002, "Efficient delivery of siRNA for inhibition of gene expression in postnatal mice," Nature Genetics 32: 107-108.
Lockhart et al., 1996, "Expression monitoring by hybridization to high-density oligonucleotide arrays," Nature Biotechnology 14:1675-1680.
MacBeath et al., 2000, "Printing Proteins as Microarrays for High-Throughput Function Determination," Science 289: 1760-1763.
Maskos et al., 1992, "Oligonucleotide hybridisations on glass supports: a novel linker for oligonucleotide synthesis and hybridisation properties of oligonucleotides synthesised in situ," Nucleic Acids Research 20: 1679-1684.
McBride et al., 1983, "An Investigation of Several Deoxynucleoside Phosphoramidites Useful for Sythesizing Deoxyoligonucleotides," Tetrahedron Letters 24: 245-248.
McCaffrey et al., 2002, "RNA interference in adult mice," Nature 418: 38-39.
McGall et al., 1996, "Light-directed synthesis of high-density oligonucleotide arrays using semiconductor photoresists," Proc. Natl. Acad. Sci. USA 93: 13555-13560.
McManus et al., 2002, "Gene silencing in mammals by small interfering RNAs," Nature Review—Genetics 3: 737-747.
Mourelatos et al., 2002, "miRNPs: a novel class of ribonucleoproteins containing numerous microRNAs," Genes & Development 16: 720-728.
Nguyen et al., 1995, "Differential gene expression in the murine thymus assayed by quantitative hybridization of arrayed cDNA clones," Genomics 29:207-216.
Paddison et al., 2002, "RNA interference: the new somatic cell genetics," Cancel Cell 2: 17-23.
Paddison et al., 2002, "Short hairpin RNAs (shRNAs) induce sequence-specific silencing in mammalian cells," Genes & Development 16: 948-958.
Pease et al., 1994, "Light-generated oligonucleotide arrays for rapid DNA sequence analysis," Proc. Natl. Acad. Sci. 91: 5022-5026.
Prashar et al., 1996, "Analysis of differential gene expression by display of 3' end restriction fragments of cDNAs," Proc. Natl. Acad. Sci. USA 93:659-663.
Reinhart et al., 2000, "The 21-nucleotide let-7 RNA regulates developmental timing in *Caenorhabditis elgans*," Nature 403: 901-906.
Reinhart et al., 2002, "Small RNAs Correspond to Centromere Heterochromatic Repeats," Science 297: 1831.
Rubinson et al., 2003, "A lentivirus-based system to functionally silence genes in primary mammalian cells, stem cells and transgenic mice by RNA interference," Nature Genetics 33: 401-406.
Sagliocco et al., 1996, "Identification of Proteins of the Yeast Protein Map using Genetically Manipulated Strains and Peptide-Mass Fingerprinting," Yeast 12: 1519-1533.
Schena et al., 1995, "Quantitative Monitoring of Gene Expression Patterns with a Complementary DNA Microarray," Science 270: 467-470.
Schena et al., 1996, "Parallel human genome analysis; microarray-based expression of 1000 genes," Proc. Natl. Acad. Sci. USA 93:10614-10619.
Shalon et al., 1996, "A DNA microarray system for analyzing complex DNA samples using two-color fluorescent probe hybridization," Genome Research 6:639-645.
Shevchenko et al., 1996, "Linking genome and proteome by mass spectrometry: Large-scale identification of yeast proteins from two dimensional gels," Proc. Natl. Acad. Sci. 93: 14440-14445.
Song et al., 2003, "RNA interference targeting Fas protects mice from fulminant hepatitis," Nature Medicine 9: 347-351.
Sørensen et al., 2003, "Gene Silencing by Systemic Delivery of Synthetic siRNAs in Adult Mice," J. Mol. Biol. 327: 761-766.
Sui et al., 2002, "A DNA vector-based RNAi technology to suppress gene expression in mammalian cells," PNAS 99: 5515-5520.

(56) References Cited

OTHER PUBLICATIONS

Tiscornia et al., 2003, "A general method for gene knockdown in mice by using lentiviral vectors expressing small interfering RNA," PNAS 100: 1844-1848.
Tuschl et al., 1999, "Targeted mRNA degradation by double-stranded RNA in vitro," Genes & Development 13: 3191-3197.
Velculescu et al., 1995, "Serial Analysis of Gene Expression," Science 270: 484-487.
Volpe et al., 2002, "Regulation of Heterochromatic Silencing and Histone H3 Lysine-9 Methylation by RNAi," Science 297: 1833-1837.
Ward et al, 1963, "A Hierarchical Grouping Procedure Applied to a Problem of Grouping Profiles," American Statistical Association Journal: 236-244.
Wightman et al., 1993, "Posttranscriptional Regulation of the Heterochronic Gene lin-14 by lin-4 Mediates Temporal Pattern Formation in *C. elegans*," Cell 75: 855-862.
Williams et al., 2002, "ARGONAUTE1 is required for efficient RNA interference in *Drosophila* embroyos," PNAS 99: 6889-6894.
Xia et al., 2002, "siRNA-mediated gene silencing in vitro and in vivo," Nature Biotechnology 20: 1006-1010.
Zeng et al., 2002, "Both Natural and Designed Micro RNAs Can Inhibit the Expression of Cognate mRNAs When Expressed in Human Cells," Molecular Cell 9: 1327-1333.
Zhu et al., 2001, "Global Analysis of Protein Activities Using Proteome Chips," Science 293: 2101-2105.
Green, D. W. et al., 2000, "Antisense Oligonucleotides: An evolving technology for the modulation of gene expression in human disease," J. Am. Coll. Surg. vol. 191, 93-105.
Jen, K. Y. et al., 2000, "Suppression of gene expression by targeted disruption of messenger RNA: available options and current strategies," Stem Cells vol. 18, 307-318.
Caplen, N. J. et al., 2003, "RNAi as a gene therapy approach," Gene Therapy vol. 3, No. 4, 575-586.
Paroo, Z. et al., 2004, "Challenges for RNAi in vivo," Trends in Biotechnology vol. 22, 309-394.
Novina, C. D. et al., 2004, "The RNAi revolution," Nature vol. 430, 161-164.
International Search Report for International Application No. PCT/US04/15439.
Written Opinion of the International Search Authority for International Application No. PCT/US04/15439.
Chi, J.-T., "Genomewide View of Gene Silencing by Small Interfering RNAs," PNAS 100(11):6343-6346, May 2003.
Semizarov, D., "Specificity of Short Interfering RNA Determined Through Gene Expression Signatures," PNAS 100(11):6347-6352, May 2003.
Amarzguioui, M., et al., "Tolerance for Mutations and Chemical Modifications in a siRNA," Nucleic Acids Research 31(2):589-595, Jan. 2003.
Bartz, S.R., et al, "Off-Target Activity of siRNA Oligos in Mammalian Cells," Molecular Cell Biology 13 (Suppl.):409A-410A, Proceedings of the 42nd Annual Meeting of the American Society for Cell Biology, San Francisco, Dec. 14-18, 2002.
Burchard, J., et al., "MicroRNA-Like Off-Target Transcript Regulation by siRNAs is Species Specific," RNA 15(2):308-315, Feb. 2009.
Hamada, M., et al., "Effects on RNA Interference in Gene Expression (RNAi) in Cultured Mammalian Cells of Mismatches and the Introduction of Chemical Modifications at the 3'-Ends of siRNAs," Antisense and Nucleic Acid Drug Development 12(5):301-309, Oct. 2002.
Harborth, J., et al., "Sequence, Chemical, and Structural Variation of Small Interfering RNAs and Short Hairpin RNAs and the Effect on Mammalian Gene Silencing," Antisense and Nucleic Acid Drug Development 13(2):83-105, Apr. 2003.
Jackson, A.L., et al., "Expression Profiling Reveals Off-Target Gene Regulation by RNAi," Nature Biotechnology 21(6):635-637, Jun. 2003.
Jackson, A.L., and P.S. Linsley, "Noise Amidst the Silence: Off-Target Effects of siRNAs?" TRENDS in Genetics 20(11):521-524, Nov. 2004.
Jackson, A.L., et al., "Widespread siRNA 'Off-Target' Transcript Silencing Mediated by Seed Region Sequence Complementarity," RNA 12(7):1179-1187, Jul. 2006.
Leirdal, M., and M. Sioud, "Gene Silencing in Mammalian Cells by Preformed Small RNA Duplexes," Biochemical and Biophysical Research Communications 295(1):744-748, Jun. 2002.
Supplementary European Search Report mailed Mar. 8, 2010, issued in corresponding European Application No. 04776024.4, filed May 17, 2004.

\* cited by examiner

| Accession | Gene name | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| NM_001315 (SEQ ID NO:29) | MAPK14 | C | C | T | A | C | A | G | A | G | A | A | C | T | G | C | G | G | T | T |
| NM_002271 (SEQ ID NO:30) | KPNB3 | G | C | T | A | C | A | G | A | G | A | A | C | T | G | C | A | T | C | C |
| Hs13_10109_29_13_1603 | RAP2A (SEQ ID NO 31) | T | C | T | A | C | A | G | A | G | A | A | C | T | G | C | A | G | C | C |
| NM_017748 (SEQ ID NO:32) | FLJ20291 | T | T | T | A | C | A | G | A | G | A | A | C | T | T | C | G | G | T | A |
| A133672 (SEQ ID NO:33) | Contig53709_RC | C | C | T | C | A | A | A | G | A | A | C | C | T | G | C | G | G | T | T |
| NM_004165 (SEQ ID NO:34) | RRAD | A | G | G | C | C | C | T | C | A | G | A | C | T | G | C | G | G | G | T |
| NM_002946 (SEQ ID NO:35) | RPA2 | G | A | A | G | C | A | G | G | G | A | A | C | T | T | T | G | G | T | G |
| NM_018457 (SEQ ID NO:36) | DKFZp564J157 | A | T | G | A | G | C | T | T | T | G | A | C | T | G | C | G | G | T | T |
| NM_013242 (SEQ ID NO:37) | AF093680 | A | A | T | A | T | T | T | C | T | T | C | C | T | G | C | G | G | T | T |
| AW237459 (SEQ ID NO:38) | Contig56528_RC | A | G | G | A | G | A | A | T | G | A | A | C | T | G | C | G | G | T | A |

FIG. 4A

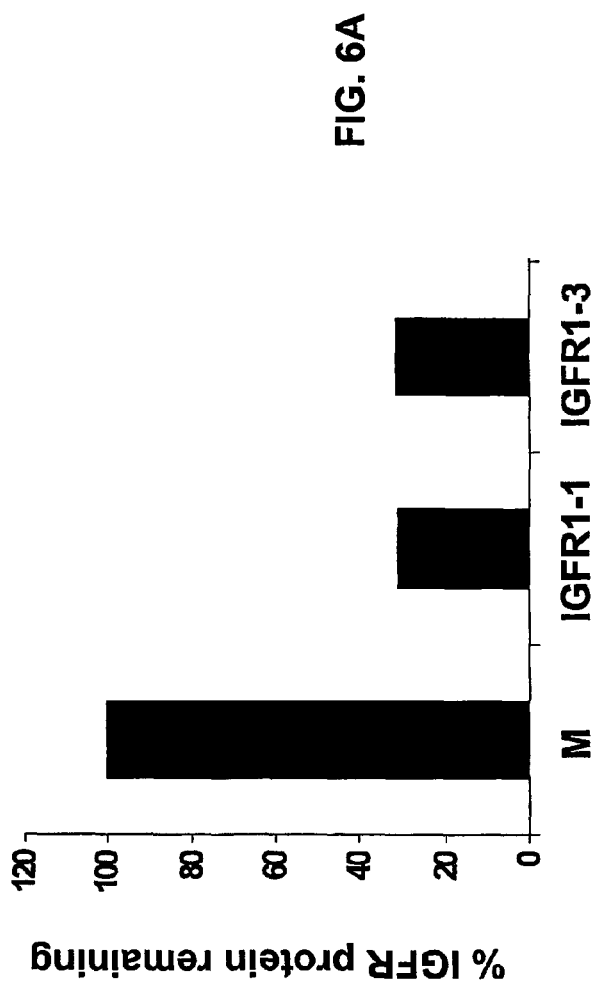
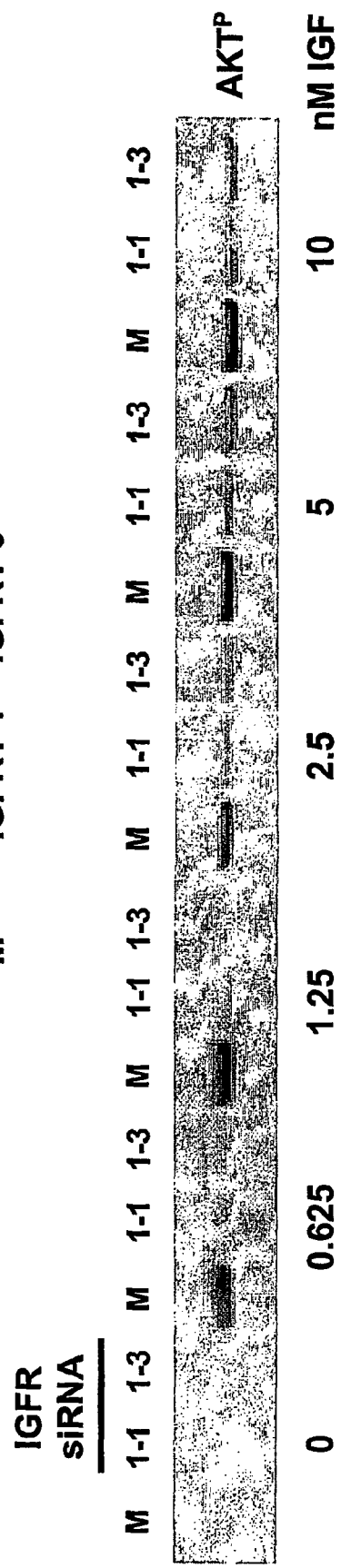
FIG. 6A
FIG. 6B

METHODS AND COMPOSITIONS FOR RNA INTERFERENCE

This application claims the benefit under 35 U.S.C. §119 (e) of U.S. Provisional Patent Application No. 60/515,223, filed on Oct. 27, 2003, and U.S. Provisional Patent Application No. 60/471,392, filed on May 16, 2003, each of which is incorporated by reference herein in its entirety.

1. FIELD OF THE INVENTION

The present invention relates to methods and compositions for gene silencing using RNA interference. The invention also relates to methods for identifying common and/or differential responses to a plurality of small interfering RNAs designed to silence a gene. The invention further relates to methods of designing small interfering RNAs for gene silencing. The invention further relates to methods of using siRNA as therapeutics.

2. BACKGROUND OF THE INVENTION

RNA interference (RNAi) is a potent method to suppress gene expression in mammalian cells, and has generated much excitement in the scientific community (Couzin, 2002, Science 298:2296-2297; McManus et al., 2002, Nat. Rev. Genet. 3, 737-747; Hannon, G. J., 2002, Nature 418, 244-251; Paddison et al., 2002, Cancer Cell 2, 17-23). RNA interference is conserved throughout evolution, from C. elegans to humans, and is believed to function in protecting cells from invasion by RNA viruses. When a cell is infected by a dsRNA virus, the dsRNA is recognized and targeted for cleavage by an RNaseIII-type enzyme termed Dicer. The Dicer enzyme "dices" the RNA into short duplexes of 21nt, termed siRNAs or short-interfering RNAs, composed of 19 nt of perfectly paired ribonucleotides with two unpaired nucleotides on the 3' end of each strand. These short duplexes associate with a multiprotein complex termed RISC, and direct this complex to mRNA transcripts with sequence similarity to the siRNA. As a result, nucleases present in the RISC complex cleave the mRNA transcript, thereby abolishing expression of the gene product. In the case of viral infection, this mechanism would result in destruction of viral transcripts, thus preventing viral synthesis. Since the siRNAs are double-stranded, either strand has the potential to associate with RISC and direct silencing of transcripts with sequence similarity.

Specific gene silencing promises the potential to harness human genome data to elucidate gene function, identify drug targets, and develop more specific therapeutics. Many of these applications assume a high degree of specificity of siRNAs for their intended targets. Cross-hybridization with transcripts containing partial identity to the siRNA sequence may elicit phenotypes reflecting silencing of unintended transcripts in addition to the target gene. This could confound the identification of the gene implicated in the phenotype. Numerous reports in the literature purport the exquisite specificity of siRNAs, suggesting a requirement for near-perfect identity with the siRNA sequence (Elbashir et al., 2001. EMBO J. 20:6877-6888; Tuschl et al., 1999, Genes Dev. 13:3191-3197; Hutvagner et al., Sciencexpress 297:2056-2060). One recent report predicts that perfect sequence complementarity is required for siRNA-targeted transcript cleavage, while partial complementarity will lead to tranlational repression without transcript degradation, in the manner of microRNAs (Hutvagner et al., Sciencexpress 297: 2056-2060). However, most of the published analyses of siRNA-induced gene silencing have examined only one or a few genes in addition to the targeted gene, an approach not unlike "looking for keys under the lampost."

The biological function of small regulatory RNAS, including siRNAs and miRNAs is not well understood. One prevailing question regards the mechanism by which the distinct silencing pathways of these two classes of regulatory RNA are determined. miRNAs are regulatory RNAs expressed from the genome, and are processed from precursor stem-loop structures to produce single-stranded nucleic acids that bind to sequences in the 3'UTR of the target mRNA (Lee et al., 1993, Cell 75:843-854; Reinhart et al., 2000, Nature 403:901-906; Lee et al., 2001, Science 294:862-864; Lau et al., 2001, Science 294:858-862; Hutvagner et al., 2001, Science 293:834-838). miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

It has also been shown that siRNA and shRNA can be used to silence genes in vivo. The ability to utilize siRNA and shRNA for gene silencing in vivo has the potential to enable selection and development of siRNAs for therapeutic use. A recent report highlights the potential therapeutic application of siRNAs. Fas-mediated apoptosis is implicated in a broad spectrum of liver diseases, where lives could be saved by inhibiting apoptotic death of hepatocytes. Song (Song et al. 2003, Nat. Medicine 9, 347-351) injected mice intravenously with siRNA targeted to the Fas receptor. The Fas gene was silenced in mouse hepatocytes at the mRNA and protein levels, prevented apoptosis, and protected the mice from hepatitis-induced liver damage. Thus, silencing Fas expression holds therapeutic promise to prevent liver injury by protecting hepatocytes from cytotoxicity. As another example, injected mice intraperitoneally with siRNA targeting TNF-a. Lipopolysaccharide-induced TNF-a gene expression was inhibited, and these mice were protected from sepsis. Collectively, these results suggest that siRNAs can function in vivo, and may hold potential as therapeutic drugs (Sorensen et al., 2003, J. Mol. Biol. 327, 761-766).

U.S. Pat. No. 6,506,559 discloses a RNA interference process for inhibiting expression of a target gene in a cell. The process comprises introducing partially or fully doubled-stranded RNA having a sequence in the duplex region that is identical to a sequence in the target gene into the cell or into the extracellular environment. RNA sequences with insertions, deletions, and single point mutations relative to the target sequence are also found as effective for expression inhibition.

U.S. Patent Application Publication No. US 2002/0086356 discloses RNA interference in a *Drosophila* in vitro system using RNA segments 21-23 nucleotides (nt) in length. The patent application publication teaches that when these 21-23 nt fragments are purified and added back to *Drosophila* extracts, they mediate sequence-specific RNA interference in the absence of long dsRNA. The patent application publication also teaches that chemically synthesized oligonucleotides of the same or similar nature can also be used to target specific mRNAs for degradation in mammalian cells.

PCT publication WO 02/44321 discloses that double-stranded RNA (dsRNA) 19-23 nt in length induces sequence-specific post-transcriptional gene silencing in a *Drosophila* in vitro system. The PCT publication teaches that short interfering RNAs (siRNAs) generated by an RNase III-like processing reaction from long dsRNA or chemically synthesized siRNA duplexes with overhanging 3' ends mediate efficient target RNA cleavage in the lysate, and the cleavage site is located near the center of the region spanned by the guiding siRNA. The PCT publication also provides evidence that the direction of dsRNA processing determines whether sense or antisense target RNA can be cleaved by the produced siRNP complex.

U.S. Patent Application Publication No. US 2002/016216 discloses a method for attenuating expression of a target gene in cultured cells by introducing double stranded RNA (dsRNA) that comprises a nucleotide sequence that hybridizes under stringent conditions to a nucleotide sequence of the target gene into the cells in an amount sufficient to attenuate expression of the target gene.

PCT publication WO 03/006477 discloses engineered RNA precursors that when expressed in a cell are processed by the cell to produce targeted small interfering RNAs (siRNAs) that selectively silence targeted genes (by cleaning specific mRNAs) using the cell's own RNA interference (RNAi) pathway. The PCT publication teaches that by introducing nucleic acid molecules that encode these engineered RNA precursors into cells in vivo with appropriate regulatory sequences, expression of the engineered RNA precursors can be selectively controlled both temporally and spatially, i.e., at particular times and/or in particular tissues, organs, or cells.

DNA array technologies have made it possible to monitor the expression level of a large number of genetic transcripts at any one time (see, e.g., Schena et al., 1995, *Science* 270:467-470; Lockhart et al., 1996, *Nature Biotechnology* 14:1675-1680; Blanchard et al., 1996, *Nature Biotechnology* 14:1649; Ashby et al., U.S. Pat. No. 5,569,588, issued Oct. 29, 1996). Of the two main formats of DNA arrays, spotted cDNA arrays are prepared by depositing PCR products of cDNA fragments with sizes ranging from about 0.6 to 2.4 kb, from full length cDNAs, ESTs, etc., onto a suitable surface (see, e.g., DeRisi et al., 1996, *Nature Genetics* 14:457-460; Shalon et al., 1996, *Genome Res.* 6:689-645; Schena et al., 1995, *Proc. Natl. Acad. Sci. U.S.A.* 93:10539-11286; and Duggan et al., *Nature Genetics* Supplement 21:10-14). Alternatively, high-density oligonucleotide arrays containing thousands of oligonucleotides complementary to defined sequences, at defined locations on a surface are synthesized in situ on the surface by, for example, photolithographic techniques (see, e.g., Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; McGall et al., 1996, *Proc. Natl. Acad. Sci. U.S.A.* 93:13555-13560; U.S. Pat. Nos. 5,578,832; 5,556,752; 5,510,270; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123). Efforts to further increase the information capacity of DNA arrays range from further reducing feature size on DNA arrays so as to further increase the number of probes in a given surface area to sensitivity- and specificity-based probe design and selection aimed at reducing the number of redundant probes needed for the detection of each target nucleic acid thereby increasing the number of target nucleic acids monitored without increasing probe density (see, e.g., Friend et al., U.S. patent application Ser. No. 09/364,751, filed on Jul. 30, 1999; and Friend et al., U.S. patent application Ser. No. 09/561,487, filed on Apr. 28, 2000).

By simultaneously monitoring tens of thousands of genes, DNA array technologies have allowed, inter alia, genome-wide analysis of mRNA expression in a cell or a cell type or any biological sample. Aided by sophisticated data management and analysis methodologies, the transcriptional state of a cell or cell type as well as changes of the transcriptional state in response to external perturbations, including but not limited to drug perturbations, can be characterized on the mRNA level (see, e.g., Stoughton et al., International Publication No. WO 00/39336, published Jul. 6, 2000; Friend et al., International Publication No. WO 00/24936, published May 4, 2000; and Shoemaker et al., International Publication No. WO 02/16650, published Feb. 28, 2002). Applications of such technologies include, for example, identification of genes which are up regulated or down regulated in various physiological states, particularly diseased states. Additional exemplary uses for DNA arrays include the analyses of members of signaling pathways, and the identification of targets for various drugs. See, e.g., Friend and Hartwell, International Publication No. WO 98/38329 (published Sep. 3, 1998); Stoughton, International Publication No. WO 99/66067 (published Dec. 23, 1999); Stoughton and Friend, International Publication No. WO 99/58708 (published Nov. 18, 1999); Friend and Stoughton, International Publication No. WO 99/59037 (published Nov. 18, 1999); Friend et al., U.S. patent application Ser. No. 09/334,328 (filed on Jun. 16, 1999).

Discussion or citation of a reference herein shall not be construed as an admission that such reference is prior art to the present invention.

3. SUMMARY OF THE INVENTION

The invention provides a method of silencing a target gene in an eukaryotic cell by RNA interference, comprising subjecting said cell to molecules of a small interfering RNA (siRNA), wherein said siRNA comprises a sense strand or antisense strand contiguous nucleotide sequence of at least 11 nucleotides that is identical to a sequence of a transcript of said target gene but wherein said siRNA does not have full length sense strand or antisense strand sequence identity to any sequences in said transcript, said contiguous nucleotide sequence being in the central region of said siRNA. In one embodiment of the invention, the siRNA does not comprise a sense strand or antisense strand contiguous nucleotide sequence of greater than 16, 15, 14, 13, 12, or 11 nucleotides in length that is identical to said sequence of said transcript of said target gene.

The invention also provides a method of silencing a target gene in an eukaryotic cell by RNA interference, comprising subjecting said cell to molecules of a small interfering RNA (siRNA), wherein said siRNA comprises a sense strand or antisense strand contiguous nucleotide sequence of at least 9 nucleotides that is identical to a sequence of a transcript of said target gene but wherein said siRNA does not have full length sense strand or antisense strand sequence identity to any sequences in said transcript, said contiguous nucleotide sequence being at the 3' end of said siRNA. In one embodiment of the invention, the siRNA does not comprise a sense strand or antisense strand contiguous nucleotide sequence of greater than 16, 15, 14, 13, 12, 11, 10, or 9 nucleotides in length that is identical to said sequence of said transcript of said target gene.

The invention also provides a method of silencing a plurality of different genes in an eukaryotic cell by RNA interference, wherein the sequence of a transcript of each of said plurality of different genes comprises a nucleotide sequence of 9-18 nucleotides which is common among said plurality of different genes, said method comprising subjecting said cell to molecules of a small interfering RNA (siRNA), wherein said siRNA comprises (i) a sense strand or antisense strand central contiguous nucleotide sequence of at least 11 nucleotides that is identical to a sequence in said common sequence, and/or (ii) a 3' sense strand or antisense strand contiguous nucleotide sequence of at least 9 nucleotides that is identical to a sequence in said common sequence. In one embodiment, the central contiguous nucleotide sequence is 11-15, 14-15, 13, 12, or 11 nucleotides in length.

The invention also provides a method of silencing a first gene but not a second gene in an eukaryotic cell by RNA interference, comprising subjecting said eukaryotic cell to an siRNA molecule that comprises (i) a sense strand or antisense strand central contiguous nucleotide sequence of at least 11 nucleotides that is identical to a sequence of a transcript of said first gene, or (ii) a 3' sense strand or antisense strand contiguous nucleotide sequence of at least 9 nucleotides that is identical to a sequence of a transcript of said first gene; which siRNA does not comprise any sense strand or antisense strand central contiguous nucleotide sequences of more than 10 nucleotides that are identical to a sequence of said transcript of said second gene and which siRNA does not comprise any 3' sense strand or antisense strand contiguous nucleotide sequences of more than 8 nucleotides that are identical to a sequence of said transcript of said second gene. In one embodiment, the siRNA molecule does not comprise contiguous nucleotide sequences of more than 8 nucleotides in length that are identical to any sequence of said transcript of said second gene. In another embodiment, the central contiguous nucleotide sequence in (i) is 11-15, 14-15, 13, 12, or 11 nucleotides in length. In another embodiment, the contiguous nucleotide sequence in (ii) is 9-15, 9-12, 10, or 9 nucleotides in length.

The invention also provides a method of designing a small interfering RNA for silencing a first gene but not a second gene in an eukaryotic cell by RNA interference, comprising identifying an siRNA molecule that comprises (i) a sense strand or antisense strand central contiguous nucleotide sequence of at least 11 nucleotides that is identical to a sequence of a transcript of said first gene, or (ii) a 3' sense strand or antisense strand contiguous nucleotide sequence of at least 9 nucleotides that is identical to a sequence of said transcript of said first gene; which siRNA does not comprise any sense strand or antisense strand central contiguous nucleotide sequences of more than 10 nucleotides that are identical to a sequence of a transcript of said second gene and which siRNA does not comprise any 3' sense strand or antisense strand contiguous nucleotide sequences of more than 8 nucleotides that are identical to a sequence of said transcript of said second gene. In one embodiment, the siRNA molecule does not comprise contiguous nucleotide sequences of more than 8 nucleotides in length that are identical to any sequence of said transcript of said second gene. In another embodiment, the central contiguous nucleotide sequence in (i) is 11-15, 14-15, 13, 12, or 11 nucleotides in length. In another embodiment, the contiguous nucleotide sequence in (ii) is 9-15, 9-12, 10, or 9 nucleotides in length.

The invention also provides a method of selecting one or more small interfering RNA (siRNA) from a plurality of different siRNAs for silencing a gene in an eukaryotic cell, each said different siRNA being designed to target a different sequence in a transcript of said gene, comprising (a) determining for each said siRNA a response profile, said response profile comprising measurements of expression levels of a plurality of genes; and (b) selecting one or more siRNAs based on their response profiles. In one embodiment, the plurality of different siRNAs comprises siRNAs whose sequences tile across a part of or the entire coding sequence of said target gene. In another embodiment the plurality of different siRNAs comprises siRNAs whose sequences tile across a part of or the entire coding sequence of said target gene at an interval of 10 bases. In still another embodiment, the plurality of different siRNAs comprises siRNAs whose sequences tile across a part of or the entire coding sequence of said target gene at an interval of 5 bases. In still another embodiment, the plurality of different siRNAs comprises siRNAs whose sequences tile across a part of or the entire coding sequence of said target gene at an interval of 1 base. In some embodiment, the one or more siRNAs are selected by a method comprising comparing said response profile of each said siRNA with a desired response profile and selecting one or more siRNAs whose response profile matches said desired response profile.

The invention also provides a method for designing a small interfering RNA (siRNA) for targeting a plurality of different genes in an eukaryotic cell, wherein said plurality of different genes share a common nucleotide sequence of 9-18 nucleotides, comprising selecting an siRNA which comprises (i) a sense strand or antisense strand central contiguous nucleotide sequence of at least 11 nucleotides that is identical to a sequence in said common sequence, and/or (ii) a 3' sense strand or antisense strand contiguous nucleotide sequence of 9 nucleotides that is identical to a sequence in said common sequence. In one embodiment, the central contiguous nucleotide sequence is 11-15, 14-15, 13, 12, or 11 nucleotides in length.

The invention also provides a method of determining an effect of an siRNA on an eukaryotic cell, comprising determining an expression profile of said eukaryotic cell at a chosen time point after subjecting said cell to said siRNA, wherein each said expression profile comprises measured transcript levels of a plurality of different genes. In the method of the invention, the plurality of different genes can comprise 5, 10, 100, 1,000, 10,000, or 25,000 different genes.

The invention also provides a method of determining an effect of an siRNA on an eukaryotic cell, comprising (a) determining an expression profile of said eukaryotic cell at each of a plurality of different times after subjecting said eukaryotic cell to said siRNA, wherein each said expression profile comprises measured transcript levels of a plurality of different genes; and (b) grouping said plurality of genes into different kinetic groups based on the kinetic behavior of said measured transcript levels. In the method of the invention, the plurality of different genes can comprise 5, 10, 100, 1,000, 10,000, or 25,000 different genes.

The invention also provides a method of identifying one or more genes in an eukaryotic cell silenced by an small interfering RNA (siRNA), wherein said siRNA is designed to silence a target gene in said eukaryotic cell, said method comprising (a) determining an expression profile of said eukaryotic cell at each of a plurality of different times after subjecting said eukaryotic cell to said siRNA, wherein each said expression profile comprises measured transcript levels of a plurality of different genes; and (b) identifying one or more genes among said plurality of different genes, the transcript levels of which decrease substantially faster than the decrease of the level of a protein encoded by said target gene. In one embodiment, said transcript levels of said one or more genes decrease at least 50% before the level of said protein encoded by said target gene decreases to about 50% of its unperturbed level. In another embodiment, said decrease of the level of said protein is determined by a method comprising measuring the abundance of said protein at each of said plurality of different times. In the method of the invention, the plurality of different genes can comprise 5, 10, 100, 1,000, 10,000, or 25,000 different genes.

The invention also provides a method of identifying one or more genes in an eukaryotic cell which are silenced directly by a plurality of different small interfering RNA molecules (siRNA), wherein each said siRNA is designed to silence a same target gene in said eukaryotic cell, said method comprising (a) determining an expression profile of said eukaryotic cell for each of said plurality of different siRNAs, wherein each said expression profile comprises measured transcript levels of a plurality of different genes; and (b) identifying one or more genes among said plurality of genes, the transcript levels of which are commonly affected by said plurality of siRNAs. In one embodiment, the step (b) is carried out by a method comprising clustering said plurality of genes among expression profiles of different siRNAs. In another embodiment, each said expression profile is determined at a same time after introduction of each said siRNA. In another embodiment, said time point is substantially shorter than the time scale of a 50% decrease of the level of a protein encoded by said target gene from its unperturbed level. In the method of the invention, the plurality of different genes can comprise 5, 10, 100, 1,000, 10,000, or 25,000 different genes.

The invention further provides a method of identifying one or more candidate genes in an eukaryotic cell, wherein alteration of expression level of said one or more candidate genes may result in a phenotypic feature in said eukaryotic cell, said method comprising (a) identifying a phenotypic feature of said eukaryotic cell which is associated with introduction of a small interfering RNA (siRNA) into said eukaryotic cell, wherein said siRNA is designed to silence a target gene in said eukaryotic cell; (b) determining an expression profile of said eukaryotic cell at each of a plurality of different times after introduction of said siRNA, wherein each said expression profile comprises measured transcript levels of a plurality of different genes; (c) identifying one or more genes among said plurality of genes, the transcript levels of which decrease substantially faster than the decrease of the level of a protein encoded by said target gene; and (d) identifying said one or more genes as said one or more candidate genes. In one embodiment, said transcript levels of said one or more genes decrease at least 50% before the level of said protein encoded by said target gene decreases to about 50% of its unperturbed level. In another embodiment, said decrease of the level of said protein is determined by a method comprising measuring the abundance of said protein at each of said plurality of different times. In the method of the invention, the plurality of different genes can comprise 5, 10, 100, 1,000, 10,000, or 25,000 different genes.

The invention also provides a method of identifying one or more candidate genes in an eukaryotic cell, wherein alteration of expression levels of said one or more candidate genes may result in a phenotypic feature in said eukaryotic cell, said method comprising (a) identifying a phenotypic feature of said eukaryotic cell commonly associated with introduction of each of a plurality of different small interfering RNA molecules (siRNA), wherein each said siRNA is designed to silence a same target gene in said eukaryotic cell; (b) determining an expression profile of said eukaryotic cell for each of a plurality of different small interfering RNA molecules (siRNA), wherein each said siRNA is designed to silence a same target gene in said eukaryotic cell, and wherein each said expression profile comprises measured transcript levels of a plurality of different genes; (c) identifying one or more genes among said plurality of genes, the transcript levels of which are commonly affected by said plurality of siRNAs; and (d) identifying said one or more genes as said one or more candidate genes. In one embodiment, the step (c) is carried out by a method comprising clustering said plurality of genes among expression profiles of different siRNAs. In another embodiment, each said expression profile is determined at a same time after introduction of each said siRNA. In another embodiment, said time point is substantially shorter than the time scale of a 50% decrease of the level of a protein encoded by said target gene from its unperturbed level. In the method of the invention, the plurality of different genes can comprise 5, 10, 100, 1,000, 10,000, or 25,000 different genes.

The invention further provides a method of identifying one or more genes that are regulated by a first protein but not by a second protein in an eukaryotic cell, comprising (a) subjecting said eukaryotic cell to molecules of an siRNA that comprises (i) a sense strand or antisense strand central contiguous nucleotide sequence of at least 11 nucleotides that is identical to a sequence of a transcript of a first gene encoding said first protein, or (ii) a 3' sense strand or antisense strand contiguous nucleotide sequence of at least 9 nucleotides that is identical to a sequence of said transcript of said first gene; which siRNA does not comprise any sense strand or antisense strand central contiguous nucleotide sequences of more than 10 nucleotides that are identical to a sequence of a transcript of a second gene encoding said second protein and which siRNA does not comprise any 3' sense strand or antisense strand contiguous nucleotide sequences of more than 8 nucleotides that are identical to a sequence of said transcript of said second gene; (b) determining an expression profile of said eukaryotic cell after a period of time after subjecting said eukaryotic cell to said siRNA, wherein each said expression profile comprises measured transcript levels of a plurality of different genes, and wherein said period of time is longer than the time at which a 50% decrease of the level of said first protein in said cell is observed relative to the level of said first protein in said cell not subjected to said siRNA; and (c) identifying one or more genes, transcript levels of which are altered from their levels in cells not subjected to said siRNA as genes that are silenced by said first protein but not said second protein. In one embodiment, the siRNA molecule does not comprise contiguous nucleotide sequences of more than 8 nucleotides in length that are identical to any sequence of said transcript of said second gene. In another embodiment, the central contiguous nucleotide sequence in (i) is 11-15, 14-15, 13, 12, or 11 nucleotides in length. In another embodiment, the contiguous nucleotide sequence in (ii) is 9-15, 9-12, 10, or 9 nucleotides in length. In the method of the invention, the plurality of different genes can comprise 5, 10, 100, 1,000, 10,000, or 25,000 different genes.

The invention further provides an eukaryotic cell comprising a small interfering RNA (siRNA), wherein said siRNA comprises a sense strand or antisense strand contiguous nucleotide sequence of at least 11 nucleotides that is identical to a sequence of a transcript of a gene in said eukaryotic cell but does not have full length sense strand or antisense strand sequence identity to any sequences in a transcript of any other genes in the genome of said eukaryotic cell, said contiguous nucleotide sequence being in the central region of said siRNA molecules. In one embodiment of the invention, the siRNA does not comprise a sense strand or antisense strand contiguous nucleotide sequence of greater than 16, 15, 14, 13, 12, or 11 nucleotides in length that is identical to said sequence of said transcript of said target gene. The invention also provides an eukaryotic cell comprising a small interfering RNA (siRNA), wherein said siRNA comprises a sense strand or antisense strand contiguous nucleotide sequence of at least 11 nucleotides that is identical to a sequence of a transcript of a gene in said eukaryotic cell but does not have full length sense strand or antisense strand sequence identity to any sequences in a transcript of any other genes in the genome of said eukaryotic cell, said contiguous nucleotide sequence being at the 3' end of said siRNA molecules. In one embodiment of the invention, the siRNA does not comprise a sense strand or antisense strand contiguous nucleotide sequence of greater than 16, 15, 14, 13, 12, 11, 10, or 9 nucleotides in length that is identical to said sequence of said transcript of said target gene. The eukaryotic cell can be a human cell.

The invention also provides a method of identifying genes that are differentially silenced by a first siRNA and a second siRNA both designed to silence a target gene in an eukaryotic cell, comprising (a) comparing a first expression profile of said eukaryotic cell and a second expression profile of said eukaryotic cell, wherein said first expression profile is measured at a chosen time point after introduction of said first siRNA into said cell and said second expression profile is measured at said chosen time point after introduction of said second siRNA into said cell, and wherein each said expression profile comprises measured transcript levels of a plurality of different genes; and (b) identifying genes other than said target gene whose transcript levels are differentially affected by said first and second siRNA. In one embodiment, said chosen time point is substantially shorter than the time scale of a 50% decrease of the level of a protein encoded by said target gene from its unperturbed level, and wherein said genes identified are directly differentially silenced by said first and second siRNA. In another embodiment, said chosen time point is substantially longer than the time scale of a 50% decrease of the level of a protein encoded by said target gene from its unperturbed level a protein encoded by said target gene, and wherein said genes identified are differentially silenced by said first and second siRNA as a result of differential silencing of directly silenced genes. In the method of the invention, the plurality of different genes can comprise 5, 10, 100, 1,000, 10,000, or 25,000 different genes.

In any one of the methods of the invention, the eukaryotic cell can be a human cell.

The invention further provides a method of treating a disease or undesirable condition in an mammal, comprising administering to said mammal a therapeutically sufficient amount of an siRNA, wherein said siNRA target a gene whose expression causes said disease or undesirable condition, wherein said siRNA comprises (i) a sense strand or antisense strand central contiguous nucleotide sequence of at least 11 nucleotides but not more than 18 that is identical to a sequence in a transcript of said gene, and/or (ii) a 3' sense strand or antisense strand contiguous nucleotide sequence of at least 9 but not more than 18 nucleotides that is identical to a sequence in said transcript. In one embodiment of the invention, the siRNA does not comprise a sense strand or antisense strand contiguous nucleotide sequence of greater than 16, 15, 14, 13, 12, or 11 nucleotides in length that is identical to said sequence of said transcript of said target gene. In one embodiment, the mammal is a human.

In another aspect, the invention provides a method of silencing a target gene in an eukaryotic cell by RNA interference. The method comprises introducing into the eukaryotic cell a plurality of different siRNAs designed to silence the target gene. In preferred embodiments, the plurality of different siRNAs consists of at least 3, 5, 9, 12, 15, 20, 50 or 100 different siRNAs. In a preferred embodiment, the total concentration of the plurality of siRNAs is an optimal concentration for silencing the target gene. Such an optimal concentration can be a concentration further increase of which does not increase the level of silencing substantially. For example, the optimal concentration can be a concentration further increase of which does not increase the level of silencing of said target gene by more than 5%, 10% or 20%. In a preferred embodiment, the composition of the plurality, including the number of different siRNAs in the plurality and the concentration of each different siRNA, is chosen such that the plurality of siRNAs causes less than 30%, 20%, 10% or 5%, 1%, 0.1% or 0.01% of silencing of any off-target genes. In another preferred embodiment, the plurality of different siRNAs comprises each siRNA in equal proportion. In still another preferred embodiment, the plurality of different siRNAs comprises each siRNA in proportions different from each other by less than 5%, 10%, 20% or 50%. In still another preferred embodiment, none of the plurality of different siRNAs constitutes more than 90%, 80%, 70%, 50%, or 20% of the total siRNA concentration in the plurality. In some other embodiments, each siRNA in the plurality has an concentration that is lower than the concentration of the siRNA that is effective to achieve at least 30%, 50%, 75%, 80% 85%, 90% or 95% silencing when used in the absence of other siRNAs or in the absence of other siRNAs designed to silence the target gene. In one embodiment, each siRNA has a concentration that causes less than 30%, 20%, 10% or 5% of silencing of the target gene when used in the absence of other siRNAs or in the absence of other siRNAs designed to silence the target gene.

In another aspect, the invention provides a method of evaluating relative gene silencing activity of the first and second strands of an siRNA, comprising comparing the sequence similarity of the first strand and the sequence similarity of the second strand to a transcript sequence of each of one or more genes. Preferably, the one or more genes comprise 2, 5, 10, 100, or 1,000 different genes. In one embodiment, the one or more genes consist of genes directly silenced by the siRNA. In one embodiment, the genes directly silenced by the siRNA are genes that are down-regulated by the siRNA with the same kinetics. In one embodiment, the one or more genes comprise both genes directly silenced by the siRNA and genes indirectly silenced by the siRNA. In another embodiment, the one or more genes consist of genes whose transcript levels are decreased by the siRNA as detected at a given time point after introduction of the siRNA into cells. The given time point can be about 12 hours or 24 hours after introduction of the siRNA into cells.

In one embodiment, the comparing is carried out by a method comprising (a) determining for each of the one or more genes the length of the longest contiguous stretch of sequence identity in an alignment of the first strand of the siRNA with the transcript sequence of the gene; (b) determining for each of the one or more genes the length of the longest contiguous stretch of sequence identity in an alignment of the second strand of the siRNA with the transcript sequence of the gene; and (c) comparing a total first strand identity length to a total second strand identity length, wherein the total first strand identity length is obtained by summing the length determined in step (a) for the one or more genes, and wherein the total second strand identity length is obtained by summing the length determined in step (b) for the one or more genes.

In another embodiment, the sequence similarity of the first strand to the transcript sequence of the gene is represented by (i) the length of the longest contiguous stretch of sequence identity in the alignment of the first strand with the transcript sequence of the gene, and the sequence similarity of the second strand to the transcript sequence of the gene is represented by (ii) the length of the longest contiguous stretch of sequence identity in the alignment of the second strand with the transcript sequence of the gene. Preferably, the comparing comprises determining a difference between (i) and (ii) for the gene. In one embodiment, the difference is the number of nucleotides in the longer of (i) and (ii) in excess of that in the shorter of (i) and (ii), and wherein the comparing sequence similarity is carried out by a method comprising (a) determining the total number of nucleotides in the first strand in excess of the second strand among the one or more genes; (b) determining the total number of nucleotides in the second strand in excess of the second strand among the one or more genes; and (c) identifying the siRNA as having higher second strand silencing activity relative to first strand gene silencing activity if the total number of nucleotides determined in step (a) is greater than the total number of nucleotides determined in step (b), or as having higher first strand silencing activity relative to second strand silencing activity if the total number of nucleotides determined in step (b) is greater than the total number of nucleotides determined in step (a). In one embodiment, the comparing in step (c) is carried out by calculating a SLR score according to the equation $$SLR = \log(\text{the total number of nucleotides in the first strand in excess of the second strand among the one or more genes/the total number of nucleotides in the second strand in excess of the first strand among the one or more genes}).$$

In another embodiment, the total number of nucleotides in the first and the second strand may be corrected by the background excess nucleotide numbers.

In still another embodiment, the comparing is carried out by a method comprising (a) identifying each gene in the one or more genes that has a contiguous stretch of sequence of at least 7 bases that is identical to a sequence of the first strand of the siRNA and that is terminated within 3 bases of the 3' end of the first strand of the siRNA; (b) identifying each gene in the one or more genes that has a contiguous stretch of sequence of at least 7 bases that is identical to a sequence of the second strand of the siRNA and that is terminated within 3 bases of the 3' end of the second strand of the siRNA; and (c) comparing the number of genes identified in step (a) with the number of genes identified in step (b), wherein the siRNA is determined to have higher second strand silencing activity relative to first strand silencing activity if the number of genes identified in step (a) is greater than the number of genes identified in step (b), or to have higher first strand silencing activity relative to second strand silencing activity if the number of genes identified in step (b) is greater than the number of genes identified in step (a). In one embodiment, the comparing in step (c) is carried out by calculating a SLR score according to the equation $$SLR = \log(\text{number of first strand identical genes/number of second strand identical genes})$$

wherein the number of first strand identical genes is the number of genes identified in step (a), and the number of second strand identical genes is the number of genes identified in step (b).

4. BRIEF DESCRIPTION OF FIGURES

FIGS. 1A-B illustrate gene expression patterns specific for the siRNA sequence revealed by expression profiling. FIG. 1A: Eight different siRNA duplexes target to the MAPK14 coding region were utilized for gene silencing in HeLa cells. Luc, siRNA targets to luciferase. FIG. 1B: Sixteen different siRNA duplexes target to the IGF1R coding region were utilized for gene silencing. Cells were transfected in 6-well plates using Oligofectamine (Invitrogen) and 100 nM siRNA duplex per well. siRNAs were obtained from Dharmacon (Boulder, Colo.) as annealed and purified duplexes. RNA from siRNA-transfected cells was hybridized against RNA from mock-transfected cells (treated with transfection reagent in the absence of RNA duplex). Total RNA was purified by Qiagen RNeasy kit, and processed for hybridization to microarrays containing oligonucleotides corresponding to approximately 21,000 human genes. Microarrays were either purchased from Agilent Technologies or synthesized. Each row represents the expression pattern resulting from transfection of an individual siRNA. Data shown are genes that display at least a two-fold change in expression level (p value<0.01 and $\log_{10}$ intensity>1) relative to mock-transfected cells. Light gray indicates decreased expression, Black indicates increased expression. Data were analyzed using Rosetta Resolver™ software. The bar graph represents the fraction of target protein (gray bars) and RNA (black bars) remaining after siRNA transfection. RNA quantification was performed by Real-time PCR, using AP Biosystems TaqMan pre-developed assay reagent (#4319442) for IGF1R. Primer probe for MAPK14 was custom designed using Primer Express software. RNA values for IGF1R and MAPK14 were normalized to RNA for actin (#4326315). IGF1R protein was quantified by flow cytometry following staining with IGF1R-specific monoclonal antibody (BD Biosciences #555998) and phycoerythrin-conjugated secondary antibody (BD Biosciences #550589). Asterisks indicate the IGF1R siRNA duplexes that reduced protein level by at least 60%. MAPK 14 protein was quantified by western blot of cell lysates with Mapk14-specific monoclonal antibody (BD Biosciences) followed by Kodak image analysis of chemiluminescent immunoblot. MAPK 14 protein levels were normalized to actin levels. Error bars represent standard deviation of at least three independent experiments.

FIG. 2 illustrates dosage effect of siRNA on off-target gene silencing. Off-target gene silencing was not eliminated by decreased siRNA concentration. HeLa cells were transfected with the indicated concentrations of MAPK14-1 siRNA. RNA was extracted 48 hours post-transfection and was analyzed as described in FIG. 1.

FIGS. 3A-C show kinetic analysis of Mapk14 protein and RNA knockdown by RNAi. FIG. 3A Protein extracts were harvested at the indicated times following transfection of HeLa cells with siRNA MAPK14-1 and subjected to immunoblot analysis of MAPK 14 protein. FIG. 3B RNA extracts were harvested at the indicated times following transfection of HeLa cells and processed for expression profiling as described in FIG. 1. RNA from siRNA-transfected cells was hybridized against RNA from mock-transfected cells at the same time point. Expression patterns were determined by clustering with a set of genes regulated in common by 5 of 8 siRNAs to MAPK14. Each row represents the gene expression pattern at a single time point. The data are a compilation of two independent experiments, a short time course of 1-to-24 hours, and a longer time course of 24-to-96 hours. Thus, there are two independent data sets for the 24-hour time point, demonstrating the experimental reproducibility. Bar graph represents the fraction of MAPK14 RNA remaining after siRNA transfection, as quantitated by real-time PCR. FIG. 3C Transcript data from the microarray analysis in (b) were analyzed by trend plot. Shown is a selection of regulated transcripts (p value<0.1 at three of nine time points, $\log_{10}$ ratio>0.3 at 2 of 9 timepoints, and $\log_{10}$ intensity>−1 at 2 of 9 timepoints). Several genes that displayed incoherent expression patterns between different time points were removed from the analysis (NMP200, HIRA, HKE2, EYA4, FLJ20281, LMNB1, EGR1). Remaining transcripts were divided into six temporal groups based on timing of half-maximal transcript degradation. Data are presented as $\log_{10}$ of expression ratio plotted as a function of time after transfection. Group 1: MAPK14; Group 2: KPNB3, RAP2A, FLJ20291, RRAD, RPA2, DKFZp564J157, AF093680, and two uncharacterized EST contigs (see FIG. 4A). Group 3: MGC4809, NCF2, IFI44, Contig41538_RC, CBFA2T3, ISG15, LGP2, SCYA5. Group 4: H2AFL. Group 5: KIAA1460. Group 6: VCP, TIMP4, AL162069, BIRC3, CTGF.

FIGS. 4A-C illustrate contribution of sequence similarity to off-target gene regulation. FIG. 4A: sequence alignment of genes regulated with similar kinetics to MAPK14. Nucleotides with perfect identity to the MAPK14 sequence are indicated in bold, mismatched nucleotides are indicated in small font. The degree of sequence identity to the MAPK14 transcript is indicated as the number of contiguous identical nucleotides/the total number of identical nucleotides. FIG. 4B: cluster analysis of gene silencing for transcripts in kinetic group 2. HeLa cells were transfected with homologous MAPK14 siRNA, or siRNA containing a single nucleotide substitution to diminish the degree of sequence similarity. RNA extracts were harvested 48 hours after transfection. Each row represents the effect of the single nucleotide substitution on the pattern of gene expression for transcripts silenced with rapid kinetics. Green represents decreased gene expression, black represents lack of differential regulation (see Table 1 for siRNA sequences). FIG. 4C: Gene expression resulting from silencing of the off-target genes KPNB3 and FLJ20291. HeLa cells were transfected with siRNA sequences corresponding to the off-target genes KPNB3 (upper panel) and FLJ20291 (lower panel). Microarray data are plotted as $\log_{10}$ of expression ratio versus $\log_{10}$ of fluorescence intensity. The targeted genes, as well as MAPK14, are indicated.

FIG. 5 MAPK14 and IGF1R silencing produce distinct gene expression patterns. The transcript expression data for eight MAPK14 siRNAs and sixteen IGF1R siRNAs were combined into a single experiment group. Statistical requirements included pvalue<0.01 and $\log_{10}$ expression ratio=0.3 for at least seven siRNAs. Dotted line separates IGF1R expression profiles from MAPK14 expression profiles.

FIGS. 6A-C show that IGF1R siRNA interferes with receptor expression and function. FIG. 6A Protein extracts were harvested 96 hours following transfection of MCF7 cells with IGF1R siRNAs. IGF1R protein was quanfied by flow cytometry as described in FIG. 1. FIG. 6B Seventy-two hours following transfection of MCF7 cells with IGF1R siRNAs, cells were serum-starved for 24 hours, and subsequently stimulated with the indicated doses of IGF for 2 hours. Protein extracts were subjected to immunoblot analysis of phosphorylated AKT using antibody specific for the phosphorylated form of this protein (Cell Signaling). FIG. 6C RNA from mock-transfected or siRNA-transfected cells that were serum starved and stimulated with IGF was hybridized against similarly-transfected and starved cells that were not stimulated with IGF.

Figure 10:
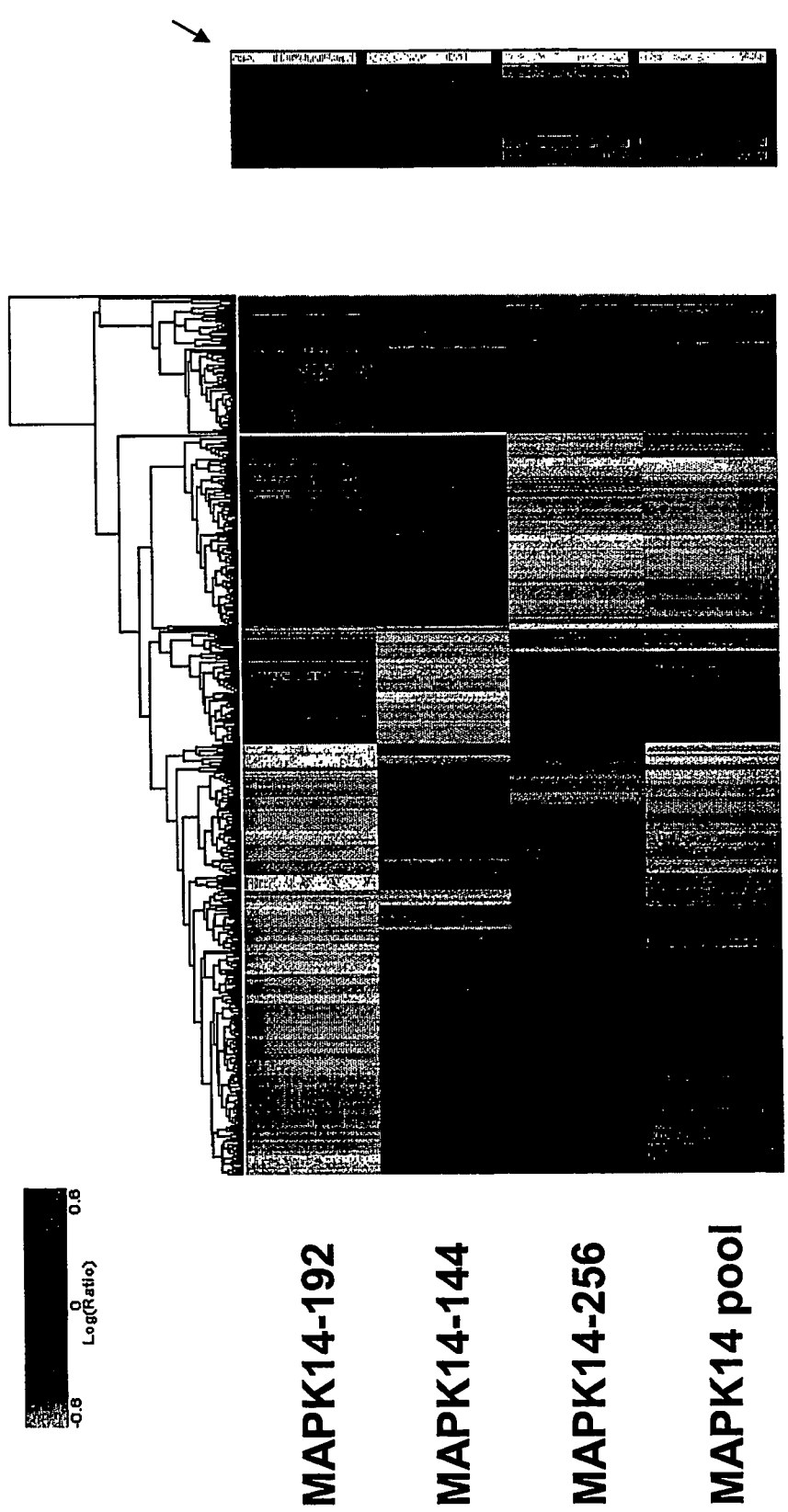

FIG. 10 shows results with using an siRNA pool of 3 siRNAs. Each individual siRNA was transfected into HeLa cells at a concentration of 33 nM. The pool of the 3 siRNAs was transfected at 100 nM (33 nM each individual.) RNA was extracted 24 hours post-transfection and profiled against RNA from mock-transfected cells. The panel on the right indicates that on-target gene silencing is maintained in the pool. The number of off-target events is approximately the sum of the off-target events from each individual siRNA, but the magnitude of off-target silencing is reduced.

Figure 11:
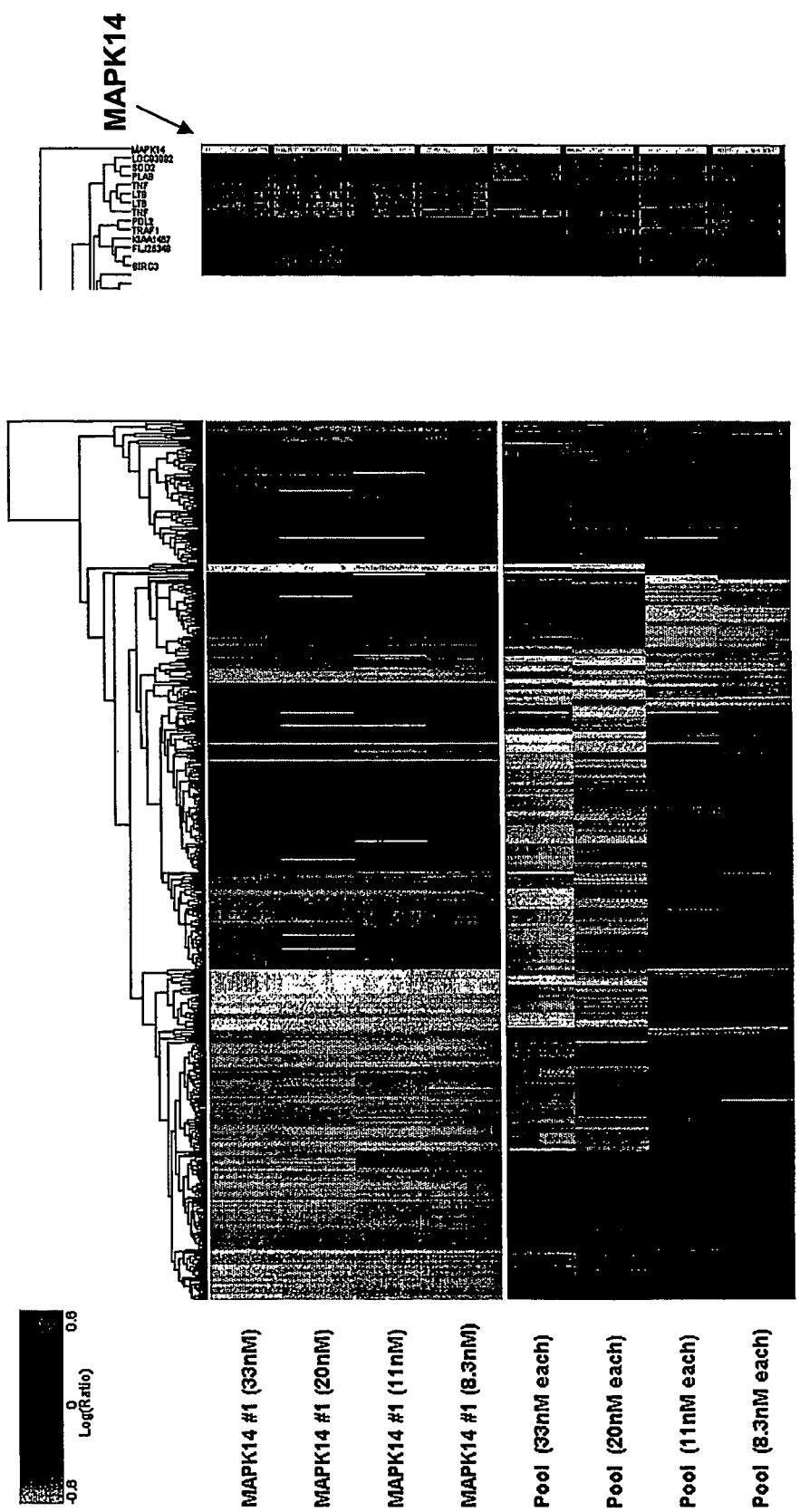
Figure 12:

FIG. 11 shows that siRNA pool increased silencing specificity. Decreasing the concentration of a single siRNA does not improve specificity (upper panel.) In contrast, increasing pool size, maintains on-target silencing while reducing the number and magnitude of off-target gene silencing. This may be due to competition among the siRNAs for association with RISC. As a result, the ratio of on-target:off-target gene silencing is increased, leading to increased specificity. This suggests that increasing to even larger pool sizes would lead to further increases in specificity, which would be of enormous benefit for target validation efforts FIG. 12 shows results using an siRNA pool of 9 siRNAs. The concentration of each individual siRNA was at 11 nM, and the pool contained 9 members each at 11 nM. With increased number of siRNAs in an siRNA pool, the number of signature genes in the pool was decreased, perhaps due to competition among the siRNAs for association with RISC. As a result, the magnitude of off-target silencing was reduced, and the ratio of on-target:off-target gene silencing was increased, leading to increased specificity.

Figure 13B:
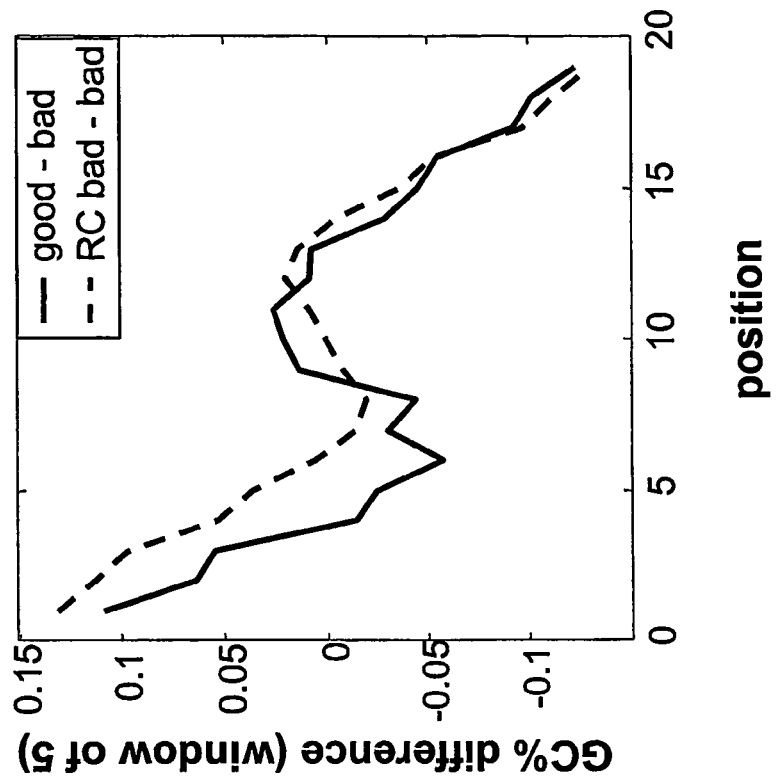
Figure 13A:
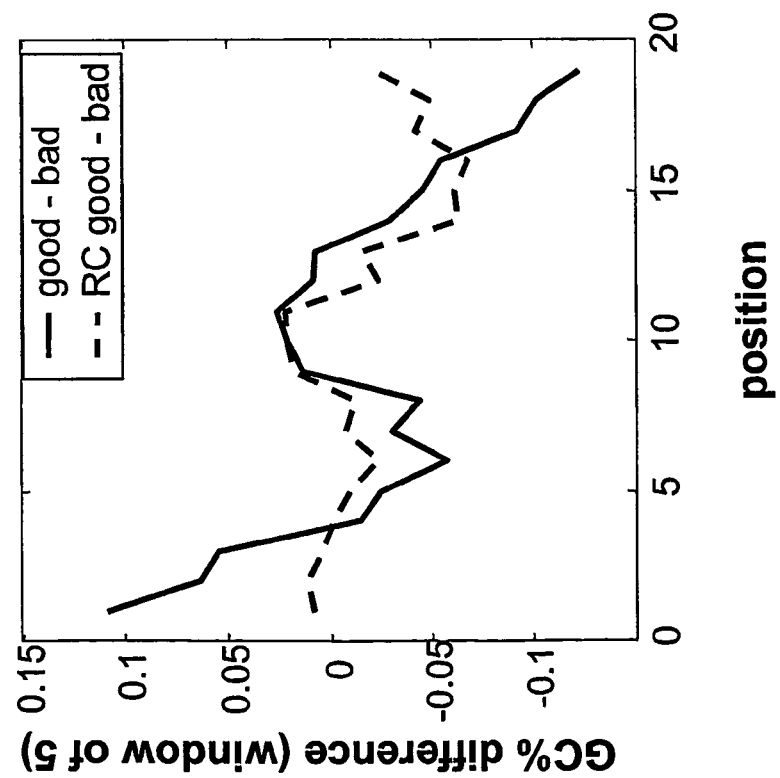

FIGS. 13A-B show comparison of the GC content of siRNAs and their reverse complements with the GC content of bad siRNAs. The comparison implies that bad siRNAs have sense strands similar to good siRNAs, while good siRNAs have sense strands similar to bad siRNAs. RC: reverse complement of the siRNA target sequence.

Figure 14:
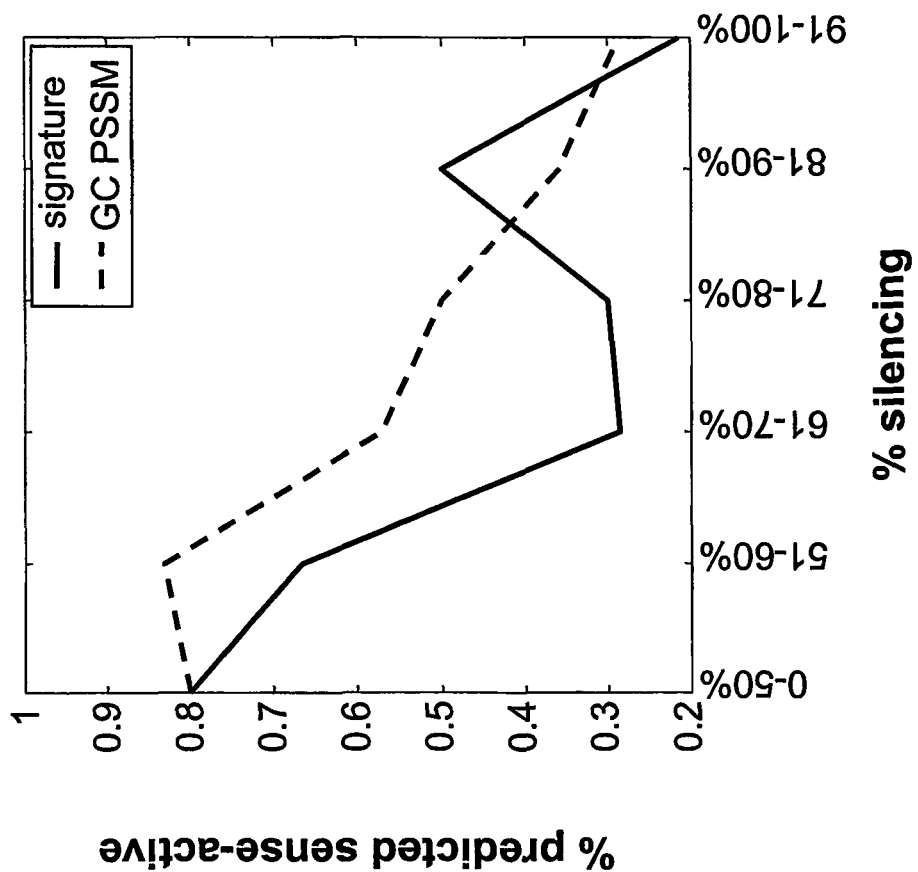

FIG. 14 shows that less effective siRNAs have active sense strands. Strand bias of 61 siRNAs was predicted from expression profiles by the 3'-biased method, and from comparison of the GC PSSM scores of the siRNAs and their reverse complements. Strand bias predictions were binned by siRNA silencing efficacy.

Figure 15:
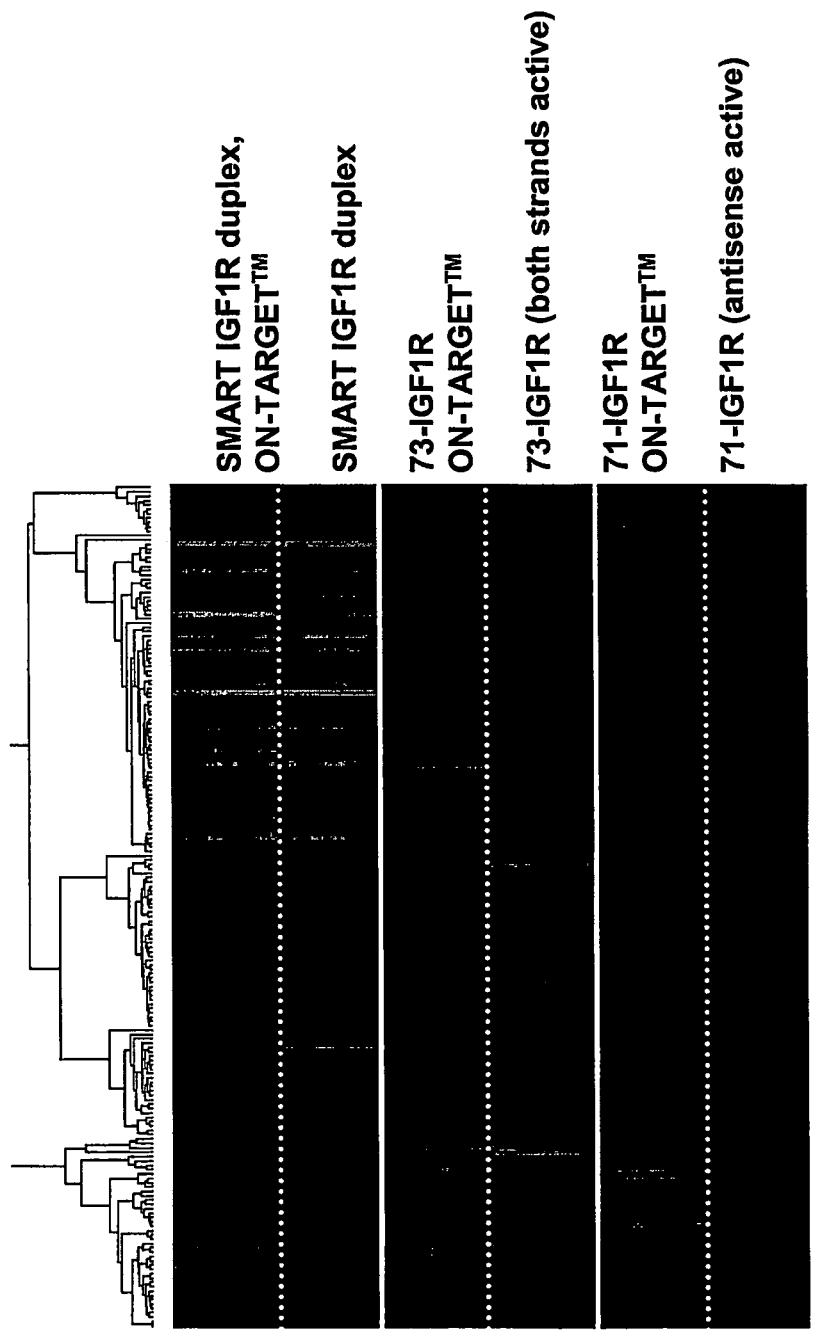

FIG. 15 shows that sense strand modification alters specificity of "sense-active" siRNA. siRNAs transfected into HeLa cells at a concentration of 100 nM. RNA was extracted 12 hours post-transfection and profiled against RNA from mock-transfected cells. On-target siRNAs contain two 2-o-methyl substitutions in the sense strand to inactivate that strand and prevent it from functioning in gene silencing. The signature of siRNA 71, previously determined to be antisense-active, was not changed by the sense strand inactivation. In contrast, the signature of the siRNA 73, in which both strands were active, was significantly altered by sense-strand inactivation. In this situation, the sense strand was prevented from functioning in gene silencing, and potentially prevented from interacting with RISC, thus enabling the antisense strand to become dominant. This result indicates that chemical inactivation of the sense strand can alter the off-target signature of sense-active siRNAs, but does not eliminate it.

Figure 16:
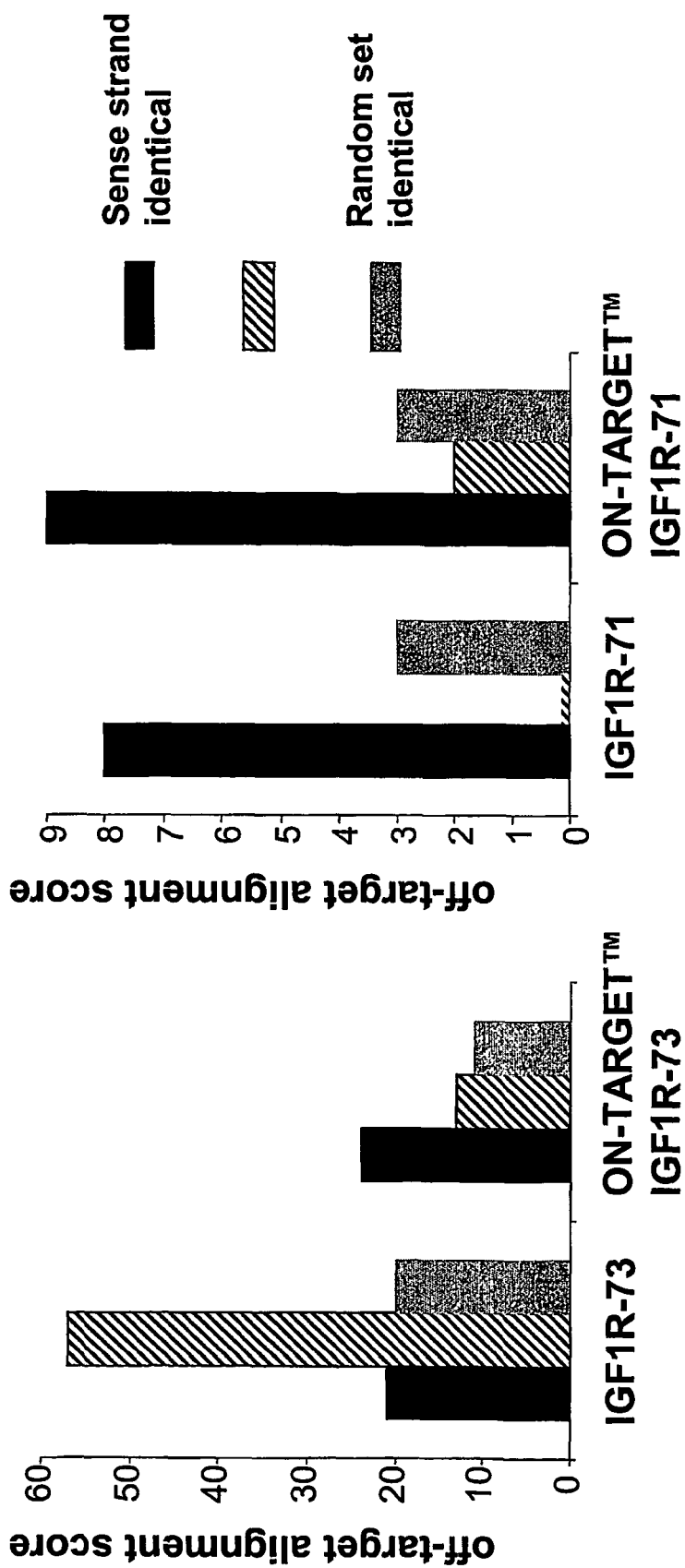

FIG. 16 shows strand bias in off-target regulation. siRNAs were aligned with signature genes. Bias towards alignment with the sense or antisense strands was determined by comparison of contiguous alignment lengths. Expected score for a random set is shown in gray. For siRNA 73, the signatures for the unmodified siRNA show identity to the antisense strand, indicating silencing due to the sense strand. With the sense-inactivated version of this siRNA, the signature genes now show identity to the sense strand, indicating silencing due to activity of the antisense strand. This verifies that both strands are functional for siRNA 73, with the sense strand being dominant. Inactivation of this strand allowed the antisense strand to become dominant. For siRNA 71, signature genes show identity to the sense strand, verifying that the antisense strand is preferentially active in this duplex, and chemical inactivation of the sense strand does not alter this signature.

Figure 17:
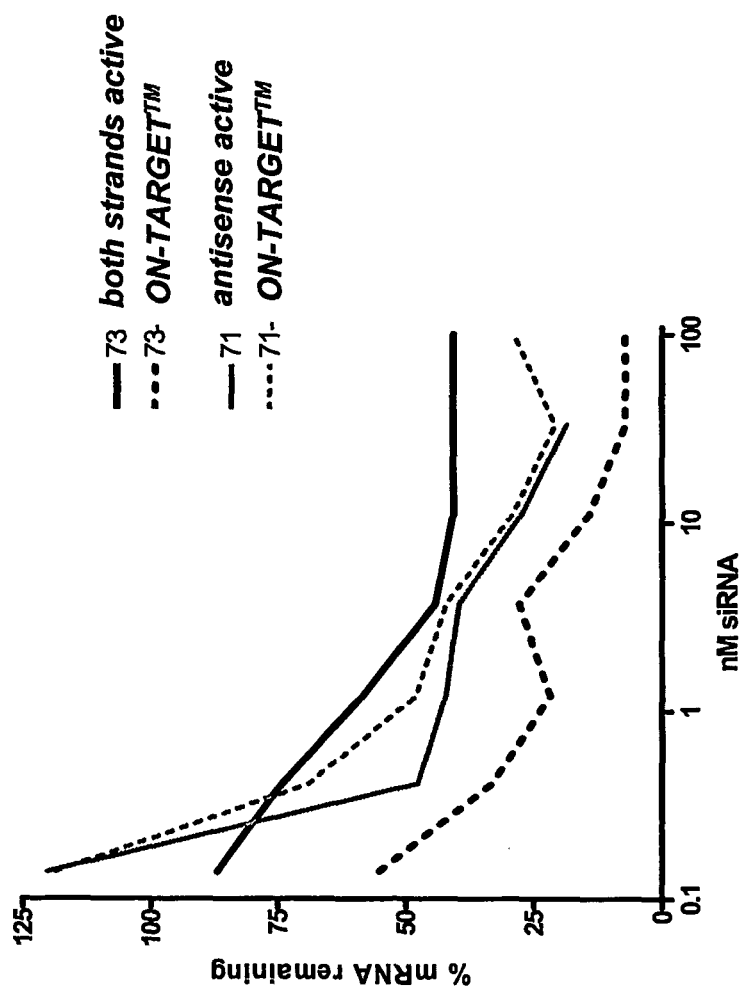

FIG. 17 shows that sense strand modification increases potency of "sense-active" siRNA. siRNA titration curve can be used to assess potency, defined as ability to maintain silencing efficacy at lower concentration. siRNAs were transfected into HeLa cells at the indicated concentrations. RNA was extracted 24 hours post-transfection, and on-target silencing was measured by Real-time PCR. The sense-active siRNA (solid black line) shows decreased potency relative to the antisense-active siRNA (solid gray line). This assay measures on-target silencing, which is a function of the activity of the antisense strand. The dominant activity of the sense strand in duplex 73 interferes with the activity of the antisense strand, thus limiting both potency and maximal efficacy. Chemical inactivation of the sense strand of this duplex significantly increases both potency and maximal efficacy (dashed black line,) presumably by freeing RISC for association with the antisense strand. This suggests that inactivation of the sense strand is one mechanism to achieve more potent siRNAs for more effective target gene silencing.

5. DETAILED DESCRIPTION OF THE INVENTION

The invention provides methods and compositions for gene silencing by RNA interference. Preferably, the methods and compositions are used for silencing an endogenous gene of an organism. In particular, the invention provides methods for gene silencing using small or short interfering RNAs (siRNAs) having only partial sequence homology to the target gene transcript, e.g., siRNAs comprising a sense strand or antisense strand central region of nucleotide sequence that is identical to a sequence in the transcript, and siRNAs having a sense strand or antisense strand 3' nucleotide sequence that is identical to a sequence in the transcript. In this application, comparison of the sequence of a strand of an siRNA and a gene of interest is often made. It will be understood that such a comparison refers to sequence comparison between the particular strand of the siRNA and the transcript of the gene. In this application, an siRNA is also said to target a gene. It will be understood that when such a statement is made, it means that the siRNA is designed to target and cause degradation of the transcript of the gene. In this application, the position of a nucleotide or a sequence of nucleotides in a strand of an siRNA is often described with reference to the 3' end of the siRNA. It will be understood that when such a description is employed, the two nucleotides of the 3' overhang are not included in the numbering of the nucleotides, i.e., the numbering of nucleotides from the 3' end begins at the first nucleotide in the duplex portion of the siRNA. The invention also provides methods for identifying genes that are commonly regulated by a plurality of different small interfering RNAs designed to target a gene. In the methods, one or more genes, the expression of which is silenced by a plurality of different siRNAs are identified based on measured response profiles to these siRNAs. The invention also provides methods for gene silencing using pool of siRNAs each targeting a different sequence in a target gene. The invention also provides methods for determining strand preference, i.e., the relative activity of the two strands of an siRNA in gene silencing. The invention further provides methods of designing siRNAs for gene silencing.

The invention is based, at least in part, on the discovery by the inventors that a central region of nucleotide sequence of, e.g., about 11-14 nucleotides, or a 3' end nucleotide sequence of, e.g., about 9 nucleotides, identical to a transcript of a gene is sufficient for an siRNA to silence the expression of a gene. Therefore, an siRNA that is designed to target a particular gene transcript may alter expression of one or more other genes (other than the target gene) if an appropriate subsequence in the siRNA is identical to a sequence in the transcripts of such other genes. Furthermore, the strand that does not target the target gene (e.g., the sense strand of an siRNA that targets a sense-identical target or the antisense strand that targets an antisense-identical target) with partial or full sequence identity may also alter expression of one or more genes. Thus, each siRNA can result in a distinct gene expression pattern in a cell. The gene expression pattern of an siRNA can be determined by expression profiling a cell subjected to the siRNA. It is also found that genes the expression of which is affected by the introduction of an siRNA can be grouped into different groups based on the kinetics of their responses. For example, it is found that for some groups of genes, the transcript levels decrease soon after the introduction of the siRNA. These groups contain genes which are silenced directly by the siRNA. For some groups of genes, the transcript levels do not decrease until a sufficiently long period of time has passed. These groups contain genes whose transcript levels are altered as a consequence of loss of the protein encoded by the gene which is targeted by the siRNA. Using separately a plurality of different siRNAs targeting a particular gene, a set of one or more genes that are commonly regulated by the plurality of siRNAs can be identified based on their response profiles.

In this application, for convenience, siRNAs consisting of 21 nucleotides are often used to illustrate the methods and compositions of the invention. It will be understood that longer siRNAs, e.g., 22- or 23-nucleotide siRNAs, are equally applicable, and are intended to be encompassed by the present invention. In this application, siRNA refers to small or short interfering RNA. It will be apparent to one skilled person in the art that small hairpin RNA (shRNA) having an appropriate sequence can be used in place of an siRNA (see, Section 5.5, infra). Such shRNAs are intended to be encompassed by the present invention. In this application a cell can be either a cultured cell or a cell in vivo.

In this application, either strand of an siRNA may act as the guiding strand in gene silencing. For convenience, the two strands of an siRNA are referred to herein as the sense strand and the antisense strand without intending to designate the direction (5' to 3' or 3' to 5') of all target transcript sequences being silenced. Generally, the designation herein of a strand of an siRNA of sense or antisense will be with respect to the direction of the sequence of a chosen transcript sequence that the siRNA can target (the reference target sequence). Thus, the antisense strand of the siRNA designates the guiding strand to this reference target sequence, whereas the sense strand designates the "identical" strand or the non-guiding strand to this reference target sequence. Any transcript sequence that the siRNA can target can be used as the reference target sequence. In preferred embodiments, the reference target sequence is the intended target sequence for which the siRNA is designed to silence. Under such a strand designation convention, the sense strand of the siRNA may act as the guiding strand in targeting another sequence in the same or a different transcript.

5.1. Biological State and Expression Profile

The state of a cell or other biological sample is represented by cellular constituents (any measurable biological variables) as defined in Section 5.1.1, infra. Those cellular constituents vary in response to perturbations, or under different conditions. The measured signals can be measurements of such cellular constituents or measurements of responses of cellular constituents.

5.1.1 Biological State

As used herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms. In preferred embodiments, the biological sample comprises a living cell or organism.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of an siRNA or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample) e.g., of mRNA or proteins, or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample.

One aspect of the biological state of a biological sample (e.g., a cell or cell culture) usefully measured in the present invention is its transcriptional state. In fact, the transcriptional state is the currently preferred aspect of the biological state measured in this invention. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of an siRNA or other perturbation of interest. The transcriptional state of a biological sample can be conveniently determined by, e.g., measuring cDNA abundances by any of several existing gene expression technologies. One particularly preferred embodiment of the invention employs DNA arrays for measuring mRNA or transcript level of a large number of genes. The other preferred embodiment of the invention employs DNA arrays for measuring expression levels of a large number of genes or exons in the genome of an organism.

Another aspect of the biological state of a biological sample usefully measured in the present invention is its translational state. The translational state of a biological sample includes the identities and abundances of the constituent protein species in the biological sample under a given set of conditions. Preferably, a substantial fraction of all constituent protein species in the biological sample is measured, but at least a sufficient fraction is measured to characterize the action of an siRNA of interest. As is known to those of skill in the art, the transcriptional state is often representative of the translational state.

Still another aspect of the biological state of a biological sample is its small molecule state, e.g., metabolic state. The small molecule state of a biological sample comprises identities and abundances of small molecules present in a cell. Small molecules refer to molecules of molecular weights of less than about 5000, including but are not limited to sugars, fatty acids, amino acids, nucleotides, intermediates of cellular processes, e.g., intermediates of metabolic and signaling pathways.

Other aspects of the biological state of a biological sample are also of use in this invention. For example, the activity state of a biological sample, as that term is used herein, includes the activities of the constituent protein species (and also optionally catalytically active nucleic acid species) in the biological sample under a given set of conditions. As is known to those of skill in the art, the translational state is often representative of the activity state.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

The biological state of a biological sample (e.g., a cell or cell culture) is represented by a profile of some number of cellular constituents. Such a profile of cellular constituents can be represented by the vector S, $$S = (S_1, \ldots, S_i, \ldots, S_k) \qquad (1)$$

where $S_i$ is the level of the i'th cellular constituent, for example, the transcript level of gene i, or alternatively, the abundance or activity level of protein i. In preferred embodiments, k is more than 2, preferably more than 10, more preferably more than 100, still more preferably more than 1000, still more preferably more than 10,000, still more preferably more than 25,000, still more preferably more than 50,000, and most preferably more than 100,000.

In some embodiments, cellular constituents are measured as continuous variables. For example, transcriptional rates are typically measured as number of molecules synthesized per unit of time. Transcriptional rate may also be measured as percentage of a control rate. However, in some other embodiments, cellular constituents may be measured as categorical variables. For example, transcriptional rates may be measured as either "on" or "off", where the value "on" indicates a transcriptional rate above a predetermined threshold and value "off" indicates a transcriptional rate below that threshold.

5.1.2 Biological Responses and Expression Profiles

The responses of a biological sample to a perturbation, i.e., under a condition, such as the application of an siRNA, can be measured by observing the changes in the biological state of the biological sample. For example, the responses of a biological sample can be responses of a living cell or organism to a perturbation, e.g., application of an siRNA, a genetic mutation, an environmental change, and so on, to the living cell or organism. A response profile is a collection of changes of cellular constituents. In the present invention, the response profile of a biological sample (e.g., a cell or cell culture) to the perturbation m is defined as the vector $v^{(m)}$:

$$v^{(m)} = (v_1^{(m)}, \ldots, v_i^{(m)}, \ldots, v_k^{(m)}) \quad (2)$$

where $v_i^{(m)}$ is the amplitude of response of cellular constituent i under the perturbation m. In some particularly preferred embodiments of this invention, the biological response to the application of an siRNA, a drug, a drug candidate or any other perturbation, is measured by the induced change in the transcript level of at least 2 genes and/or proteins, preferably more than 10 genes and/or proteins, more preferably more than 100 genes and/or proteins, still more preferably more than 1000 genes and/or proteins, still more preferably more than 10,000 genes and/or proteins, still more preferably more than 25,000 genes and/or proteins, still more preferably more than 50,000 genes and/or proteins, and most preferably more than 100,000 genes and/or proteins.

In some embodiments of the invention, the response is simply the difference between biological variables before and after perturbation. In some preferred embodiments, the response is defined as the ratio of cellular constituents before and after a perturbation is applied. In other embodiments, the response may be a function of time after the perturbation, i.e., $v^{(m)} = v^{(m)}(t)$. For example $v^{(m)}(t)$ may be the difference or ratio of cellular constituents before the perturbation and at time t after the perturbation.

In some preferred embodiments, $v_i^{(m)}$ is set to zero is the response of gene i is below some threshold amplitude or confidence level determined from knowledge of the measurement error behavior. In such embodiments, those cellular constituents whose measured responses are lower than the threshold are given the response value of zero, whereas those cellular constituents whose measured responses are greater than the threshold retain their measured response values. This truncation of the response vector is a good strategy when most of the smaller responses are expected to be greatly dominated by measurement error. After the truncation, the response vector $v^{(m)}$ also approximates a 'matched detector' (see, e.g., Van Trees, 1968, *Detection, Estimation, and Modulation Theory Vol. I*, Wiley & Sons) for the existence of similar perturbations. It is apparent to those skilled in the art that the truncation levels can be set based upon the purpose of detection and the measurement errors. For example, in some embodiments, genes whose transcript level changes are lower than two folds or more preferably four folds are given the value of zero.

In some preferred embodiments, perturbations are applied at several levels of strength. For example, different amounts of an siRNA may be applied to a biological sample to observe its response. In such embodiments, the perturbation responses may be interpolated by approximating each by a single parameterized "model" function of the perturbation strength u. An exemplary model function appropriate for approximating transcriptional state data is the Hill function, which has adjustable parameters a, $u_0$, and n.

$$H(u) = \frac{a(u/u_0)^n}{1+(u/u_0)^n} \quad (3)$$

The adjustable parameters are selected independently for each cellular constituent of the perturbation response. Preferably, the adjustable parameters are selected for each cellular constituent so that the sum of the squares of the differences between the model function (e.g., the Hill function, Equation 3) and the corresponding experimental data at each perturbation strength is minimized. This preferable parameter adjustment method is well known in the art as a least squares fit. Other possible model functions are based on polynomial fitting, for example by various known classes of polynomials. More detailed description of model fitting and biological response has been disclosed in Friend and Stoughton, Methods of Determining Protein Activity Levels Using Gene Expression Profiles, PCT publication WO 99/59037, which is incorporated herein by reference in its entirety for all purposes.

5.2. Method of Identifying Common Responses to a Plurality of Short Interfering RNAS Targeting a Gene The invention provides methods for identifying one or more genes that are commonly silenced by a plurality of different small interfering RNAs designed to silence a target gene and that are different from the target gene. Such one or more genes are also referred to as "non-target" or "off-target" genes. In the invention, non-target genes can be identified based on measured response profiles to the plurality of siRNAs.

5.2.1. Response Profile of a Short Interfering RNA

The invention provides methods of determining response profiles of an siRNA. In the methods, mRNA levels and/or levels of encoded proteins of a plurality of genes in a cell subjected to perturbation by an siRNA are measured. Preferably, the response profiles of an siRNA are measured at a selected time point after the introduction of the siRNA molecules into the cell. In some embodiments of the invention, when the kinetics of the response to the siRNA is to be determined, a plurality of response profiles can be measured at a plurality of different time points after the introduction of the siRNA.

The mRNA and/or protein levels in a cell subjected to perturbation by an siRNA can be measured by any standard method known in the art. Preferably, a substantial fraction of all constituent species in the cell are measured. In a preferred embodiment, mRNA levels are measured using DNA microarrays. Preferably, more than 5, more than 10, more than 100, more than 1000, more than 10,000, more than 25,000, more than 50,000, or more than 100,000 mRNA species are measured for the response profile of an siRNA. In another preferred embodiment, protein levels are measured 2D gel electrophoresis or protein arrays. Preferably, more than 5, more than 10, more than 100, more than 1000, more than 10,000, more than 25,000, more than 50,000, or more than 100,000 protein species are measured for the response profile of an siRNA.

Figure 1A:
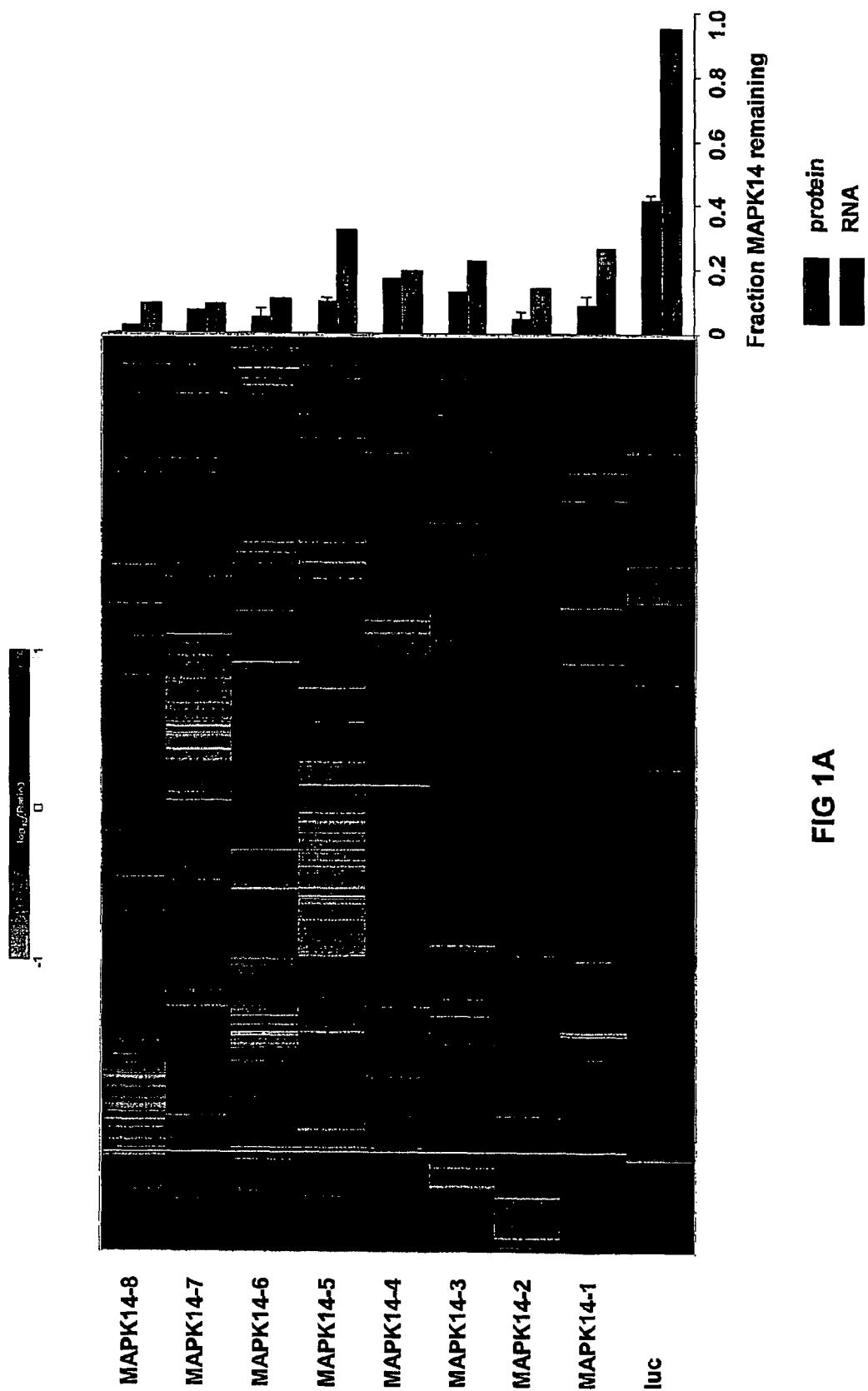
Figure 1B:
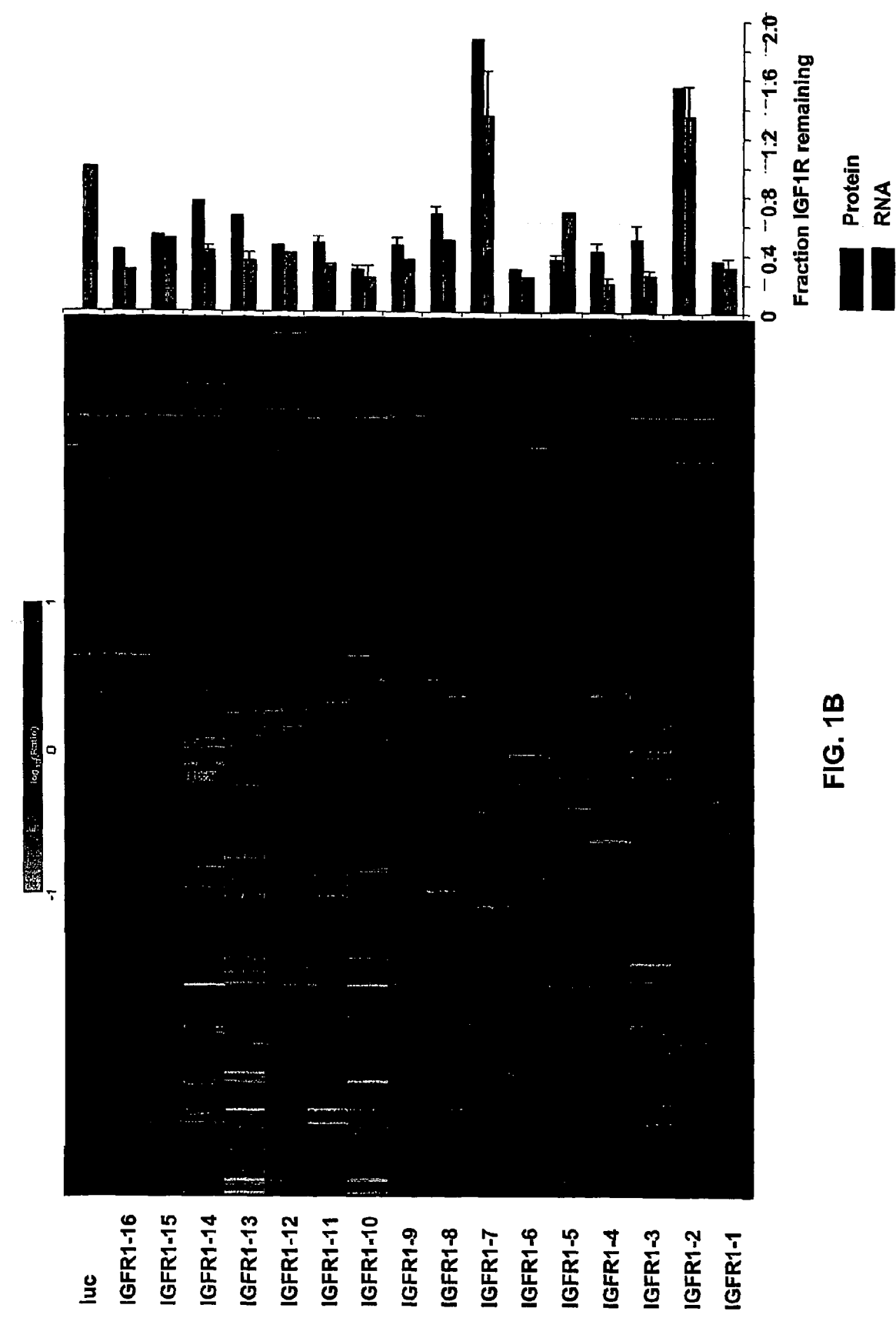

As an exemplary embodiment, 21-nucleotide double-stranded siRNAs targeting the coding regions of IGF1R or MAPK14 were designed according to standard selection rules (see, e.g., Elbashir et al., 2002, *Methods* 26:199-213). A total of sixteen siRNAs targeting IGF1R and eight siRNAs targeting MAPK14 (Table I) were designed. These siRNAs were transfected individually into HeLa cells. The expression profiles resulting from silencing of the same target gene by different siRNAs were obtained. The expression profiles comprised measured transcript levels of about 21,000 human genes, measured using microarrays containing oligonucleotides corresponding to the 21,000 human genes. Portions of the measured response profiles of these siRNAs are illustrated in FIGS. 1A and 1B. Each of the eight siRNA duplexes targeting MAPK14 produced a distinct expression pattern (FIG. 1A). Likewise, each of the sixteen siRNA duplexes to IGF1R produced a unique expression pattern (FIG. 1B). Virtually identical gene expression patterns were observed in three independent experiments, demonstrating that gene regulation resulting from a particular siRNA is reproducible. These results suggested that different siRNAs to the same target transcript elicit a small number of gene regulations in common, but the vast majority of the transcript expression patterns were siRNA-specific rather than target-specific.

The number and identity of altered transcripts may include genes other than the target gene. All of the MAPK14 siRNA duplexes effectively silenced the target, demonstrating greater than 80% reduction in RNA and protein levels, yet each siRNA also regulates the expression of a different number of transcripts other than MAPK14 (FIG. 1A). Eleven of the sixteen IGF1R siRNAs decreased IGF1R protein level by approximately 60-80% (FIG. 1B). Two IGF1R siRNAs reproducibly increase IGF1R protein and RNA levels. IGF1R-4 decreases the expression of IGF1R by 80%, yet results in the altered expression of fewer genes than IGF1R-5, which produced only 30% silencing of the target. Furthermore, an siRNA targeted to luciferase reproducibly regulated the expression of several genes despite the lack of a homologous target in the human genome; the number of transcripts regulated by the luciferase siRNA was greater than that for a same versus same control. Thus, from expression profiling, it is shown that observed patterns of gene regulation are specific for the siRNA sequence utilized for silencing, rather than the intended target.

The invention thus also provides a method of determining an effect of an siRNA on an eukaryotic cell. The method comprises determining an expression profile of the eukaryotic cell at one or more chosen times after introduction of the siRNA into the cell.

5.2.2. Method of Identifying Common Response Pattern of One or More Short Interfering RNAS The common response pattern of a cell to one or more siRNAs can be identified using the response profiles of the cell to the one or more siRNAs. In a preferred embodiment, genes commonly silenced by a single siRNA are identified by analyzing the kinetics of response profiles of the siRNA. In another preferred embodiment, genes commonly silenced by a plurality of different siRNAs are identified by analyzing a plurality of response profiles of the plurality of different siRNAs.

5.2.2.1. Method of Identifying Genes Directly Silenced by a Short Interfering RNA Using Kinetic Data The invention provides methods for identifying gene or genes which are silenced by an siRNA directly, i.e., gene or genes whose mRNA level change due to the direct effect of the siRNA rather than due to the loss of one or more proteins encoded by one or more other genes which are silenced by the siRNA.

Figure 2:
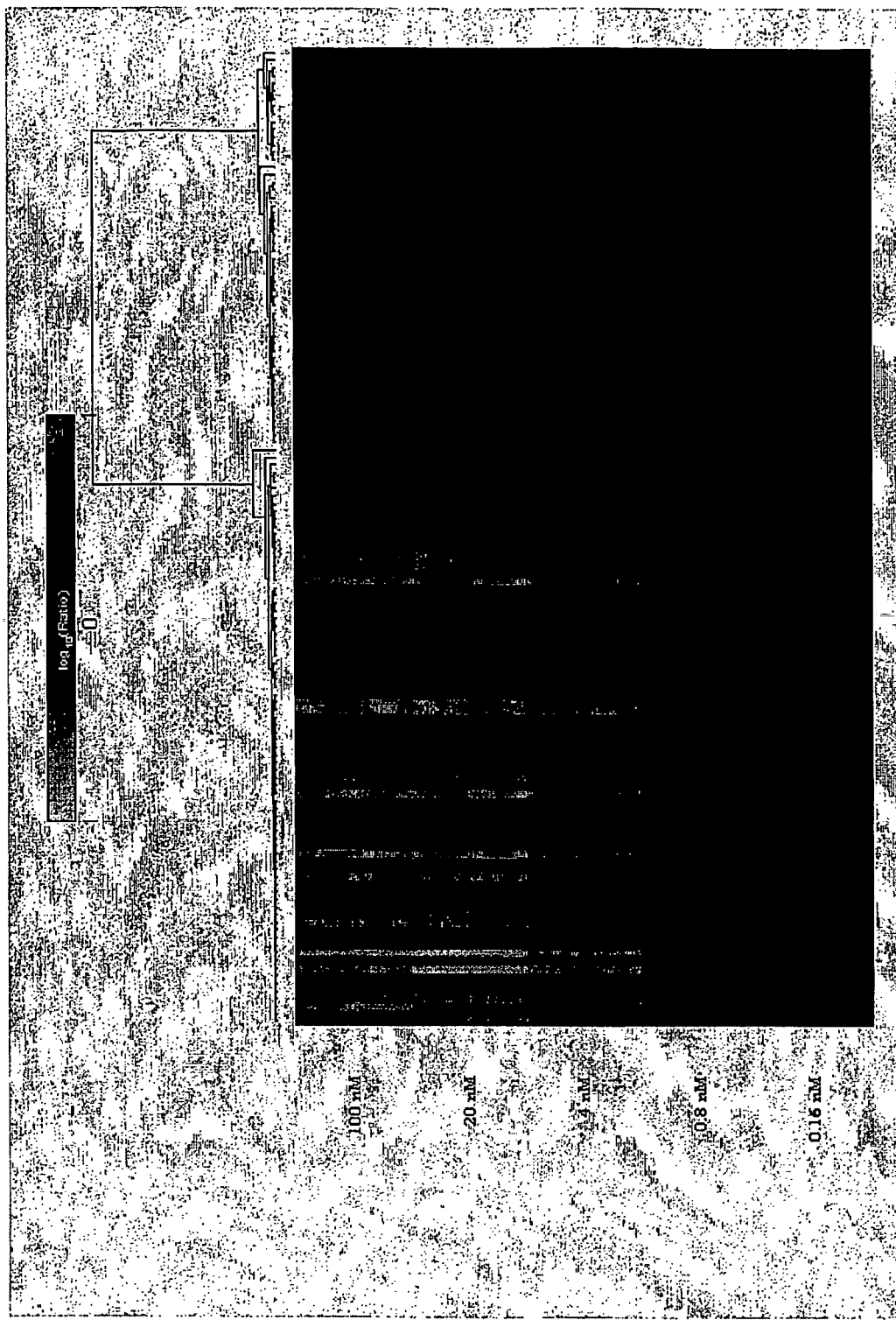

In a preferred embodiment, the dependence of the silencing of a gene on the siRNA concentration is measured and analyzed. In a preferred embodiment, mRNA level of a gene, e.g., the target or a non-target gene, and/or the encoded protein level are measured under a plurality of different concentrations of the siRNA. The characteristics of the concentration dependence of the silencing of the gene is then compared between the non-target gene and the target gene silencing. In one embodiment, the half-maximal responses with respect to siRNA concentration is used to characterized the concentration dependence. In an embodiment, if there is no difference in the off-target gene regulation from silencing of the intended target gene, this indicates that off-target gene regulation is not simply an artifact of high siRNA concentration. In an exemplary embodiment, a concentration analysis of MAPK14 protein and RNA knockdown by siRNA MAPK14-1 was carried out. Although target gene silencing was detectable when the siRNA concentration was decreased by 1000-fold, off-target gene regulation was also detectable (FIG. 2). Many of these genes show nearly identical half-maximal responses with respect to siRNA concentration as MAPK14 (~4 nM). The fact that it was unable to titrate the off-target gene regulation from silencing of the intended target indicated that off-target gene regulation was not simply an artifact of high siRNA concentration.

In another preferred embodiment, kinetics of the silencing of a gene is measured and analyzed. In a preferred embodiment, the mRNA level of a gene, e.g., the target or a non-target gene, and/or the encoded protein level is measured at a plurality of different time points after the introduction of the siRNA into cells. The characteristics of the temporal profile of the transcript level of the gene can then be used to determine whether the gene is silenced by the siRNA directly or through some secondary effect, e.g., as a consequence of loss of the protein encoded by a gene silenced by the siRNA. In one embodiment, the time of half-maximal degradation of the mRNA is used to characterized the time dependence. The silencing of a non target gene with a kinetics faster than the lifetime of the protein encoded by the gene silenced by the siRNA, e.g., with a time of half-maximal degradation shorter than the half-life of the protein, indicates that the gene may be silenced directly rather than due to loss of the targeted protein.

The temporal profiles of expression profiles can be determined using any standard method known in the art. In some preferred embodiments of the invention, expression levels of a plurality of genes are measured at a plurality of different times after the delivery of siRNA into the cells. In such embodiments, expression levels are most preferably measured at time points spanning the range from 0, i.e., immediately after siRNA introduction, to a time point sufficiently long that effect on the expression levels of downstream genes due to loss of the protein encoded by the target gene are observable. Preferably, the plurality of times includes time points spanning the range from 0 to a time point at which the level of the protein encoded by the target gene decreases to about 50% of its unperturbed level. In one embodiment, the plurality of times includes time points at which the level of the protein encoded by the target gene decreases to about 10%, 20%, 30%, 40%, 50% of its unperturbed level. The time point at which the level of the protein encoded by the target gene decreases to 50% of its unperturbed level is also called the "half life" of the protein. More preferably, the expression levels are measured at times as long as about two times the half life of the protein encoded by the target gene. For example, MAPK14 protein has a half life of about 40 hours. Thus, in embodiments in which MAPK14 is the target gene, typical hybridization times may be approximately 0-40 hours, more preferably approximately 0-80 hours. In a preferred embodiment, the half life of the target protein is determined concurrently with the measurements of expression levels. For example, at each time point when an expression profile is measured, the abundance of the target protein is also measured.

In one embodiment, the expression profile of a plurality of genes at different time points are measured separately on different, identical microarrays. For each such measurement, at time when expression level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted expression levels are then combined to form an expression kinetics curve. In another embodiment, expression levels are measured in real time using a single microarray. In this embodiment, the microarray is allowed to hybridize to the sample without interruption and the microarray is interrogated at each time in a non-invasive manner. In still another embodiment, one can use one array, hybridize for a short time, wash and measure the hybridization level, put back to the same sample, hybridize for another period of time, wash and measure again to get the expression kinetics curve.

Figure 3A:
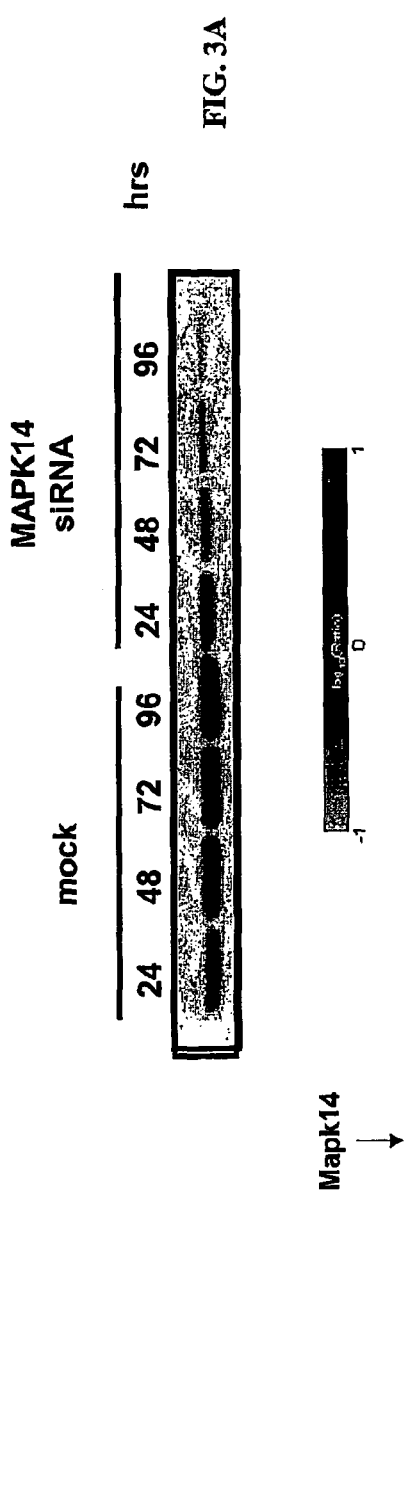
Figure 3B:
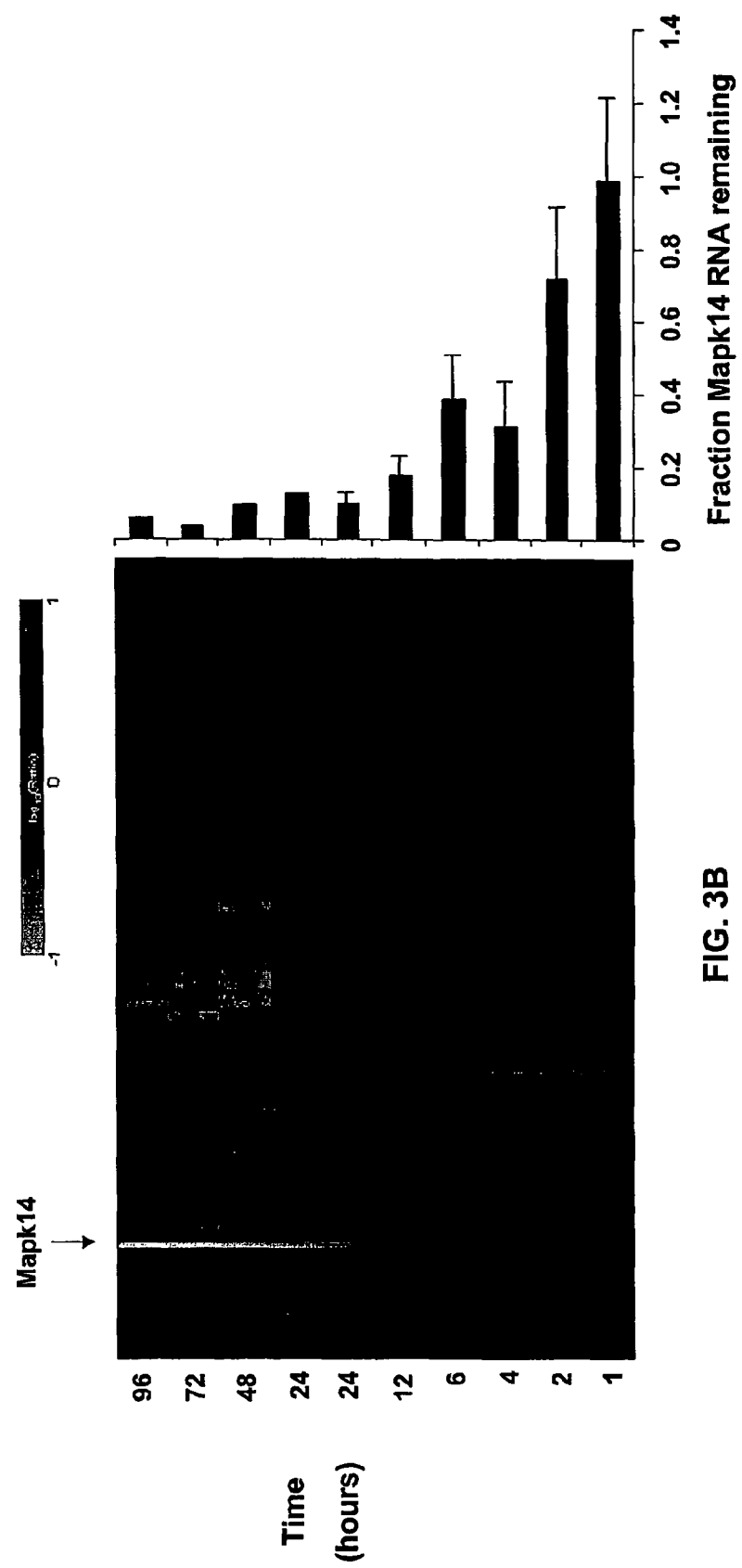
Figure 3C:
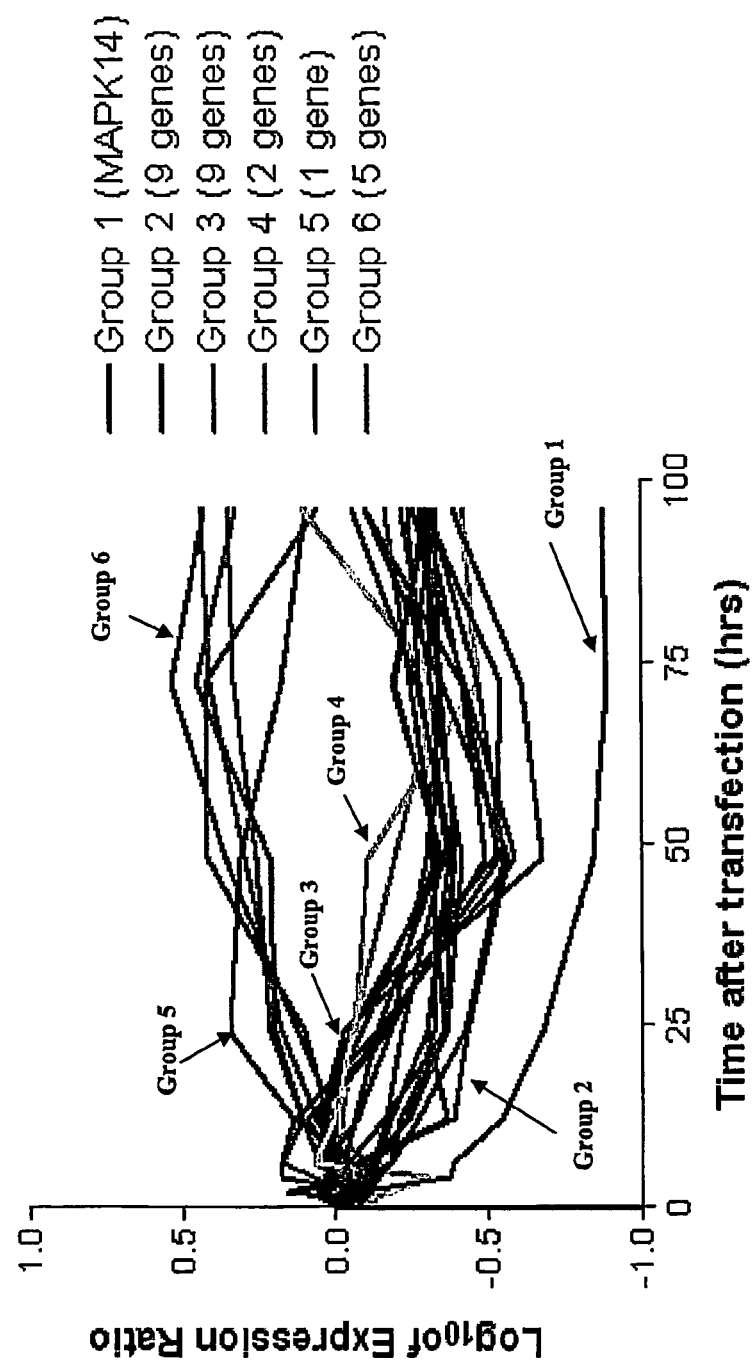

In an exemplary embodiment, the temporal gene expression patterns were measured and analyzed. The Mapk14 protein demonstrated a half-life of approximately 40 hours following siRNA transfection (FIG. 3A). In contrast, the Mapk14 transcript was rapidly degraded, demonstrating half-maximal degradation approximately 11 hours post-transfection (FIG. 3B). Through expression profiling, gene regulation of a plurality of non target genes at early time points (6-12 hours) was observed well before any observable decrease in the MAPK protein. These gene expression changes were not secondary events resulting from loss of MAPK function. Further analysis revealed that the expression signature could be divided into several temporally distinct groups of transcripts (FIG. 3C). Group 1 contains a single transcript, the intended target MAPK14. Group 2 contains nine transcripts demonstrating similar kinetics of silencing to MAPK14, with half-maximal degradation at 7-13 hours as determined by microarray. This same group of transcripts was down-regulated with rapid kinetics in a separate experiment, demonstrating that these genes were reproducibly silenced by this siRNA. The rapid kinetics of transcript regulation suggested that these were direct transcript degradation events. This is in contrast to kinetic groups 3 and 4, for which half-maximal degradation occurs at approximately 40 hours and therefore likely represent secondary gene expression changes.

The invention thus also provides a method of determining an effect of an siRNA on an eukaryotic cell, comprising determining an expression profile of the eukaryotic cell comprising measurements of transcript levels of a plurality of different genes at a plurality of different times after introduction of the siRNA into the cell, and grouping the plurality of different genes into different kinetic groups based on the kinetic behavior of said measured transcript levels. The method can be used to distinguish genes that are directly silenced by the siRNA and genes that are affected by the loss of a protein encoded by a directly silenced gene.

The invention also provides a method for identifying the functions of a target gene, e.g., the downstream genes regulated by the target gene, based on the kinetic behavior of response profile of an siRNA designed to silence the target gene. Preferably, the siRNA is designed to silence the target gene but not one or more other genes. In one embodiment, the invention provides a method of identifying one or more genes that are regulated by a first protein but not by a second protein in an eukaryotic cell, comprising (a) introducing into said eukaryotic cell molecules of an siRNA molecule that comprises (i) a sense strand or antisense strand central contiguous nucleotide sequence of 11-18 nucleotides that is identical to a sequence of a transcript of a first gene encoding said first protein, or (ii) a 3' sense strand or antisense strand contiguous nucleotide sequence of 9-18 nucleotides that is identical to a sequence of said transcript of said first gene, and that does not comprise (iii) any sense strand or antisense strand central contiguous nucleotide sequences of 11-18 nucleotides that are identical to a sequence of a transcript of a second gene encoding said second protein and (iv) any 3' sense strand or antisense strand contiguous nucleotide sequences of 9-18 nucleotides that are identical to a sequence of said transcript of said second gene; (b) determining an expression profile of said eukaryotic cell after a period of time after introduction of said siRNA, wherein each said expression profile comprises measured transcript levels of a plurality of different genes, and wherein said period of time is longer than the lifetime of said first protein; and (c) identifying one or more genes, transcript levels of which are altered from their levels in cells not subjected to said siRNA.

5.2.2.2. Method of Identifying Common Response Pattern

The invention provides methods for identifying common response patterns to a plurality of siRNAs targeting one or more genes. The plurality of siRNAs can comprise 3, 5, 8, 10, 16, 50, 100, 1,000, or more siRNAs. The measured expression levels in the set of response profiles of the plurality of siRNAs targeting the gene or genes can be grouped into co-varying sets according to their tendency to co-vary in response to the perturbations by these siRNAs. The set or sets of genes so identified represent common responses of the cell to the plurality of siRNAs. Expression levels of genes can also be determined by analyzing the abundances of the encoded proteins.

In some preferred embodiments, the common responses are determined based on response profiles measured at the same time after the introduction of an siRNA or precursor of an siRNA, e.g., a plasmid encoding an shRNA, into a cell. In some embodiments, the common responses are determined based on response profiles measured at an early time point. An early time point refers to a time point at which the level of the protein encoded by the target gene has not decreased to about 50% of its unperturbed level, e.g., a level of the protein in cells not subject to the siRNA. In one embodiment, the common responses are determined based on response profiles measured at a time point at which the level of the protein encoded by the target gene decreases to about 10% of its unperturbed level. In another embodiment, the common responses are determined based on response profiles measured at a time point at which the level of the protein encoded by the target gene decreases to about 20% of its unperturbed level. In still another embodiment, the common responses are determined based on response profiles measured at a time point at which the level of the protein encoded by the target gene decrease to about 30% of its unperturbed level. In still another embodiment, the common responses are determined based on response profiles measured at a time point at which the level of the protein encoded by the target gene decreases to about 40% of its unperturbed level. Genes that are commonly silenced by an siRNA at an early time point are often genes that are directly silenced by the siRNA.

In another embodiment, the common responses are determined based on response profiles measured at a late time point. A late time point refers to a time point at which the level of the protein encoded by the target gene decreases to at least about 50% of its unperturbed level. In one embodiment, the common responses are determined based on response profiles measured at a time point at which the level of the protein encoded by the target gene decrease to about 50% of its unperturbed level. In another embodiment, the common responses are determined based on response profiles measured at a time point at which the level of the protein encoded by the target gene decreases to about 60% of its unperturbed level. In still another embodiment, the common responses are determined based on response profiles measured at a time point at which the level of the protein encoded by the target gene decreases to about 75% of its unperturbed level. In still another embodiment, the common responses are determined based on response profiles measured at a time point at which the level of the protein encoded by the target gene decreases to about 90% of its unperturbed level. In still other embodiments, the common responses are determined based on response profiles measured at a time point twice as long as the time point at which the level of the protein encoded by the target gene decreases to about 50% of its unperturbed level.

Methods for grouping measured expression levels in co-varying sets and identifying common responses are known in the art. See, e.g., U.S. Pat. No. 6,203,987 and U.S. patent application Ser. No. 09/220,142, both of which are incorporated herein by reference in their entirety. Preferably, the co-varying sets of the present invention are identified by means of a clustering algorithm (i.e., by means of "clustering analysis").

The clustering methods and algorithms that can be employed in the present invention include both "hierarchical" or "fixed-number-of groups" algorithms (see, e.g., S-Plus Guide to Statistical and Mathematical Analysis v. 3.3, 1995, MathSoft, Inc.: StatSci. Division, Seattle, Wash.). Such algorithms are well known in the art (see, e.g., Fukunaga, 1990, *Statistical Pattern Recognition*, 2nd Ed., San Diego: Academic Press; Everitt, 1974, *Cluster Analysis*, London: Heinemann Educ. Books; Hartigan, 1975, *Clustering Algorithms*, New York: Wiley; Sneath and Sokal, 1973, *Numerical Taxonomy*, Freeman; Anderberg, 1973, *Cluster Analysis for Applications*, New York: Academic Press), and include, e.g., hierarchical agglomerative clustering algorithms, the "k-means" algorithm of Hartigan, and model-based clustering algorithms such as mclust by MathSoft, Inc. Preferably, hierarchical clustering methods and/or algorithms are employed in the methods of this invention. In a particularly preferred embodiment, the clustering analysis of the present invention is done using the hclust routine or algorithm (see, e.g., 'hclust' routine from the software package S-Plus, Math-Soft, Inc., Cambridge, Mass.).

The clustering algorithms used in the present invention operate on a table of data containing gene expression measurements. Specifically, the data table analyzed by the clustering methods of the present invention comprise an m×k array or matrix wherein m is the total number of conditions or perturbations, i.e., total number of different siRNAs, and k is the number of cellular constituents, e.g., transcripts of genes, measured and/or analyzed.

The clustering algorithms analyze such arrays or matrices to determine dissimilarities between cellular constituents. Mathematically, dissimilarities between cellular constituents i and j are expressed as "distances" $I_{i,j}$. For example, in one embodiment, the Euclidian distance is determined according to the formula $$I_{i,j} = \left( \sum_n |v_i^{(n)} - v_j^{(n)}|^2 \right)^{1/2} \tag{4}$$

where $v_i^{(n)}$ and $v_j^{(n)}$ are the response of cellular constituents i and j respectively to the perturbation n. In other embodiments, the Euclidian distance in Equation 4 above is squared to place progressively greater weight on cellular constituents that are further apart. In alternative embodiments, the distance measure $I_{i,j}$ is the Manhattan distance provide by $$I_{i,j} = \sum_n |v_i^{(n)} - v_j^{(n)}| \tag{5}$$

In another embodiment, the distance is defined as $I_{i,j}=1-r_{ij}$, where $r_{i,j}$ is the "correlation coefficient" or normalized "dot product" between the response vectors $v_i$ and $v_j$. For example, $r_{i,j}$ is defined by $$r_{i,j} = \frac{v_i \cdot v_j}{|v_i||v_j|} \tag{6}$$

wherein the dot product $v_i \cdot v_j$ is defined by $$v_i \cdot v_j = \sum_n v_i^{(n)} \cdot v_j^n \tag{7}$$

and $|v_i| = (v_i \cdot v_i)^{1/2}$; and $|v_j| = (v_j \cdot v_j)^{1/2}$

In still other embodiments, the distance measure may be the Chebychev distance, the power distance, and percent disagreement, all of which are well known in the art. In another embodiment, the distance measure is $I_{i,j}=1-r_{i,j}$ with the correlation coefficient which comprises a weighted dot product of the response vector $v_i$ and $v_j$. Specifically, in this embodiment, $r_{ij}$ is preferably defined by the equation $$r_{i,j} = \frac{\sum_n \frac{v_i^{(n)} \cdot v_j^{(n)}}{\sigma_i^{(n)} \cdot \sigma_j^{(n)}}}{\left[ \sum_n \left(\frac{v_i^{(n)}}{\sigma_i^{(n)}}\right)^2 \cdot \sum_n \left(\frac{v_j^{(n)}}{\sigma_j^{(n)}}\right)^2 \right]^{1/2}} \tag{8}$$

where $\Phi_i^{(n)}$ and $\Phi_j^{(n)}$ are the standard errors associated with the measurement of the i'th and j'th cellular constituents, respectively, in experiment n.

The correlation coefficients of Equations 6 and 8 are bounded between values of +1, which indicates that the two response vectors are perfectly correlated and essentially identical, and −1, which indicates that the two response vectors are "anti-correlated" or "anti-sense" (i.e., are opposites). These correlation coefficients are particularly preferable in embodiments of the invention where cellular constituent sets or clusters are sought of constituents which have responses of the same sign.

In other embodiments, it is preferable to identify cellular constituent sets or clusters which are co-regulated or involved in the same biological responses or pathways, but which comprise similar and anti-correlated responses. In such embodiments, it is preferable to use the absolute value of Equation 6 or 8, i.e., $|r_{i,j}|$, as the correlation coefficient.

In still other embodiments, the relationships between co-regulated and/or co-varying cellular constituents may be even more complex, such as in instance wherein multiple biological pathways (e.g., signaling pathways) converge on the same cellular constituent to produce different outcomes. In such embodiments, it is preferable to use a correlation coefficient $r_{ij}=r_{ij}^{(change)}$ which is capable of identifying co-varying and/or co-regulated cellular constituents irrespective of the sign. The correlation coefficient specified by Equation 9 below is particularly useful in such embodiments.

$$r_{i,j}^{change} = \frac{\sum_n \left|\frac{v_i^{(n)}}{\sigma_i^{(n)}}\right|\left|\frac{v_j^{(n)}}{\sigma_j^{(n)}}\right|}{\left[\sum_n \left(\frac{v_i^{(n)}}{\sigma_i^{(n)}}\right)^2 \cdot \sum_n \left(\frac{v_j^{(n)}}{\sigma_j^{(n)}}\right)^2\right]^{1/2}} \qquad (9)$$

Generally, the clustering algorithms used in the methods of the invention also use one or more linkage rules to group cellular constituents into one or more sets or "clusters." For example, single linkage or the nearest neighbor method determines the distance between the two closest objects (i.e., between the two closest cellular constituents) in a data table. By contrast, complete linkage methods determine the greatest distance between any two objects (i.e., cellular constituents) in different clusters or sets. Alternatively, the unweighted pair-group average evaluates the "distance" between two clusters or sets by determining the average distance between all pairs of objects (i.e., cellular constituents) in the two clusters. Alternatively, the weighted pair-group average evaluates the distance between two clusters or sets by determining the weighted average distance between all pairs of objects in the two clusters, wherein the weighing factor is proportional to the size of the respective clusters. Other linkage rules, such as the unweighted and weighted pair-group centroid and Ward's method, are also useful for certain embodiments of the present invention (see, e.g., Ward, 1963, *J. Am. Stat. Assn* 58:236; Hartigan, 1975, *Clustering Algorithms*, New York: Wiley).

Once a clustering algorithm has grouped the cellular constituents from the data table into sets or cluster, e.g., by application of linkage rules such as those described supra, a clustering "tree" may be generated to illustrate the clusters of cellular constituents so determined. In FIGS. 1A and 1B, clustering trees generated by the hclust clustering algorithm upon analysis of the response profile data illustrated in the figures are presented on top of the response profile data display. The measured response data $\{v_i^{(n)}\}$ comprise the logarithm to the base 10 of the ratio between abundances of each transcript i in the pair of conditions (i.e., siRNA perturbation and no perturbation) comprising each differential experiment n.

The cellular constituents are re-ordered according to the cellular constituent sets or clusters obtained or provided by the above-described methods, and visually displayed. Analytically, such a reordering corresponds to transforming a particular original biological response profile, such as a particular perturbation response profile, e.g., $v^{(n)}=\{v_i^{(n)}\}$ to the re-ordered profile $\{v_{A(i)}^{(n)}\}$, where i is the cellular constituent index.

FIGS. 1A and 1B show such re-ordered measurements of the cellular constituents. In particular, FIG. 1A shows a plurality of genetic transcripts (i.e., cellular constituents; horizontal axis) measured in 9 different experiments, in 8 of which cells were exposed to different siRNAs targeting the MAPK14 gene and in 1 of which cells were exposed to siRNA targeting luciferase (i.e., perturbation response profiles, vertical index). FIG. 1B illustrates a plurality of genetic transcripts measured in 17 different experiments, in 16 of which cells were exposed to different siRNAs targeting the IGF1R gene and in 1 of which cells were exposed to an siRNA targeting luciferase.

In preferred embodiments, the cellular constituents activated (or de-activated) by members of a group of siRNAs may be identified by either qualitative or quantitative methods.

In one embodiment, the cellular constituents are identified by visual inspection of response profile data for a plurality of perturbations. Preferably, such data is re-ordered, according to, e.g., the methods described above so that co-varying cellular constituents, and similar response profiles may be more readily identified. For example, FIG. 1A shows a plurality of genetic transcripts (horizontal axis) measured in a plurality of experiment, i.e., response profiles, wherein HeLa cells were exposed to the siRNAs targeting the MAPK14 gene and luciferase as indicated on the vertical axis. The cellular constituents have been grouped and re-ordered so the co-varying cellular constituents (i.e., genesets) can be readily visualized. Visual inspection of FIG. 1A reveals that expressions of genes corresponding to rows on the left hand side of the display are reduced in all or a large number of different siRNA experiments. By contrast, expressions of genes corresponding to rows on the right hand side of the display show diverse responses, including enhancements.

In more quantitative embodiments, the intersections of genes are preferably identified, e.g., by thresholding the individual response amplitudes in the response profiles. In one embodiment, the response amplitude is a ratio of perturbed and unperturbed sample and the threshold is set as two, four or ten folds reduction of expression levels.

In a preferred embodiment, the statistical significance of the response of a gene in one or more profiles is also determined. In one embodiment, the measured response of a gene is transformed by a transformation as in Weng, U.S. patent application Ser. No. 10/349,364, filed on Jan. 22, 2003 and Weng, U.S. patent application Ser. No. 10/354,664, filed on Jan. 30, 2003, each of which is incorporated by reference herein in its entirety. The statistical significance of the response is then determined based on the transformed response. In one embodiment, the statistical significance is characterized by a p value, indicating the probability that the variation in the transformed response is due to random errors. In a preferred embodiment, genes whose responses have a fold change above a given threshold level with a p value less than a given threshold level are selected as significantly regulated genes.

In another embodiment, the statistical significance of the response of a gene is characterized by a percentile ranking (see, e.g., U.S. Pat. No. 6,351,712, which is incorporated herein by reference in its entirety). In one embodiment, if a gene of interest is present in the top 1% of up or down regulations in a profile, the percentile rank of the gene in the profile is expressed as a p value=0.01. The percentile rank of a gene in k profiles is given by $$p = \prod_i p_i \quad (10)$$

where $p_i$ is the p value of the gene in the ith profile. In one embodiment, those genes whose p value in one or more profiles is less than a threshold are identified. In a preferred embodiment, genes whose p value is less than 0.01 in at least 50%, 70% or 90% of the response profiles are identified as commonly regulated genes.

5.2.3. Methods of Determining Candidate Gene(s) Responsible for a Phenotype

The invention provides methods for determining one or more candidate genes that may be responsible for a phenotypic feature of an eukaryotic cell. The methods involve identifying one or more genes that are commonly silenced by one or more siRNAs designed to silence a target gene in the cell, and associating the genes with a phenotypic feature that is associated with the perturbation of one or more siRNAs.

In one embodiment, an siRNA designed to silence a target gene is introduced into a cell. A phenotypic feature associated with the introduction of the siRNA is identified. Response profiles of the siRNA in the cell at a plurality of different time points after the introduction of the siRNA are measured. One or more non-target genes which are directly silenced by the siRNA are identified based on their kinetics using a method described in Section 5.2.2.1. The one or more non-target genes together with the target gene are identified as the candidate genes that may be responsible for the phenotypic feature.

In another embodiment, a plurality of different siRNAs designed to silence a target gene are introduced separately into cells of a cell type. A phenotypic feature commonly associated with the introduction of the siRNAs is identified. Response profiles comprising each profile for each of the siRNAs are measured. One or more genes, both target and non-target, which are commonly silenced by the plurality of siRNA are identified using a method described in Section 5.2.2.2. The one or more genes are identified as the candidate genes that may be responsible for the phenotypic feature.

In a preferred embodiment, a plurality of different siRNAs designed to silence a target gene are introduced together into cells of a cell type. A phenotypic feature associated with the introduction of the siRNAs is identified. A response profile for the plurality of the siRNAs is measured. The target gene is identified as the gene that may be responsible for the phenotypic feature. In a preferred embodiment, the plurality of different siRNAs comprises 3, 5, 9, 12, 15, 20, 50 or 100 different siRNAs. Preferably, the total concentration of the plurality of siRNAs is an optimal concentration for silencing the intended target gene. An optimal concentration is a concentration further increase of which does not increase the level of silencing substantially. In one embodiment, the optimal concentration is a concentration further increase of which does not increase the level of silencing by more than 5%, 10% or 20%. In a preferred embodiment, the composition of the plurality, including the number of different siRNAs in the plurality and the concentration of each different siRNA, is chosen such that the plurality of siRNAs causes less than 30%, 20%, 10% or 5%, 1%, 0.1% or 0.01% of silencing of any off-target genes. In another preferred embodiment, the plurality of different siRNAs comprises each siRNA in equal proportion. In still another preferred embodiment, the plurality of different siRNAs comprises each siRNA in proportions different from each other by less than 5%, 10%, 20% or 50%. In still another preferred embodiment, none of the siRNAs in the plurality of different siRNAs constitutes more than 90%, 80%, 70%, 50%, or 20% of the total siRNA concentration in the plurality. In other embodiments, each siRNA in the plurality has an concentration that is lower than the concentration when used individually. In a preferred embodiment, each of the plurality of different siRNAs has an concentration that is lower than the concentration of the siRNA that is effective to achieve at least 30%, 50%, 75%, 80% 85%, 90% or 95% silencing when used in the absence of other siRNAs or in the absence of other siRNAs designed to silence the gene. In another preferred embodiment, each of the plurality of different siRNAs has a concentration that causes less than 30%, 20%, 10% or 5% of silencing of the gene when used in the absence of other siRNAs or in the absence of other siRNAs designed to silence the gene. In a preferred embodiment, each siRNA has a concentration that causes less than 30%, 20%, 10% or 5% of silencing of the target gene when used alone, while the plurality of siRNAs causes at least 80% or 90% of silencing of the target gene.

5.2.4. Method of Determining Strand Preference in Gene Silencing

The invention provides a method of determining strand preference in gene silencing, i.e., which strand is more active. The method involves comparing alignments of sense vs. antisense strand of an siRNA with sequences in transcripts of a plurality of genes that are down-regulated by the siRNA, e.g., down-regulated signature genes identified by profiling (see Section 5.2). In one embodiment, the plurality of genes are off-target genes directly silenced by the siRNA. Such off-target genes can be identified by, e.g., examining silencing kinetics (see Section 5.2). In another embodiment, the plurality of genes comprises genes whose transcript levels are down-regulated by the siRNA as measured at a given time point. Thus, in this embodiment, the plurality of genes may comprise both directly silenced off-target genes and genes whose transcript levels decrease as a result of the loss of one or more proteins encoded by one or more other genes which are silenced by the siRNA.

In one embodiment, alignments identical to either the sense strand or the antisense strand are included. The inventors discovered that for the siRNAs whose down-regulation kinetics were examined, alignments to both sense strand and antisense strand were observed (see, e.g., Example 6.3., infra). These coordinately down-regulated off-target signature genes were seen to align with the siRNA regulating them in two ways: (1) central contiguous stretch of identity: 11 or more bases in the central portion of the siRNA duplex all identical to the off-target gene; or (2) 3'-based contiguous stretch of identity: 8 or more bases terminating within 3 bases of the 3' end of the siRNA duplex all identical to the off-target gene.

It is inferred that for siRNAs where alignments are identical to the sense strand, the antisense strand is causing both on- and off-target regulation; for siRNAs where alignments are identical to the antisense strand, the sense strand is causing off-target regulation in addition to the activity of the antisense strand.

In one embodiment, single time point signatures are assessed by polling all or a portion of all signature genes, i.e., genes down-regulated, for greater extent of alignment with one siRNA strand vs. the other siRNA strand (the "polling method"). In a preferred embodiment, the signature gene sequences are aligned with both strands of the siRNA. Alignments to each strand are examined for the longest contiguous stretch of identity. The lengths of these stretches of identity are compared. The gene is considered to have voted for the strand to which it has the longer contiguous stretch of identity. In one embodiment, the vote is weighted by the number of bases in the longer of the two stretches of identity in excess in the shorter of the two stretches of identity. Thus, an siRNA having a greater difference in the length of the two stretches of sequence identity contributes more veteS votes. For example, an siRNA having a 15-base stretch of identity in one strand and a 5-base stretch of identity in another strand weighs more heavily than an siRNA having an 8-base stretch of identify in one strand and a 7-base stretch of identity in the other strand. Therefore, a vote is a base in a contiguous stretch of identity in excess in one strand. Total votes represent the total excess length in contiguous identity for the winning strand in all the genes where it dominated.

In one embodiment, the background of the extent of alignment with the strands of an siRNA (background strand preference) is determined by examining alignments of both strands of the siRNA to a larger set of genes, e.g., all genes whose transcript levels are assayed for the siRNA. The background strand preference is determined by letting the strands vote as described above, and calculating the average excess weight per gene for each strand of the siRNA. In a preferred embodiment, the transcript levels are assayed using a DNA microarray. In such an embodiment, all genes assayed, e.g., all genes included in a siRNA profile, can be used. Preferably, more than 5, more than 10, more than 100, more than 1000, more than 10,000, more than 25,000, more than 50,000, or more than 100,000 transcript levels are measured for the response profile of an siRNA and used.

In another embodiment, the polling method is used to evaluate and determine the strand preference of an siRNA by examining a plurality of genes that are down-regulated by the siRNA with the same kinetics as the intended target gene. Such genes can be identified as described in Section 5.2. Strand preference is assessed by polling such signature genes for greater extent of alignment with one siRNA strand vs. the other siRNA strand.

In another embodiment, single time point signatures are assessed by comparison of signature gene alignments with the 3'-biased model (the 3'-biased method) developed from alignments of siRNAs with genes they down-regulated with the same kinetics as the intended target gene (see Section 5.2). In one embodiment, the signature genes are analyzed to determine the fraction matching the 3'-biased model of off-target gene alignment, i.e., 3'-based contiguous stretch of identity of 8 or more bases terminating within 3 bases of the 3' end of the siRNA duplex all identical to the off-target gene. The signature gene sequences are aligned with both strands of the siRNA. Alignments to each strand are examined for contiguous stretches of identity. Alignments were tallied if they: a) have a contiguous stretch of identity of at least 7 bases; and b) terminated within 3 bases of the 3' end of the particular strand.

In one embodiment, the tally of alignments meeting the above criteria a) and b) with identity to the sense strand and with identity to the antisense strand is compared by calculating a SLR score according to equation $$SLR = \log(\text{sense-identical-tally}/\text{antisense-identical-tally}) \quad (11)$$

The significance of the SLR can be assessed by comparing the sense-identical and antisense-identical tallies for the signatures with the sense-identical and antisense-identical tallies for all genes whose transcript levels are assayed for the siRNA. In a preferred embodiment, the transcript levels are assayed using a DNA microarray. In such an embodiment, all genes assayed, e.g., all genes included in an siRNA profile, can be used. Preferably, more than 5, more than 10, more than 100, more than 1000, more than 10,000, more than 25,000, more than 50,000, or more than 100,000 transcript levels are measured for the response profile of an siRNA and used. In one embodiment, significance is calculated from the hypergeometric distribution according to the equation $$h(x, n, M, N) = \frac{\binom{M}{x}\binom{N-M}{n-x}}{\binom{N}{n}} \quad (12)$$

where:
x, Sample-selection=signature tally for one strand
n, Sample-total=signature tallies for both strands
M, Parent-selection=chip tally for the same strand
N, Parent-total=chip tallies for both strands.

As the hypergeometric distribution is not symmetric, both tails of both the sense-strand and antisense-strand selection hypergeometric distributions are used. The two tails corresponding to sense-identical excess are averaged to give the p-value for excess sense identity, both tails corresponding to antisense-identical excess are averaged to give the p-value for excess antisense identity.

In another embodiment, the 3'-biased method is used to evaluate and determine the strand preference of an siRNA by examining a plurality of genes that are down-regulated by the siRNA with the same kinetics as the intended target gene. Such genes can be identified as described in Section 5.2. Strand preference is assessed by tallying such signature genes for alignment with one siRNA strand vs. the other siRNA strand.

The pooling method in particular was seen to be effective for analysis of 12-hour, 24-hour and 48-hour signatures (see Example 3, infra). 24-hour signatures generally gave the most significant results. In effect, the utility of a significant fraction of the signature, or of the signature as a whole, for determination of the strand preference of an siRNA implies that the direct effect of the siRNA on gene expression in the cell is represented by a significant fraction of the signature genes. For example, both methods estimate that about 35-40% of a 12 hour IGF1R-73 signature is relevant for estimation of its strand bias, i.e. about 12 genes. 35-40% of a 24 hour IGF1R-73 signature is also relevant, i.e. about 80 genes.

In still another embodiment, the invention provides a method for predicting strand preference and/or the efficacy and specificity of siRNAs based on position specific base composition of the siRNAs. The inventors have discovered that an siRNA whose base composition PSSM score (see U.S. Provisional Application No. 60/515,180, filed on Oct. 27, 2003, by Jackson et al., which is incorporated herein by reference in its entirety) is greater than the base composition PSSM (G/C PSSM) score of its reverse complement is predicted to have an antisense strand that is more active than its sense strand. In contrast, an siRNA whose base composition PSSM score is less than the base composition PSSM score of its reverse complement is predicted to have a sense strand that is more active than its antisense strand.

It has been shown that increased efficacy corresponds to greater antisense strand activity and lesser sense strand activity. The inventors have discovered that base composition PSSMs can be used to distinguish siRNAs with strong sense strands as bad siRNAs from siRNAs with weak sense strands as good siRNAs. The reverse complements of bad siRNAs were seen to be even more different from the bad siRNAs themselves than are good siRNAs. On the average, the reverse complements of bad siRNAs had even stronger G/C content at the 5' end than the good siRNAs did and were similar in G/C content to good siRNAs at the 3' end. In contrast, the reverse complements of good siRNAs were seen to be substantially more similar to bad siRNAs than the good siRNAs were. On the average, the reverse complements of good siRNAs hardly differed from bad siRNAs in G/C content at the 5' end and were only slightly less G/C rich than bad siRNAs at the 3' end. These results indicate that the G/C PSSMs are distinguishing siRNAs with strong sense strands as bad siRNAs from siRNAs with weak sense strands as good siRNAs.

FIG. 13A shows the difference between the mean G/C content of the reverse complements of bad siRNAs with the mean G/C content of the bad siRNAs themselves, within the 19mer siRNA duplex region. The difference between the mean G/C content of good and bad siRNAs is shown for comparison. The curves are smoothed over a window of 5 (or portion of a window of 5, at the edges of the sequence).

FIG. 13B shows the difference between the mean G/C content of the reverse complements of good siRNAs with the mean G/C content of bad siRNAs, within the 19mer siRNA duplex region. The difference between the mean G/C content of good and bad siRNAs is shown for comparison. The curves are smoothed over a window of 5 (or portion of a window of 5, at the edges of the sequence).

In FIG. 14, siRNAs were binned by measured silencing efficacy, and the frequency of sense-active calls by the 3'-biased method and G/C PSSM method was compared. Although these techniques are based on different analyses, the agreement is quite good. Both show that a higher proportion of low-silencing siRNAs vs. high-silencing siRNAs are predicted to be sense active. The correlation coefficient for (siRNA G/C PSSM score–reverse complement G/C PSSM score) vs. $\log_{10}$(sense-identity score/antisense-identity score) is 0.59 for the set of 61 siRNAs binned in FIG. 14.

Thus, in one embodiment, invention provides a method for predicting strand preference of siRNAs based on position specific base composition of the siRNAs. In one embodiment, the method comprises evaluating the strand preference of an siRNA in gene silencing by comparing the base compositions of the sense and the antisense strands of the siRNA. In another embodiment, the method comprises evaluating the strand preference of an siRNA in gene silencing by comparing the base compositions of the sense and the reverse complement of the target sequence of the siRNA.

In one embodiment, the antisense strand of an siRNA or the reverse complement of a target sequence of the siRNA in a transcript are compared with the sense strand using a PSSM approach (see U.S. Provisional Application No. 60/515,180, filed on Oct. 27, 2003, by Jackson et al., which is incorporated herein by reference in its entirety). An siRNA and its reverse complement are scored using a PSSM based on a smoothed G/C content difference between good and bad siRNAs within the duplex region as the weight matrix. In one embodiment, a base composition weight matrix as described by FIG. 13A is used as the weight matrix. In a preferred embodiment, the PSSM score of each strand can be calculated as the dot product of the siRNA strand G/C content with the G/C content difference matrix (as the score calculation method of curve model PSSMs described in U.S. Provisional Application No. 60/515,180). In one embodiment, an siRNA is identified as sense-active if its reverse complement PSSM score exceeded its own PSSM score.

In another embodiment, the 3-biased method is used in conjunction with the PSSM score to determine the strand preference of an siRNA. In such an embodiment, an siRNA is identified as sense-active by the 3'-biased method of strand preference determination if the antisense-identical score exceeded the sense-identical score.

The method based on comparison of G/C PSSMs of siRNAs and their reverse complements for prediction of strand bias was tested by comparison with estimation of strand bias from siRNA expression profiles by the 3'-biased method.

The invention also provides a method for improving the silencing specificity of an siRNA. The method involves determining strand preference of the siRNA in off-target silencing. If the siRNA is determined as having sense strand preference, modifying the sense strand such that the sense strand activity is reduced or eliminated. In one embodiment, the modification is achieved by introducing two 2'-o-methyl substitutions in the sense strand.

5.3. Methods and Compositions of Gene Silencing

The invention provides methods and compositions for gene silencing using siRNAs having only partial sequence homology to a target gene. In a preferred embodiment, the invention provides methods and composition for silencing a target gene using an siRNA that comprises a sense strand or antisense strand contiguous nucleotide sequence of 11-18 nucleotides that is identical to a sequence of a transcript of the target gene but the siRNA does not have full length homology to any sequences in the transcript. Preferably, the contiguous nucleotide sequence is in the central region of the siRNA molecules. A contiguous nucleotide sequence in the central region of an siRNA can be any continuous stretch of nucleotide sequence in the siRNA which does not begin at the 3' end. For example, a contiguous nucleotide sequence of 11 nucleotides can be the nucleotide sequence 2-12, 3-13, 4-14, 5-15, 6-16, 7-17, 8-18, or 9-19. In preferred embodiments, the contiguous nucleotide sequence is 11-16, 11-15, 14-15, 11, 12, or 13 nucleotides in length.

In another preferred embodiment, the invention provides methods and compositions for silencing a target gene using an siRNA that comprises a 3' sense strand or antisense strand contiguous nucleotide sequence of 9-18 nucleotides which is identical to a sequence of a transcript of the target gene but which siRNA does not have full length sequence identity to any contiguous sequences in the transcript. In this application, a 3' 9-18 nucleotide sequence is a continuous stretch of nucleotides that begins at the first paired base, i.e., it does not comprise the two base 3' overhang. Thus, when it is stated that a particular nucleotide sequence is at the 3' end of the siRNA, the 2 base overhang is not considered. In preferred embodiments, the contiguous nucleotide sequence is 9-16, 9-15, 9-12, 11, 10, or 9 nucleotides in length.

In another preferred embodiment, a plurality of different siRNAs designed to silence a target gene are introduced together into cells of a cell type. Each of the different siRNAs comprises a different sequence. In a preferred embodiment, the plurality of different siRNAs comprises 3, 5, 9, 12, 15, 20, 50 or 100 different siRNAs. Preferably, the total concentration of the plurality of siRNAs is an optimal concentration for silencing the intended target gene. An optimal concentration is a concentration further increase of which does not increase the level of silencing substantially. In one embodiment, the optimal concentration is a concentration further increase of which does not increase the level of silencing by more than 5%, 10% or 20%. In a preferred embodiment, the composition of the plurality, including the number of different siRNAs in the plurality and the concentration of each different siRNA, is chosen such that the plurality of siRNAs causes less than 30%, 20%, 10% or 5%, 1%, 0.1% or 0.01% of silencing of any off-target genes. In another preferred embodiment, the plurality of different siRNAs comprises each siRNA in equal proportion. In still another preferred embodiment, the plurality of different siRNAs comprises each siRNA in proportions different from each other by less than 5%, 10%, 20% or 50%. In still another preferred embodiment, none of the siRNAs in the plurality of different siRNAs constitutes more than 90%, 80%, 70%, 50%, or 20% of the total siRNA concentration in the plurality. In other embodiments, each siRNA in the plurality has an concentration that is lower than the concentration when used individually. In a preferred embodiment, each of the plurality of different siRNAs has a concentration that is lower than the concentration of the siRNA that is effective to achieve at least 30%, 50%, 75%, 80% 85%, 90% or 95% silencing when used in the absence of other siRNAs or in the absence of other siRNAs designed to silence the gene. In another preferred embodiment, each of the plurality of different siRNAs has a concentration that causes less than 30%, 20%, 10% or 5% of silencing of the gene when used in the absence of other siRNAs or in the absence of other siRNAs designed to silence the gene. In a preferred embodiment, each siRNA has a concentration that causes less than 30%, 20%, 10% or 5% of silencing of the target gene when used alone, while the plurality of siRNAs causes at least 80% or 90% of silencing of the target gene.

In specific embodiments, the invention provides methods and compositions for silencing transcripts of KPNB3, RAP2A, FLJ20291, RRAD, RPA2, DKFZp564J157, AF093680, and genes corresponding to two EST contigs, Contig53709_RC and Contig56528_RC, using siRNAs having only partial sequence homology to a sequence in these gene. The siRNAs used for silencing these genes are MAPK14-1 through MAPK14-8 as shown in Table 1. Sequence alignment demonstrated that these genes could be divided into two subgroups. One subgroup, consisting of three genes, contained a core of 14 to 15 nucleotides of similarity encompassing the central region of the siRNA sequence. The second subgroup contained a smaller core of similarity encompassing the nine nucleotides at the 3' end of the siRNA sense strand sequence. This is in contrast to transcripts in kinetic groups 3-5, which displayed only short stretches (<6-8 nucleotides) of similarity distributed randomly throughout the siRNA sequence. Thus, the bias for a core of sequence similarity encompassing the 3' end of the siRNA is unique to the rapidly silenced transcripts. To test this possibility, systematically substitution the nucleotide at each position of the siRNA sequence were carried out and the effect of the altered sequence on the expression signature were determined (see FIG. 7). The representative results are presented in FIG. 5B. A single nucleotide substitution at position 4 dramatically decreased silencing of MAPK14, and abolished silencing of the three off-target genes in subgroup 1 that contain similarity to MAPK14 at this position. However, silencing was not abolished for the six off-target genes in subgroup 2 that do not contain similarity to MAPK14 in this region. A single nucleotide substitution at position 5 reduced, but did not eliminate, MAPK14 silencing, and abolished silencing of the three genes in subgroup 1 that contained similarity to MAPK14 in this region. The expression levels of the six off-target genes that do not share similarity in this region were unaffected by this mismatch. These results confirm that silencing of the off-target genes is independent of loss of MAPK14 expression. A single nucleotide substitution at position 15 also reduced MAPK14 silencing, and abolished silencing of all nine off-target genes. The effect of the position 15 mismatch was more dramatic, presumably because all nine transcripts contain similarity to MAPK14 in this region. Collectively, these results confirm that the sequence similarity of these transcripts to siRNA MAPK14-1 through 8 accounts for their silencing by the MAPK14 siRNA.

As further evidence that the observed off-target gene silencing is based on sequence similarity and not a consequence of reduced MAPK14 expression, a different siRNA duplex with a different oligonucleotide sequence (FIG. 5A) was tested. This second siRNA (MAPK14-2) silenced MAPK14 but not any of the Group 2 transcripts, which are not similar to the new siRNA sequence (FIG. 5B).

In another specific embodiment, methods and compositions for silencing MAPK14 using siRNAs having only partial sequence homology to sequences in MAPK14 gene are provided. siRNAs for two transcripts, KPNB3 and FLJ20291 (see, FIG. 4A), silenced the expression of MAPK14 in addition to their intended targets (FIG. 5C). The KPNB3 siRNA shares 14 contiguous nucleotides, and a total of 15 nucleotides, of identity with MAPK14. The FLJ20291 siRNA shares only 11 contiguous nucleotides, and a total of 15 nucleotides, of identity with MAPK14. Thus as few as 11 contiguous nucleotides of sequence identity is sufficient to direct silencing of non-targeted transcripts.

The invention also provides a method for treating a disease or other undesirable condition in an animal, such as a mammal, by reducing the expression of one or more genes in cells of an organ or tissue suffered from the disease or the undesirable condition. The method comprises administering to the animal an siRNA of the invention, e.g., an siRNA that comprises a sense or antisense strand central contiguous nucleotide sequence of 11-15, 14-15, 11, 12, or 13 nucleotides or an siRNA that comprises a 3' sense strand or antisense strand contiguous nucleotide sequence of 9-15, 9-12, 11, 10, or 9 nucleotides. The siRNA can be administered using any method known in the art. Preferably, the methods described in Section 5.5, infra, are used for in vivo delivery of siRNA. In one embodiment, the method is used for treating a disease or other undesirable condition in a human.

In a preferred embodiment, the invention provides a method for treating a disease or other undesirable condition in an animal, such as a mammal, by administering to the animal a plurality of different siRNAs designed to silence a target gene whose down regulation is beneficial for treating the disease. In a preferred embodiment, the plurality of different siRNAs comprises 3, 5, 9, 12, 15, 20, 50 or 100 different siRNAs. Preferably, the total concentration of the plurality of siRNAs is an optimal concentration for silencing the intended target gene. An optimal concentration is a concentration further increase of which does not increase the level of silencing substantially. In one embodiment, the optimal concentration is a concentration further increase of which does not increase the level of silencing by more than 5%, 10% or 20%. In a preferred embodiment, the composition of the plurality, including the number of different siRNAs in the plurality and the concentration of each different siRNA, is chosen such that the plurality of siRNAs causes less than 30%, 20%, 10% or 5%, 1%, 0.1% or 0.01% of silencing of any off-target genes. In another preferred embodiment, the plurality of different siRNAs comprises each siRNA in equal proportion. In still another preferred embodiment, the plurality of different siRNAs comprises each siRNA in proportions different from each other by less than 5%, 10%, 20% or 50%. In still another preferred embodiment, none of the siRNAs in the plurality of different siRNAs constitutes more than 90%, 80%, 70%, 50%, or 20% of the total siRNA concentration in the plurality. In other embodiments, each siRNA in the plurality has an concentration that is lower than the concentration when used individually. In a preferred embodiment, each of the plurality of different siRNAs has an concentration that is lower than the concentration of the siRNA that is effective to achieve at least 30%, 50%, 75%, 80% 85%, 90% or 95% silencing when used in the absence of other siRNAs or in the absence of other siRNAs designed to silence the gene. In another preferred embodiment, each of the plurality of different siRNAs has a concentration that causes less than 30%, 20%, 10% or 5% of silencing of the gene when used in the absence of other siRNAs or in the absence of other siRNAs designed to silence the gene. In a preferred embodiment, each siRNA has a concentration that causes less than 30%, 20%, 10% or 5% of silencing of the target gene when used alone, while the plurality of siRNAs causes at least 80% or 90% of silencing of the target gene.

5.4. Methods of Designing Short Interfering RNAS for Gene Silencing

The invention provides methods of designing siRNAs for silencing one or more genes.

In one embodiment, the invention provides methods for designing the sequences of an siRNA which targets a gene but does not target one or more chosen non-target genes. In a preferred embodiment, the sequence of the siRNA is selected such that the sense strand or antisense strand sequence of the central region is not identical to any sequences in the transcripts of the one or more chosen non-target genes. In a preferred embodiment, the central region comprises about 10-14 nucleotides. In another preferred embodiment, the sequence of the central region of the siRNA has at least 1, 2, 3 or 5 mismatches as compared to any sequences in the one or more non-target genes.

In another preferred embodiment, the sequence of the siRNA is selected such that the 3' sense strand or antisense strand sequence is not identical to any sequences in the transcripts of the one or more chosen non-target genes. In a preferred embodiment, the 3' sequence comprises about 9 nucleotides. In another preferred embodiment, the 3' sequence of the siRNA has at least 1, 2, 3 or 5 mismatches as compared to any sequences in the one or more non-target genes.

In another preferred embodiment, the invention provides a method for designing the sequence of an siRNA which targets a plurality of different genes which share a common nucleotide sequence of 9-18 nucleotides. The method comprises selecting a small interfering RNA (siRNA) which comprises (i) a sense strand or antisense strand central contiguous nucleotide sequence of 11-18 nucleotides that comprises said common sequence, and/or (ii) a 3' sense strand or antisense strand contiguous nucleotide sequence of 9 nucleotides that is identical to a sequence in said common sequence. In preferred embodiments, the central contiguous nucleotide sequence is 11-15, 14-15, 11, 12, or 13 nucleotides in length. In other preferred embodiments, the 3' contiguous nucleotide sequence is 9-15, 9-12, 11, 10, or 9 nucleotides in length.

Any known methods for designing nucleic acid sequences can be used for this purpose.

In still another preferred embodiment, the invention provides a method for designing an siRNA for silencing a target gene. The method comprises generating a plurality of different siRNAs, each designed to target a different sequence in a transcript of the target gene. For each of the plurality of siRNAs, a response profile is then determined. One or more siRNAs that have a desired response profile are then identified. In one embodiment, one or more siRNAs that have the least number of off-target genes are identified and selected. In another embodiment, one or more siRNAs that do not affect one or more chosen genes, e.g., causing less than a 50%, 25%, 10%, or 5% reduction in the transcript levels of one or more chosen genes, are identified and selected. In preferred embodiments, the plurality of different siRNAs comprises siRNAs having sequences tiled across a part of or the entire coding sequence of the target gene, i.e., having successive overlapping sequences tiled across a part of or the entire coding sequence. In one embodiment, the plurality of different siRNAs comprises siRNAs having sequences tiled across the entire coding sequence of the target gene at an interval of 20, 15, 10, 5, 2 or 1 base. In another embodiment, the plurality of different siRNAs comprises siRNAs having sequences tiled across sequences of all known or predicted exons and exon variants of the target gene at an interval of 20, 15, 10, 5, 2 or 1 base.

The siRNAs selected can be further evaluated for their efficacy and or specificity in silencing the target gene. In one embodiment, the siRNA that demonstrates the highest reduction of target transcript level is selected. In another embodiment, when a specific level of reduction of the transcript level of the target gene, e.g., at least 5%, 10%, 25%, 50%, 75%, 90% or 95% of reduction of the transcript level of the target gene, is desired, the siRNA that demonstrates such a desired reduction of the transcript level is selected. In a preferred embodiment, the method as described in U.S. Provisional Application No. 60/515,180, filed on Oct. 27, 2003, by Jackson et al., which is incorporated herein by reference in its entirety, is used for evaluating the efficacy and/or specificity of siRNAs in gene silencing.

5.5. Methods for Performing RNA Interference

Any method known in the art can be used for carrying out RNA interference. In one embodiment, gene silencing is induced by presenting the cell with the siRNA, mimicking the product of Dicer cleavage (see, e.g., Elbashir et al., 2001, *Nature* 411, 494-498; Elbashir et al., 2001, *Genes Dev.* 15, 188-200, all of which are incorporated by reference herein in their entirety). Synthetic siRNA duplexes maintain the ability to associate with RISC and direct silencing of mRNA transcripts, thus providing researchers with a powerful tool for gene silencing in mammalian cells. siRNAs can be chemically synthesized, or derived from cleavage of double-stranded RNA by recombinant Dicer.

Another method to introduce a double stranded DNA (dsRNA) for gene silencing is shRNA, for short hairpin RNA (see, e.g., Paddison et al., 2002, *Genes Dev.* 16, 948-958; Brummelkamp et al., 2002, *Science* 296, 550-553; Sui, G. et al. 2002, *Proc. Natl. Acad. Sci. USA* 99, 5515-5520, all of which are incorporated by reference herein in their entirety). In this method, a desired siRNA sequence is expressed from a plasmid (or virus) as an inverted repeat with an intervening loop sequence to form a hairpin structure. The resulting RNA transcript containing the hairpin is subsequently processed by Dicer to produce siRNAs for silencing. Plasmid-based shRNAs can be expressed stably in cells, allowing long-term gene silencing in cells both in vitro and in vivo, e.g., in animals (see, McCaffrey et al. 2002, *Nature* 418, 38-39; Xia et al., 2002, *Nat. Biotech.* 20, 1006-1010; Lewis et al., 2002, *Nat. Genetics* 32, 107-108; Rubinson et al., 2003, *Nat. Genetics*

33, 401-406; Tiscornia et al., 2003, *Proc. Natl. Acad. Sci. USA* 100, 1844-1848, all of which are incorporated by reference herein in their entirety).

In yet another method, siRNAs can be delivered to an organ or tissue in an animal, such a human, in vivo (see, e.g., Song et al. 2003, *Nat. Medicine* 9, 347-351; Sorensen et al., 2003, *J. Mol. Biol.* 327, 761-766; Lewis et al., 2002, *Nat. Genetics* 32, 107-108, all of which are incorporated by reference herein in their entirety). In this method, a solution of siRNA is injected intravenously into the animal. The siRNA can then reach an organ or tissue of interest and effectively reduce the expression of the target gene in the organ or tissue of the animal.

5.6. Methods for Determining Biological State and Biological Response

This invention provides methods for determining response profiles of siRNAs. The measured responses can be measurements of cellular constituents in a cell or organism or responses of a cell or organism to a perturbation by an siRNA. The cell sample can be of any organism in which RNA interference can occur, e.g., eukaryote, mammal, primate, human, non-human animal such as a dog, cat, horse, cow, mouse, rat, *Drosophila, C. elegans*, etc., plant such as rice, wheat, bean, tobacco, etc., and fungi. The cell sample can be from a diseased or healthy organism, or an organism predisposed to disease. The cell sample can be of a particular tissue type or development stage and subjected to a particular siRNA perturbation. This section and its subsections provide some exemplary methods for obtaining response profiles of cell samples. One of skill in the art would appreciate that this invention is not limited to the following specific methods for measuring the expression profiles and responses of a biological system.

5.6.1. Transcript Assays Using Microarrays

This invention is particularly useful for the determination of the expression state or the transcriptional state of a cell or cell type or any other cell sample by monitoring expression profiles. One aspect of the invention provides polynucleotide probe arrays for simultaneous determination of the expression levels of a plurality of genes and methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundance ratios.

Preferably, measurement of the expression profile is made by hybridization to transcript arrays, which are described in this subsection.

In a preferred embodiment, the present invention makes use of "transcript arrays" or "profiling arrays". Transcript arrays can be employed for analyzing the expression profile in a cell sample and especially for measuring the expression profile of a cell sample of a particular tissue type or developmental state or exposed to an siRNA of interest or to perturbations to a biological pathway of interest. In another embodiment, the cell sample can be from a patient, e.g., a diseased cell sample, and preferably can be compared to a healthy cell sample.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g. nucleic acid hybridization) conditions. The microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to a nucleotide sequence in a single gene from a cell or organism (e.g., to gene of a specific mRNA or a specific cDNA derived therefrom).

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface). In some embodiments of the invention, the arrays are ordered arrays.

Preferably, the density of probes on a microarray or a set of microarrays is about 100 different (i.e., non-identical) probes per 1 cm$^2$ or higher. More preferably, a microarray used in the methods of the invention will have at least 550 probes per 1 cm$^2$, at least 1,000 probes per 1 cm$^2$, at least 1,500 probes per 1 cm$^2$ or at least 2,000 probes per 1 cm$^2$. In a particularly preferred embodiment, the microarray is a high density array, preferably having a density of at least about 2,500 different probes per 1 cm$^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to a gene.

In some embodiments of the present invention, a gene or an exon in a gene is represented in the profiling arrays by a set of binding sites comprising probes with different polynucleotides that are complementary to different coding sequence segments of the gene or an exon of the gene. Such polynucleotides are preferably of the length of 15 to 200 bases, more preferably of the length of 20 to 100 bases, most preferably 40-60 bases. It will be understood that each probe sequence may also comprise linker sequences in addition to the sequence that is complementary to its target sequence. As used herein, a linker sequence refers to a sequence between the sequence that is complementary to its target sequence and the surface of support. For example, in preferred embodiments the profiling arrays of the invention comprise one probe specific to each target gene or exon. However, if desired, the profiling arrays may contain at least 2, 5, 10, 100, 1000 probes specific to some target genes or exons. For example, the array may contain probes tiled across the sequence of the longest mRNA isoform of a gene at single base steps.

In preferred embodiments, cDNAs from cell samples from two different conditions are hybridized to the binding sites of the microarray using a two-color protocol. In the case of siRNA responses one cell sample is exposed to the siRNA and another cell sample of the same type is not exposed to the siRNA. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with an siRNA (or exposed to a pathway perturbation) is synthesized using a fluorescein-labeled dNTP, and cDNA from a second cell, not siRNA-exposed, is synthesized using a rhodamine-labeled dNTP. When the two cDNAs are mixed and hybridized to the microarray, the relative intensity of signal from each cDNA set is determined for each site on the array, and any relative difference in abundance of a particular gene detected.

In the example described above, the cDNA from the siRNA-treated (or pathway perturbed) cell will fluoresce green when the fluorophore is stimulated and the cDNA from the untreated cell will fluoresce red. As a result, when the siRNA treatment has no effect, either directly or indirectly, on the transcription and/or post-transcriptional splicing of a particular gene in a cell, the gene and/or exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the siRNA-exposed cell is treated with a siRNA that, directly or indirectly, change the transcription and/or post-transcriptional splicing of a particular gene in the cell, the gene and/or exon expression pattern as represented by ratio of green to red fluorescence for each gene or exon binding site will change. When the siRNA increases the prevalence of an mRNA, the ratios for each gene or exon expressed in the mRNA will increase, whereas when the siRNA decreases the prevalence of an mRNA, the ratio for each gene or exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of genes or exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular gene or exon in, e.g., an siRNA-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual,* 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.6.2. Preparing Probes for Microarrays

As noted above, the "probe" to which a particular polynucleotide molecule, such an gene or exon, specifically hybridizes according to the invention is a complementary polynucleotide sequence. Preferably one or more probes are selected for each target gene or exon. For example, when a minimum number of probes are to be used for the detection of a gene or exon, the probes normally comprise nucleotide sequences greater than about 40 bases in length. Alternatively, when a large set of redundant probes is to be used for a gene or exon, the probes normally comprise nucleotide sequences of about 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of a gene or an exon of a gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of gene or exon segments from genomic DNA, cDNA (e.g., by RT-PCR), or cloned sequences. PCR primers are preferably chosen based on known sequence of the genes or exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

5.6.3. Attaching Probes to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per gene or exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al, 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111-123).

5.6.4. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsC1 centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891, 636, 5,716,785; 5,545,522 and 6,132,997; see also, U.S. patent application Ser. No. 09/411,074, filed Oct. 4, 1999 by Linsley and Schelter and PCT publication No. WO 02/44399). Both oligo-dT primers (U.S. Pat. Nos. 5,545,522 and 6,132,997) or random primers (PCT publication No. WO 02/44399) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.6.5. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65 EC for four hours, followed by washes at 25 EC in low stringency wash buffer (1×SSC plus 0.2% SDS), followed by 10 minutes at 25 EC in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.6.6. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to a gene or an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced by from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of siRNA responses one cell sample is exposed to an siRNA and another cell sample of the same type is not exposed to the siRNA. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with an siRNA (or exposed to a pathway perturbation) is synthesized using a fluorescein-labeled dNTP, and cDNA from a second cell, not siRNA-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the siRNA-treated (or pathway perturbed) cell will fluoresce green when the fluorophore is stimulated and the cDNA from the untreated cell will fluoresce red. As a result, when the siRNA treatment has no effect, either directly or indirectly, on the transcription and/or post-transcriptional splicing of a particular gene in a cell, the gene or exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the siRNA-exposed cell is treated with an siRNA that, directly or indirectly, changes the transcription and/or post-transcriptional splicing of a particular gene in the cell, the gene or exon expression pattern as represented by ratio of green to red fluorescence for each gene or exon binding site will change. When the siRNA increases the prevalence of an mRNA, the ratios for each gene or exon expressed in the mRNA will increase, whereas when the siRNA decreases the prevalence of an mRNA, the ratio for each gene or exon expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular gene or exon in, e.g., a siRNA-treated or pathway-perturbed cell and an untreated cell.

In other preferred embodiments, single-channel detection methods, e.g., using one-color fluorescence labeling, are used (see U.S. provisional patent application Ser. No. 60/227,966, filed on Aug. 25, 2000). In this embodiment, arrays comprising reverse-complement (RC) probes are designed and produced. Because a reverse complement of a DNA sequence has sequence complexity that is equivalent to the corresponding forward-strand (FS) probe that is complementary to a target sequence with respect to a variety of measures (e.g., measures such as GC content and GC trend are invariant under the reverse complement), a RC probe is used to as a control probe for determination of level of non-specific cross hybridization to the corresponding FS probe. The significance of the FS probe intensity of a target sequence is determined by comparing the raw intensity measurement for the FS probe and the corresponding raw intensity measurement for the RC probe in conjunction with the respective measurement errors. In a preferred embodiment, a gene or exon is called present if the intensity difference between the FS probe and the corresponding RC probe is significant. More preferably, a gene or exon is called present if the FS probe intensity is also significantly above background level. Single-channel detection methods can be used in conjunction with multi-color labeling. In one embodiment, a plurality of different samples, each labeled with a different color, is hybridized to an array. Differences between FS and RC probes for each color are used to determine the level of hybridization of the corresponding sample.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g, Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by siRNA transfection, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.6.7. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci.* USA 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, *Science* 270:484-487).

5.7. Measurement of Other Aspects of the Biological State

In various embodiments of the present invention, aspects of the biological state other than the transcriptional state, such as the translational state, the activity state, or mixed aspects can be measured to produce the measured signals to be analyzed according to the invention. Thus, in such embodiments, gene expression data may include translational state measurements or even protein expression measurements. In fact, in some embodiments, rather than using gene expression interaction maps based on gene expression, protein expression interaction maps based on protein expression maps are used. Details of embodiments in which aspects of the biological state other than the transcriptional state are described in this section.

5.7.1. Embodiments Based on Translational State Measurements

Measurement of the translational state may be performed according to several methods. For example, whole genome monitoring of protein (i.e., the "proteome," Goffeau et al., 1996, *Science* 274:546-567; Aebersold et al., 1999, *Nature Biotechnology* 10:994-999) can be carried out by constructing a microarray in which binding sites comprise immobilized, preferably monoclonal, antibodies specific to a plurality of protein species encoded by the cell genome (see, e.g., Zhu et al., 2001, *Science* 293:2101-2105; MacBeath et al., 2000, *Science* 289:1760-63; de Wildt et al., 2000, *Nature Biotechnology* 18:989-994). Preferably, antibodies are present for a substantial fraction of the encoded proteins, or at least for those proteins relevant to the action of an siRNA of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated and measured by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of proteins: A Practical Approach*, IRL Press, New York; Shevchenko et al., 1996, *Proc. Natl. Acad. Sci. USA* 93:1440-1445; Sagliocco et al., 1996, *Yeast* 12:1519-1533; Lander, 1996, *Science* 274:536-539; and Beaumont et al., Life Science News 7, 2001, Amersham Pharmacia Biotech. The resulting electropherograms can be analyzed by numerous techniques, including mass spectrometric techniques, Western blotting and immunoblot analysis using polyclonal and monoclonal antibodies, and internal and N-terminal microsequencing. Using these techniques, it is possible to identify a substantial fraction of all the proteins produced under given physiological conditions, including in cells (e.g., in yeast) exposed to an siRNA, or in cells modified by, e.g., deletion or over-expression of a specific gene.

5.7.2. Embodiments Based on Other Aspects of the Biological State

Even though methods of this invention are illustrated by embodiments involving gene expression, the methods of the invention are applicable to any cellular constituent that can be monitored. In particular, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

5.8. Implementation Systems and Methods

The analytical methods of the present invention can preferably be implemented using a computer system, such as the computer system described in this section, according to the following programs and methods. Such a computer system can also preferably store and manipulate measured signals obtained in various experiments that can be used by a computer system implemented with the analytical methods of this invention. Accordingly, such computer systems are also considered part of the present invention.

Figure 8:
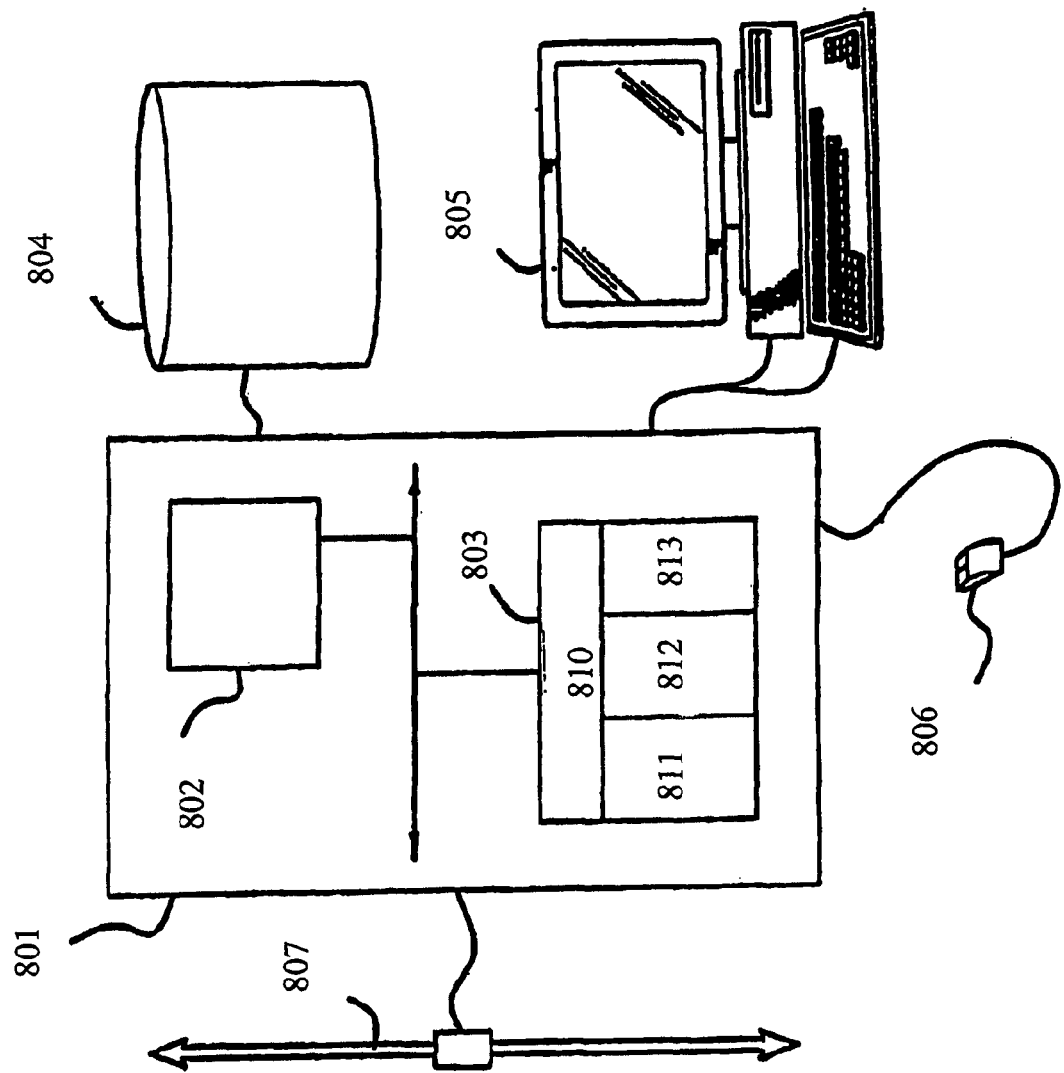
FIG. 8 illustrates an exemplary embodiment of a computer system useful for implementing the methods of the present invention.
Figure 9:
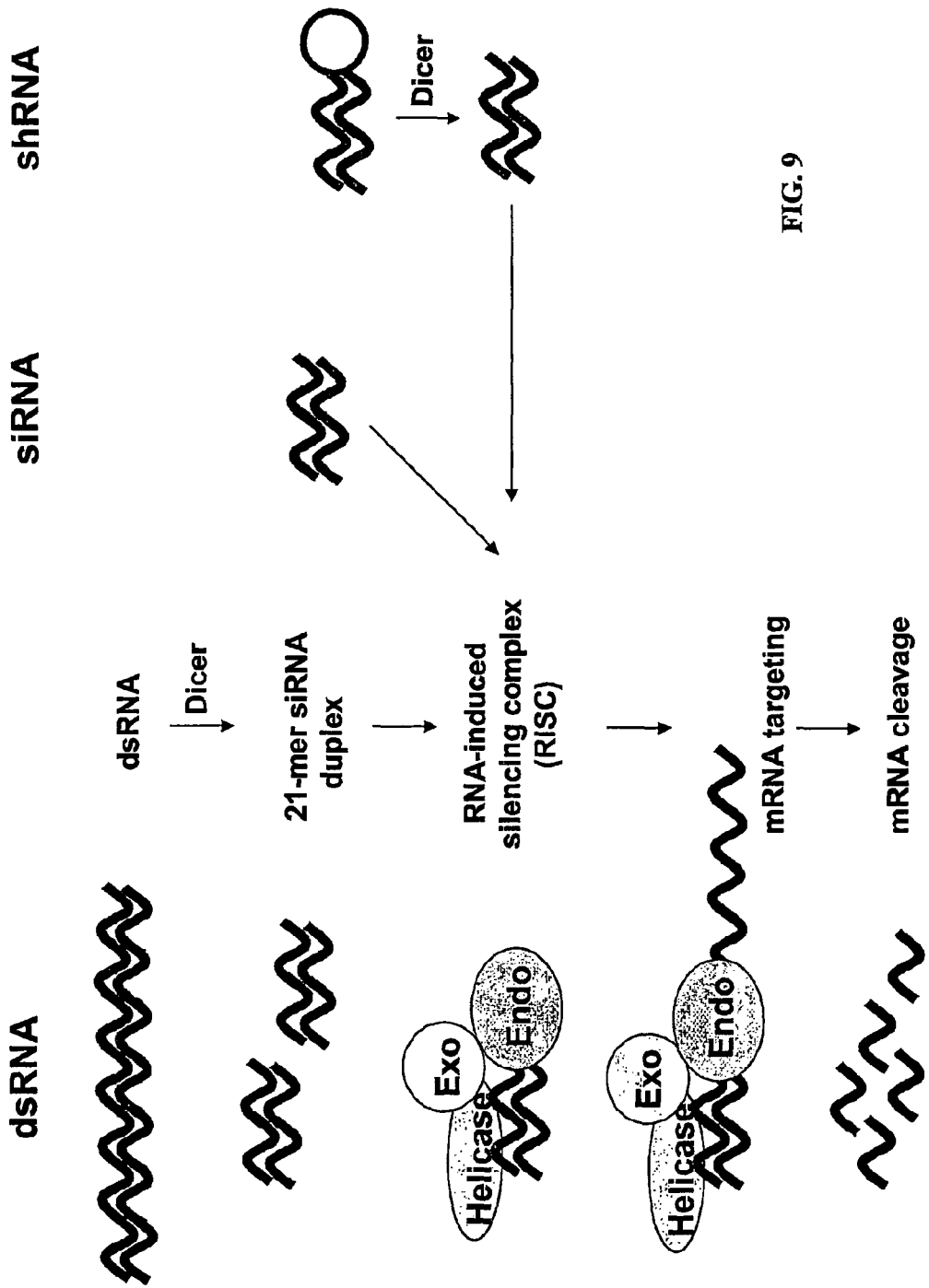
FIG. 9 shows a schematic illustration of RNA interference.

An exemplary computer system suitable from implementing the analytic methods of this invention is illustrated in FIG. 8. Computer system 801 is illustrated here as comprising internal components and as being linked to external components. The internal components of this computer system include one or more processor elements 802 interconnected with a main memory 803. For example, computer system 801 can be an Intel Pentium IV®-based processor of 2 GHZ or greater clock rate and with 256 MB or more main memory. In a preferred embodiment, computer system 801 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 804. This mass storage can be one or more hard disks that are typically packaged together with the processor and memory. Such hard disk are typically of 10 GB or greater storage capacity and more preferably have at least 40 GB of storage capacity. For example, in a preferred embodiment, described above, wherein a computer system of the invention comprises several nodes, each node can have its own hard drive. The head node preferably has a hard drive with at least 10 GB of storage capacity whereas each sibling node preferably has a hard drive with at least 40 GB of storage capacity. A computer system of the invention can further comprise other mass storage units including, for example, one or more floppy drives, one more CD-ROM drives, one or more DVD drives or one or more DAT drives.

Other external components typically include a user interface device 805, which is most typically a monitor and a keyboard together with a graphical input device 806 such as a "mouse." The computer system is also typically linked to a network link 807 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 8. The software components comprise both software components that are standard in the art and components that are special to the present invention. These software components are typically stored on mass storage such as the hard drive 804, but can be stored on other computer readable media as well including, for example, one or more floppy disks, one or more CD-ROMs, one or more DVDs or one or more DATs. Software component 810 represents an operating system which is responsible for managing the computer system and its network interconnections. The operating system can be, for example, of the Microsoft Windows™ family such as Windows 95, Window 98, Windows NT, Windows 2000 or Windows XP. Alternatively, the operating software can be a Macintosh operating system, a UNIX operating system or a LINUX operating system. Software components 811 comprises common languages and functions that are preferably present in the system to assist programs implementing methods specific to the present invention. Languages that can be used to program the analytic methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 812 comprises any analytic methods of the present invention described supra, preferably programmed in a procedural language or symbolic package. For example, software component 812 preferably includes programs that cause the processor to implement steps of accepting a plurality of measured signals and storing the measured signals in the memory. For example, the computer system can accept measured signals that are manually entered by a user (e.g., by means of the user interface). More preferably, however, the programs cause the computer system to retrieve measured signals from a database. Such a database can be stored on a mass storage (e.g., a hard drive) or other computer readable medium and loaded into the memory of the computer, or the compendium can be accessed by the computer system by means of the network 807.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

6. EXAMPLES

The following examples are presented by way of illustration of the present invention, and are not intended to limit the present invention in any way.

6.1. Example 1

Expression Profiling Reveals Gene Regulation of siRNAs

RNA interference (RNAi) or RNA silencing is widely used to suppress gene expression. RNA silencing is initiated by 21 nt short interfering RNAs (siRNAs) which target homologous mRNA species for degradation. Silencing is generally thought to be exquisitely specific, requiring near-perfect homology between the siRNA and its cognate mRNA. In this example, gene expression profiling are used to characterize the specificity of gene silencing by siRNAs in cultured human cells. The analysis revealed that different siRNAs regulated expression of unique sets of genes, among which were genes unrelated to the intended target or the degree of target silencing. These transcript profiles revealed direct silencing of non-targeted genes containing as few as eleven contiguous nucleotides of homology to the siRNA. Thus, the results demonstrate that silencing of endogenous genes requires far less homology with the siRNA than previously appreciated, and that siRNAs may cross-react with mRNAs of non-target genes having less than full length sequence similarity. These results establish the need to consider the contribution of off-target gene regulation to phenotypes resulting from gene silencing by RNAi.

Expression profiling is used to identify genes whose expression was altered as a result of RNAi-induced silencing in HeLa cells of two proteins involved in survival signalling pathways, MAPK14 (p38α) and the insulin-like growth factor receptor (IGF1R). 21-nucleotide double-stranded siRNAs were designed to target the coding regions of each of these genes according to standard selection rules (Elbashir et al., 2002, *Methods* 26:199-213), and subjected sequences to BLAST analysis to preclude significant homology to other genes in the human genome. Previous reports had indicated that a single nucleotide mismatch between the siRNA and the transcript could abolish silencing (Elbashir et al., 2001. *EMBO J.* 20:6877-6888). In this example, only those sequences that displayed fewer than 18 nucleotides of homology to genes other than the targeted gene were selected. Eight siRNAs designed to target MAPK14 and sixteen siRNAs designed to target IGF1R were transfected individually into HeLa cells. Following siRNA transfection, RNA was isolated and subjected to microarray analysis (Hughes et al., 2001, *Nat. Biotech.* 19, 342-347). The expression profiles resulting from silencing of the same target gene by different siRNAs were compared in order to identify common alterations in gene expression patterns.

TABLE I

MAPK14 and IGF1R siRNA sequences

| siRNA | Sequence (sense strand) |
|---|---|
| MAPK14-1 | CCUACAGAGAACUGCGGUU-dTdT (SEQ ID NO: 1) |
| Pos.4 mismatch | CCUGCAGAGAACUGCGGUU-dTdT (SEQ ID NO: 2) |
| Pos.5 mismatch | CCUAAAGAGAACUGCGGUU-dTdT (SEQ ID NO: 3) |
| Pos.15 mismatch | CCUACAGAGAACUGAGGUU-dTdT (SEQ ID NO: 4) |
| MAPK14-2 | AUGUGAUUGGUCUGUUGGA-dTdT (SEQ ID NO: 5) |
| MAPK14-3 | UUCUCCGAGGUCUAAAGUA-dTdT (SEQ ID NO: 6) |
| MAPK14-4 | UAAUUCACAGGGACCUAAA-dTdT (SEQ ID NO: 7) |
| MAPK14-5 | CCAGUGGCCGAUCCUUAUG-dTdT (SEQ ID NO: 8) |
| MAPK14-6 | UGCCUACUUUGCUCAGUAC-dTdT (SEQ ID NO: 9) |

TABLE I-continued

MAPK14 and IGF1R siRNA sequences

| siRNA | Sequence (sense strand) |
|---|---|
| MAPK14-7 | GUCAUCAGCUUUGUGCCAC-dTdT (SEQ ID NO: 10) |
| MAPK14-8 | GGCCUUUUCACGGGAACUC-dTdT (SEQ ID NO: 11) |
| IGF1R-1 | GCUCACGGUCAUUACCGAG-dTdT (SEQ ID NO: 12) |
| IGF1R-2 | CCUGAGGAACAUUACUCGG-dTdT (SEQ ID NO: 13) |
| IGF1R-3 | UGCUGACCUCUGUUACCUC-dTdT (SEQ ID NO: 14) |
| IGF1R-4 | CGACACGGCCUGUGUAGCU-dTdT (SEQ ID NO: 15) |
| IGF1R-5 | GAUGAUUCAGAUGGCCGGA-dTdT (SEQ ID NO: 16) |
| IGF1R-6 | CUUGCAGCAACUGUGGGAC-dTdT (SEQ ID NO: 17) |
| IGF1R-7 | CCUCACGGUCAUCCGCGGC-dTdT (SEQ ID NO: 18) |
| IGF1R-8 | CUACGCCCUGGUCAUCUUC-dTdT (SEQ ID NO: 19) |
| IGF1R-9 | UCUCAAGGAUAUUGGGCUU-dTdT (SEQ ID NO: 20) |
| IGF1R-10 | GGAUAUUGGGCUUUACAAC-dTdT (SEQ ID NO: 21) |
| IGF1R-11 | CAUUACUCGGGGGGCCATC-dTdT (SEQ ID NO: 22) |
| IGF1R-12 | AAUGCUGACCUCUGUUACC-dTdT (SEQ ID NO: 23) |
| IGF1R-13 | CAUUACCGAGUACUUGCUGCU (SEQ ID NO: 24) |
| IGF1R-14 | CUUGCUGCUGUUCCGAGUGGC (SEQ ID NO: 25) |
| IGF1R-15 | UCCGAGUGGCUGGCCUCGAGA (SEQ ID NO: 26) |
| IGF1R-16 | GGCCUCGAGAGCCUCGGAGAC (SEQ ID NO: 27) |
| luc | CGUACGCGGAAUACUUCGA-dTdT (SEQ ID NO: 28) |

Initial analysis of the expression profiles did not yield obvious common gene expression patterns in response to different siRNAs to the same target gene. Instead, each of the 8 siRNA duplexes targeted to MAPK14 produced a distinct expression pattern (FIG. 1A). Likewise, each of the sixteen siRNA duplexes to IGF1R produced a unique expression pattern (FIG. 1B). Virtually identical gene expression patterns were observed in three independent experiments, demonstrating that gene regulation resulting from a particular siRNA was reproducible. Thus, the transcript expression patterns were siRNA-specific. The number and identity of altered transcripts did not correspond to the ability of the siRNA to silence the target gene. All of the MAPK14 siRNA duplexes effectively silenced the target, demonstrating greater than 90% reduction in RNA and protein levels (FIG. 1A). Fourteen of the sixteen IGF1R siRNAs decreased IGF1R protein and RNA levels by greater than 60% (FIG. 1B). IGFR1-4 decreased the expression of IGF1R by 80%, yet resulted in the altered expression of fewer genes than IGFR1-5, which produced only 30% silencing of the target. Furthermore, an siRNA targeted to luciferase reproducibly regulated the expression of several genes despite the lack of a homologous target in the human genome. Thus, patterns of gene regulation are specific for the siRNA sequence utilized for silencing, rather than the intended target.

To gain an understanding of gene regulation by siRNA-induced silencing, a detailed concentration and kinetic analysis of MAPK14 protein and RNA knockdown by siRNA MAPK14-1 was performed. Although target gene silencing was detectable when the siRNA concentration was decreased by 1000-fold, off-target gene regulation was also detectable (FIG. 2). Many of these genes showed nearly identical half-maximal responses with respect to siRNA concentration as MAPK14 (~1 nM). The off-target gene regulation could not be titrated from silencing of the intended target, indicating that off-target gene regulation is not simply an artifact of high siRNA concentration.

A detailed kinetic analysis of MAPK14 protein and RNA knockdown was also performed, and expression profiling was employed to analyze temporal gene expression patterns. The Mapk14 protein demonstrated a half-life of approximately 40 hours following siRNA transfection (FIG. 3A). In contrast, the Mapk14 transcript was rapidly degraded, demonstrating half-maximal degradation at 11 hours post-transfection (FIG. 3B). Through expression profiling, gene regulation at early time points (6-12 hours) well before any observable decrease in the Mapk14 protein was observed. These gene expression changes therefore were unlikely to be secondary events resulting from loss of Mapk14 function. Further analysis revealed that the expression signature could be divided into several temporally distinct groups of transcripts (FIG. 3C). Group 1 contains a single transcript, the target MAPK14, showing rapid silencing. Group 2 contains nine transcripts demonstrating similar kinetics of silencing to MAPK14, with half-maximal degradation of 7-13 hours as determined by microarray. This same group of transcripts was downregulated with rapid kinetics in an independent experiment, demonstrating that these genes were reproducibly silenced by this siRNA. The rapid kinetics of transcript regulation suggests that these are direct gene regulation events. This is in contrast to Groups 3 and 4, for which half-maximal degradation occurs at approximately 40 hours and therefore likely represent indirect gene expression changes.

The rapidly downregulated transcripts were examined further to understand the basis of their co-regulation with MAPK14. These transcripts include KPNB3, RAP2A, FLJ20291, RRAD, RPA2, DKFZp564J157, AF093680, and two uncharacterized EST contigs (FIG. 4A). None of these genes is known to function in the Mapk14 pathway. All of these transcripts were found to contain regions of partial sequence homology to the siRNA duplex (FIG. 4A). Sequence alignment demonstrated that these genes could be divided into two subgroups. One subgroup, consisting of three off-target genes, contained a core of 14 to 15 nucleotides of homology encompassing the central region of the siRNA sequence. The second subgroup contained a smaller core of homology encompassing the nine nucleotides at the 3' end of the siRNA sequence. This is in contrast to transcripts in kinetic groups 3-5, which displayed only short stretches (6-8 nucleotides) of homology distributed randomly throughout the siRNA sequence. Thus, the bias for a core of sequence homology encompassing the 3' end of the siRNA is unique to the rapidly silenced transcripts. On the basis of published reports of gene silencing being abolished by nucleotide changes in the siRNA sequence (Elbashir et al., 2001. *EMBO J.* 20:6877-6888; Holen et al., 2002 *Nuc. Acids Res.* 30, 1757-1766), it would not have been predicted that this limited degree of sequence homology would be sufficient for transcript silencing. However, to test this possibility, the nucleotide at each position of the siRNA sequence was systematically substituted and the effect of the altered sequence on the expression signature was determined. Representative results are presented in FIG. 4B. A single nucleotide substitution at position 4 virtually eliminated silencing of MAPK14, and abolished silencing of the three off-target genes in subgroup 1 that contain homology to MAPK14 at this position. However, silencing was not abolished for the six off-target genes in subgroup 2 that do not contain homology to MAPK14 in this region. A single nucleotide substitution at position 5 reduced, but did not eliminate, MAPK14 silencing, and abolished silencing of the three genes in subgroup 1 that contained homology to MAPK14 in this region. The expression levels of the six off-target genes that do not share homology in this region were unaffected by this mismatch. These results confirm that silencing of the off-target genes is independent of loss of MAPK14 expression. A single nucleotide substitution at position 15 also reduced Mapk14 silencing, and abolished silencing of all nine off-target genes. The effect of the position 15 mismatch was more dramatic, presumably because all nine transcripts contain homology to MAPK14 in this region. RPA2 already contains a T rather than a C at this position, which would produce a G:U base pair with the antisense strand of the MAPK14 oligo. Thus, this substitution may be tolerated for base-pairing and silencing. The altered siRNA sequence would produce a U:U base pair, which may be less well tolerated, and thus abolish silencing for this transcript. Thus, it is shown that some nucleotide substitutions are more detrimental to silencing than others. Collectively, these results confirm that the sequence homology of these transcripts to MAPK14 accounts for their silencing by the MAPK14 siRNA.

Figure 4C:
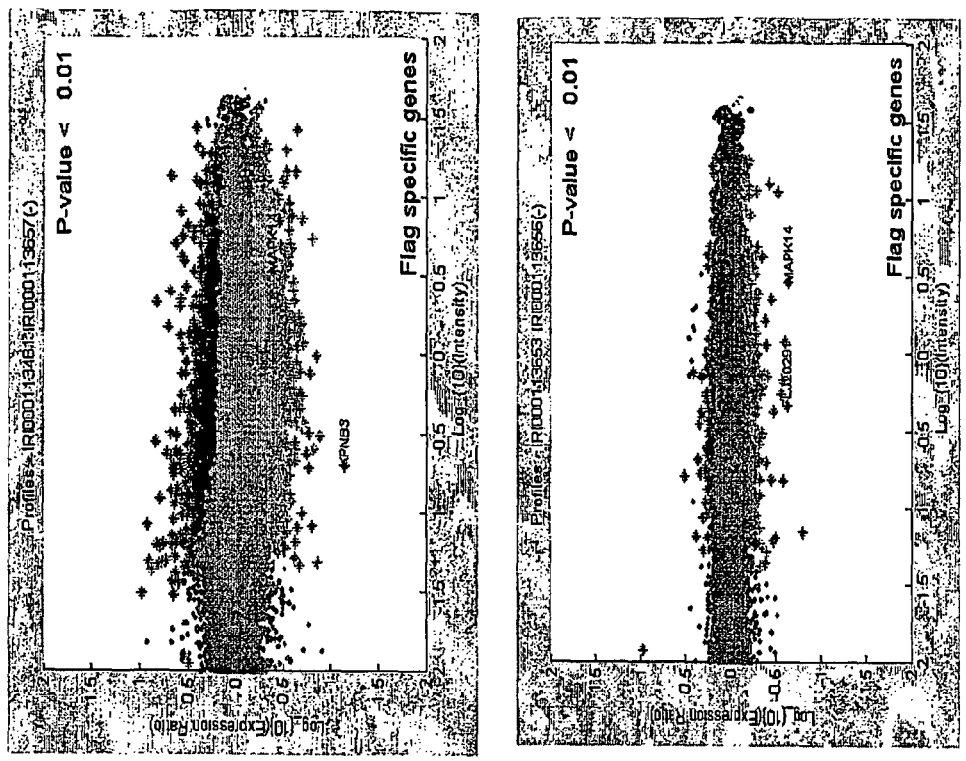
Figure 4B:
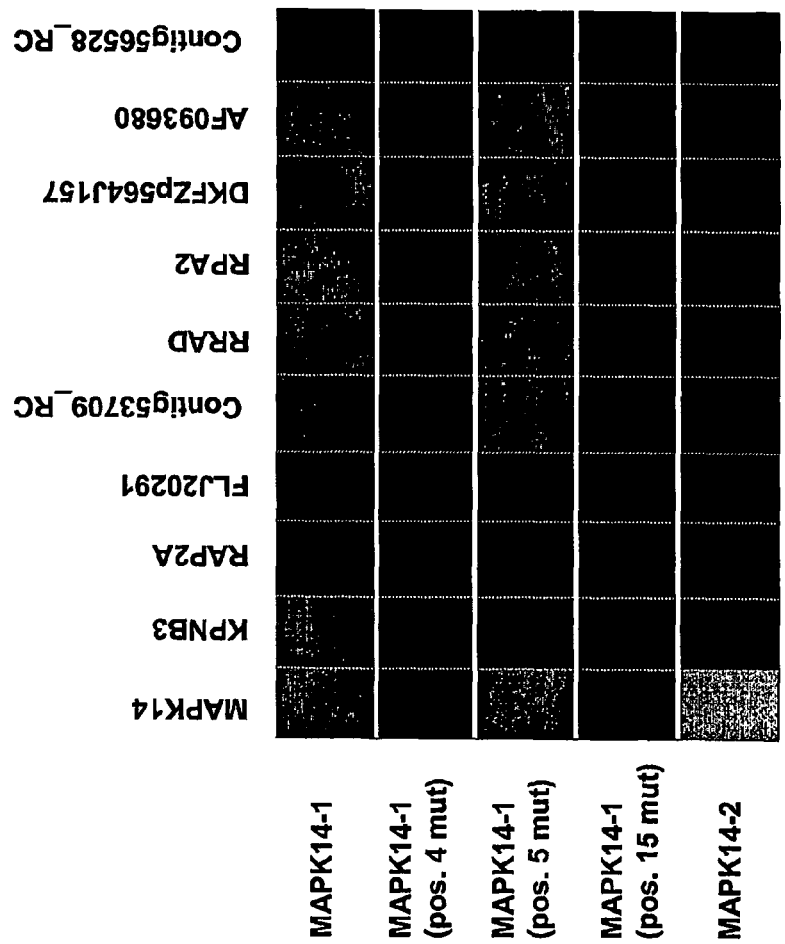

As further evidence that the observed off-target gene silencing is based on sequence homology and not a consequence of reduced MAPK14 expression, a different siRNA duplex designed to target MAPK14, but with a different oligo sequence, was tested. This second siRNA (MAPK14-2) maintained silencing of MAPK14 but did not silence any of the Group 2 transcripts, which contain no homology to the new siRNA sequence (FIG. 4B). Finally, siRNAs corresponding to those sequences illustrated in FIG. 4A for two off-target transcripts, KPNB3 and FLJ20291, silenced the expression of MAPK14 in addition to their intended targets (FIG. 4C). The KPNB3 siRNA shares 14 contiguous nucleotides, and a total of 15 nucleotides, of homology with MAPK14. The FLJ20291 siRNA shares only 11 contiguous nucleotides, and a total of 15 nucleotides, of homology with MAPK14. Thus, fifteen nucleotides, and perhaps as few as 11 contiguous nucleotides, of sequence homology is sufficient to direct silencing of non-targeted transcripts. Therefore, although RNA interference results in robust silencing of the desired target, off-target gene regulation can occur due to degradation of mRNA transcripts with partial homology to the siRNA sequence.

Figure 5:
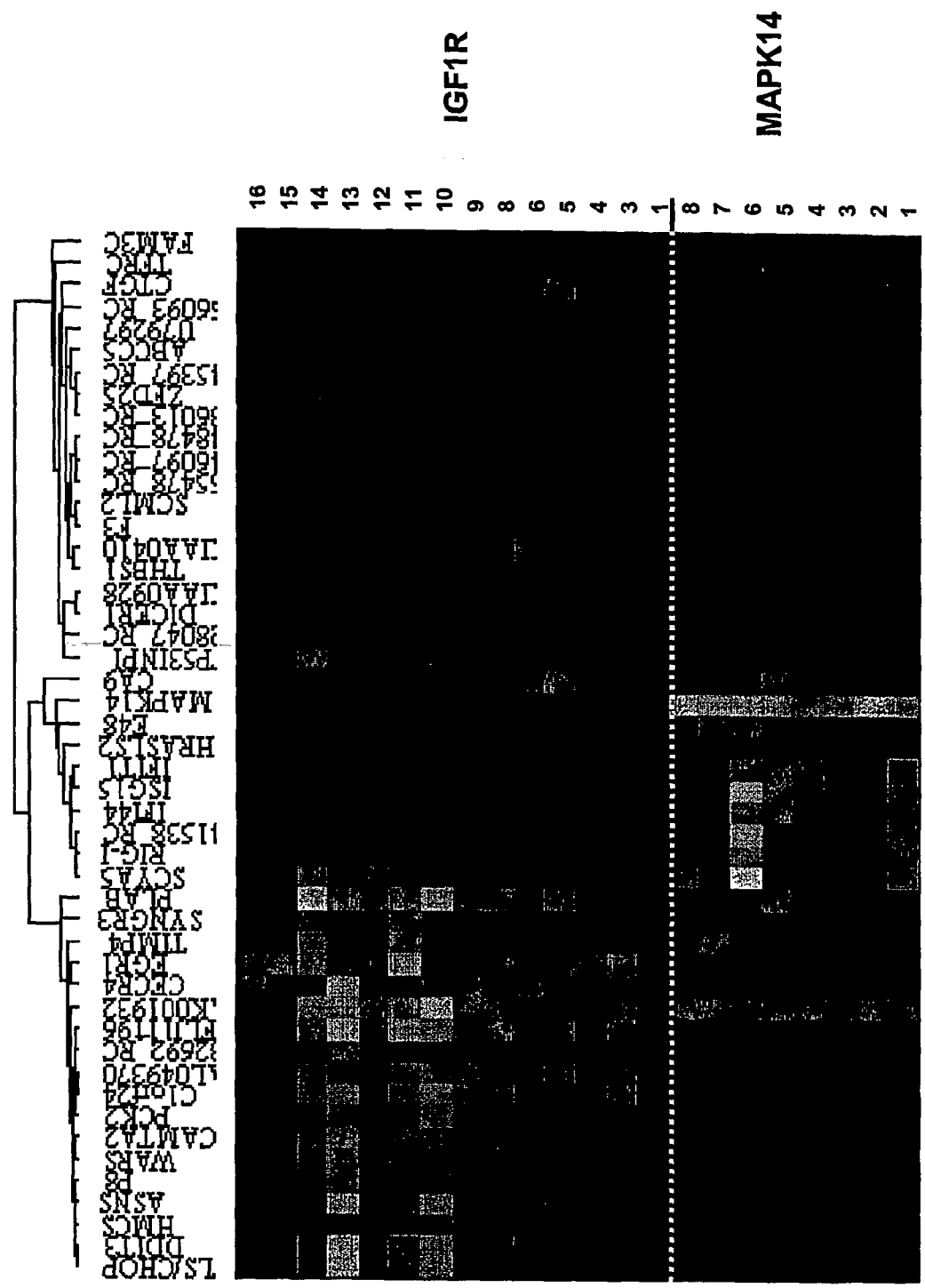

All 8 siRNA duplexes to MAPK14 and 14 of the siRNA duplexes to IGF1R effectively silenced the target gene. It should therefore be possible to identify common expression signatures among the different siRNAs to each target that would be indicative of loss of target gene function. When stringent statistical requirements were placed on the data to include only those expression patterns that resulted from target gene silencing by multiple siRNAs, common expression patterns were observed. The data for both experiments was combined into a single experiment group, and data analysis was restricted to those genes for which expression was altered by a minimum of two-fold in response to silencing by at least seven siRNAs. This analysis yielded a common pattern of decreased expression for 8 genes in response to the MAPK14 siRNAs (FIG. 5). Among these was the target, MAPK14, for which expression was suppressed ten-fold in response to all eight siRNAs. The common expression signature for MAPK14 silencing also included a number of genes normally induced in response to interferon. The analysis revealed 16 genes for which expression was reduced in response to the IGF1R siRNAs (FIG. 5). IGF1R itself was not identified as having decreased expression by this cluster analysis, because this gene is expressed at a sufficiently low level in this cell line to fall below the statistical criteria for inclusion. Quantitation of IGF1R mRNA by real-time PCR verified that the expression of IGF1R was suppressed in response to each of these siRNA duplexes (FIG. 1B). The common expression signature for IGF1R silencing included EGR1, an early growth response gene induced in response to growth factor signaling, several transcriptional regulators (HMCS, CAMTA2, CHOP, DDIT3), and genes involved in nutrient sensing and glucose regulation (PCK2, ASNS). A few transcripts were found to upregulated by siRNAs to both target genes. These were predominantly uncharacterized EST contigs, and presumably reflect genes that are stimulated in response to siRNA, in a manner similar to the induction of interferon genes in response to long dsRNA. One interesting exception was the induction of Dicer by multiple siRNAs to IGF1R, although the significance of this gene regulation is unclear. The genes down-regulated in response to IGF1R silencing were distinct from those regulated in response to MAPK14 silencing (FIG. 5). Thus, although the observed expression profiles include off-target gene regulation, expression patterns indicative of on-target gene regulation could be discerned.

Figure 6C:
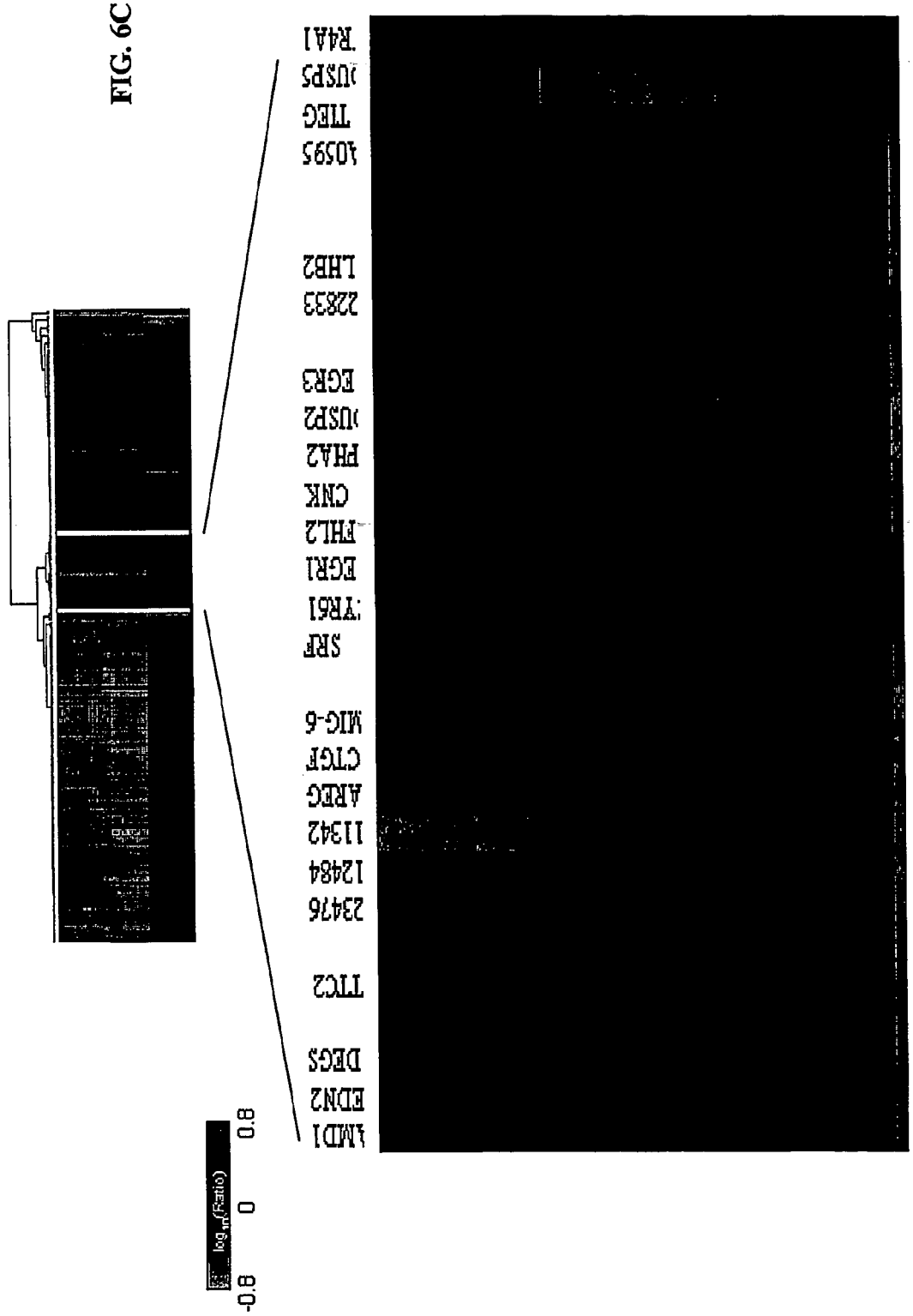

To further elucidate on-target gene regulation elicited by siRNA to IGF1R, expression profiling was employed to characterize IGF1R gene function in MCF7 breast carcinoma cells, which are responsive to IGF (insulin-like growth factor) stimulation. Following siRNA transfection, cells were serum-starved and subsequently treated with IGF to stimulate the IGF1R pathway. IGF1R siRNAs effectively silenced target gene expression (FIG. 6A), and interfered with receptor function as determined by reduced phosphorylation of the downstream protein Akt (FIG. 6B). In the absence of siRNA, Akt phosphorylation was evident even at very low doses of IGF. In contrast, Akt phosphorylation was severely reduced in response to IGF1R silencing even at saturating levels of IGF. IGF stimulation of mock-transfected cells identified transcripts whose expression is increased in response to IGF signalling (FIG. 6C). This group of genes is likely indicative of gene regulation through the IGF signal-transduction pathway, as the same genes were induced by IGF in several other cell lines. The expression of these IGF signature genes was either unchanged or reduced when IGF stimulation was performed in the background of IGF1R silencing by siRNA. Thus, expression signatures reflective of interference with target gene function can be identified through expression profiling. Taken together, these data indicate that gene expression profiles resulting from RNAi-induced gene silencing are a sum of both on- and off-target gene regulation.

RNA interference is a powerful tool for manipulation of gene expression in cultured mammalian cells. However, interpretation of phenotypes resulting from gene silencing by RNAi must include an evaluation of the impact of off-target gene regulation. The off-target gene products identified in this study are not known to function within the biological pathway for the intended targets and thus would not have been detected by protein or RNA analysis of genes relevant to the targeted signaling pathway. It was only through unbiased microarray analysis of the genome that these off-target events were identified. Detailed sequence analysis of the off-target genes demonstrated that a core of fifteen nucleotides, and as few as eleven contiguous nucleotides, of homology to the siRNA duplex could direct degradation of transcripts in addition to the intended target. A smaller core of nine nucleotides of homology to the 3' end of the siRNA may be sufficient for transcript silencing.

The biological function of small regulatory RNAs, including siRNAs and miRNAs (microRNAs), is not well understood. One prevailing question regards how the distinct silencing pathways of these two classes of regulatory RNA are determined. miRNAs are regulatory RNAs expressed from the genome, and are processed from precursor stem-loop structures to produce single-stranded nucleic acids that bind to sequences in the 3'UTR of the target mRNA (Lee et al., 1993, *Cell* 75:843-854; Reinhart et al., 2000, *Nature* 403:901-906; Lee et al., 2001, *Science* 294:862-864; Lau et al., 2001, *Science* 294:858-862; Hutvagner et al., 2001, *Science* 293:834-838). miRNAs bind to transcript sequences with only partial complementarity (Zeng et al., 2002, *Molec. Cell* 9:1327-1333) and repress translation without affecting steady-state RNA levels (Lee et al., 1993, *Cell* 75:843-854; Wightman et al., 1993, *Cell* 75:855-862). Both miRNAs and siRNAs are processed by Dicer and associate with components of the RNA-induced silencing complex (Hutvagner et al., 2001, *Science* 293:834-838; Grishok et al., 2001, *Cell* 106: 23-34; Ketting et al., 2001, *Genes Dev.* 15:2654-2659; Williams et al., 2002, *Proc. Natl. Acad. Sci. USA* 99:6889-6894; Hammond et al., 2001, *Science* 293:1146-1150; Mourlatos et al., 2002, *Genes Dev.* 16:720-728). A recent report (Hutvagner et al., 2002, *Sciencexpress* 297:2056-2060) hypothesizes that gene regulation through the miRNA pathway versus the siRNA pathway is determined solely by the degree of complementarity to the target transcript. The authors speculate that siRNAs with only partial homology to the mRNA target will function in translational repression, similar to an miRNA, rather than triggering RNA degradation. In contrast, it was clearly demonstrated in this example that synthetic siRNA duplexes with only partial homology to an mRNA transcript produce degradation of that transcript in cultured human cells. These results indicate that the degree of homology to the target transcript is not the sole determinant that distinguishes the function of siRNAs from miRNAs.

Given the small degree of homology implicated in off-target gene regulation, it will be difficult to select an siRNA sequence that will be absolutely specific for the target of interest. In addition, it will be difficult to predict all possible off-target events by searching the genome for genes with homology to the siRNA. Sequence homology alone does not guarantee that a transcript sequence will be accessible to the siRNA. In addition, not all potential off-target transcripts will be expressed in the cell line of interest. Thus, not all transcripts with sequence homology will be silenced. Furthermore, not all transcripts that are silenced will necessarily possess sequence homology. While direct homology-based gene silencing can be identified at early time points, gene expression patterns observed at later time points will include downstream gene regulation resulting from silencing of the target gene as well as any off-target genes. An additional layer of complexity could arise from the finding that siRNA duplexes have the potential to regulate gene expression through alteration of chromatin conformation. siRNA duplexes to centromeric repeats have recently been reported to affect heterochromatic silencing in *S. pombe* (Volpe et al., 2002, *Science* 297:1833-1837; Reinhart et al., 2002, *Science* 297:1831). It is conceivable that partial homology of an siRNA sequence to transcripts involved in maintaining chromatin conformation could produce alterations in expression of non-targeted genes located proximal to the target gene. Thus, RNA interference will produce complex alterations in gene expression, and interpretation of resulting phenotypes must be undertaken with care.

Despite the siRNA-specific off-target effects, common expression signatures, likely indicative of target protein loss, could be identified when multiple siRNA duplexes to the same target were analyzed. Incorporating multiple siRNA duplexes to silence a target gene of interest will increase the confidence with which an observed phenotype and expression pattern can be linked to target gene silencing. In this way, expression profiling in conjunction with gene silencing by RNAi will provide a powerful means to identify and characterize gene function in cultured mammalian cells.

6.2. Example 2 siRNA Pool Increases Silencing Specificity

This example demonstrates that by using siRNA pools, although the number of off-target events is increased (additive) but their magnitude regulation appears decreased. Decreasing the concentration of a single siRNA does not improve specificity, as off-target and on-target gene silencing titrate with a similar dose response. In contrast, increasing pools of siRNAs, maintain on-target silencing while reducing the number and magnitude of off-target gene silencing. This may be due to competition among the siRNAs for association with a limited amount of RISC. In these examples, all siRNAs have been previously determined to be effective at target silencing. Since all of these siRNAs target the same target gene transcript and thus can contribute to on-target silencing, but each has distinct off-target activity, the off-target activities are diluted with increasing number of siRNAs in the pool. As a result, the ratio of on-target:off-target gene silencing is increased, leading to increased specificity. This suggests that increasing to even larger pool sizes would lead to further increases in specificity. This increased specificity of gene silencing which would be of enormous benefit for target validation efforts.

FIG. 10 shows results with using an siRNA pool of 3 siRNAs. Each individual siRNA was transfected into HeLa cells at a concentration of 33 nM. The pool of the 3 siRNAs was transfected at 100 nM (33 nM each individual.) RNA was extracted 24 hours post-transfection and profiled against RNA from mock-transfected cells. The panel on the right indicates that on-target gene silencing was maintained in the pool. The number of off-target events was approximately the sum of the off-target events from each individual siRNA, but the magnitude of off-target silencing was reduced.

FIG. 11 shows that siRNA pool increased silencing specificity. Decreasing the concentration of a single siRNA does not improve specificity (upper panel). In contrast, increasing pool size maintained on-target silencing while reduced the number and magnitude of off-target gene silencing. This may be due to competition among the siRNAs for association with RISC. As a result, the ratio of on-target:off-target gene silencing was increased, leading to increased specificity. This suggests that increasing to even larger pool sizes would lead to further increases in specificity, which would be of enormous benefit for target validation efforts.

FIG. 12 shows results using an siRNA pool of 9 siRNAs. Each individual siRNA at 11 nM, pool contains 9 members each at 11 nM. With increased number of siRNAs in an siRNA pool, the number of signature genes in the pool was decreased, perhaps due to competition among the siRNAs for association with RISC. As a result, the magnitude of off-target silencing was reduced, and the ratio of on-target:off-target gene silencing was increased, leading to increased specificity.

6.3. Example 3

Assessment of Strand Preference in RNA Interference

In Example 1, it was shown that siRNAs have on-target as well as off-target activity. Some off-target genes were shown to be down-regulated with the same kinetics as the intended target gene, implying that these genes were directly regulated by the siRNAs. These coordinately down-regulated off-target signature genes were seen to align with the siRNA regulating them in two ways:

1) central contiguous stretch of identity: 11 or more bases in the central portion of the siRNA duplex all identical to the off-target gene.

2) 3'-based contiguous stretch of identity: 8 or more bases terminating within 3 bases of the 3' end of the siRNA duplex all identical to the off-target gene.

Alignments were seen to be identical to either the sense strand or the antisense strand for the siRNAs whose down-regulation kinetics were examined. It is inferred that for siRNAs where alignments are identical to the sense strand, the antisense strand is causing both on- and off-target regulation; for siRNAs where alignments are identical to the antisense strand, the sense strand is causing off-target regulation in addition to the activity of the antisense strand.

This example reports two methods of assessing which of the two strands of the siRNA duplex is silencing off-target genes when only single time point signatures are available.

In the first method, single time point signatures were assessed by polling all signature genes for greater extent of alignment with one siRNA strand vs. the other siRNA strand. This can also be used to evaluate strand preferences for genes down-regulated with the same kinetics as the intended target gene.

In the method, the signature gene sequences were aligned with both strands of the siRNA. Alignments to each strand were examined for the longest contiguous stretch of identity. The lengths of these stretches of identity were compared. The gene was considered to have voted for the strand to which it had the longest contiguous stretch of identity. The vote was weighted by the number of bases in excess in the longer of the two stretches of identity. The reasoning here was that, for example, a case where one strand has a 15-base stretch of identity and the other has a 5-base stretch of identity ought to weigh more heavily than a case where one strand has an 8-base stretch and the other has a 7-base stretch.

Thus a vote is a base in a contiguous stretch of identity in excess in one strand. Total votes represent the total excess length in contiguous identity for the winning strand in all the genes where it dominated.

The background for this method was determined by examining alignments of both strands of the siRNA to a plurality of genes for which the siRNA regulation signature was determined, e.g., all genes assayed using a microarray, letting the strands vote as above, and calculating the average excess weight per gene for each strand of the siRNA.

In the second method, single time point signatures were assessed by comparison of signature gene alignments with the 3-biased model developed from alignments of siRNAs with genes they down-regulated with the same kinetics as the intended target gene.

In the method, the signature genes were analyzed to determine the fraction matching the 3'-biased model of off-target gene alignment (see alignment 2) above). The signature gene sequences were aligned with both strands of the siRNA. Alignments to each strand were examined for contiguous stretches of identity. Alignments were tallied if they:

a) had a contiguous stretch of identity of at least 7 bases; and b) terminated within 3 bases of the 3' end of the particular strand.

The tally of alignments meeting the above criteria with identity to the sense strand and with identity to the antisense strand was compared as:

$$SLR = \log_{10}(\text{sense-identical-tally}/\text{antisense-identical-tally})$$

The significance of the SLR was assessed by comparing the sense-identical and antisense-identical tallies for the signature with the sense-identical and antisense-identical tallies for all sequences represented on the chip on which the siRNA regulation signature was determined.

Significance was calculated from the hypergeometric distribution, where:

x, Sample-selection=signature tally for one strand n, Sample-total=signature tallies for both strands M, Parent-selection=chip tally for the same strand N, Parent-total=chip tallies for both strands, and the equation for the hypergeometric distribution is:

$$h(x, n, M, N) = \frac{\binom{M}{x}\binom{N-M}{n-x}}{\binom{N}{n}}$$

As the hypergeometric distribution is not symmetric, both tails of both the sense-strand and antisense-strand selection hypergeometric distributions were used. The two tails corresponding to sense-identical excess were averaged to give the p-value for excess sense identity, both tails corresponding to antisense-identical excess were averaged to give the p-value for excess antisense identity.

The strand preference results of both these methods were seen to match the results of strand preference analysis of genes down-regulated with the same kinetics as the target gene.

The first method in particular was seen to be effective for analysis of 12-hour, 24-hour and 48-hour signatures. 24-hour signatures generally gave the most significant results.

In effect, the utility of a significant fraction of the signature genes, or all signature genes as a whole, for determination of the strand preference of an siRNA implies that the direct effect of the siRNA on gene expression in a cell is represented by a significant fraction of the signature genes. For example, both methods estimated that about 35-40% genes of a 12 hour IGF1R-73 signature, i.e. about 12 genes, was relevant for estimation of its strand bias; whereas about 35-40% genes of a 24 hour IGF1R-73 signature, i.e. about 80 genes, was also relevant.

Table II shows a library of 377 siRNAs. The BioID numbers in Table II are also used in this disclosure to identify siRNAs. For example, siRNA MAPK14-193 corresponds to siRNA with the BioID No. 193 in Table II.

TABLE II

A library of 377 siRNA

| BioID | accession number | start position | 19mer sequence | % silencing | Set 1 | Set 2 | SEQ ID NO |
|---|---|---|---|---|---|---|---|
| 31 | NM_000075 | 437 | TGTTGTCCGGCTGATGGAC | 27.0 | Training | Training | 39 |
| 36 | NM_001813 | 1036 | ACTCTTACTGCTCTCCAGT | 86.1 | Test | Training | 40 |
| 37 | NM_001813 | 1278 | CTTAACACGGATGCTGGTG | 60.1 | Test | Training | 41 |
| 38 | NM_001813 | 3427 | GGAGAGCTTTCTAGGACCT | 88.0 | Test | Training | 42 |
| 39 | NM_004073 | 192 | AGTCATCCCGCAGAGCCGC | 55.0 | Training | Training | 43 |
| 40 | NM_004073 | 1745 | ATCGTAGTGCTTGTACTTA | 70.0 | Training | Training | 44 |
| 41 | NM_004073 | 717 | GGAGACGTACCGCTGCATC | 65.0 | Training | Training | 45 |
| 42 | AK092024 | 437 | GCAGTGATTGCTCAGCAGC | 93.0 | Training | Training | 46 |
| 43 | NM_030932 | 935 | GAGTTTACCGACCACCAAG | 81.0 | Training | Training | 47 |
| 44 | NM_030932 | 1186 | TGCGGATGCCATTCAGTGG | 35.0 | Training | Training | 48 |
| 45 | NM_030932 | 1620 | CACGGTTGGCAGAGTCTAT | 73.0 | Training | Training | 49 |
| 49 | U53530 | 169 | GCAAGTTGAGCTCTACCGC | 59.0 | Training | Training | 50 |
| 50 | U53530 | 190 | TGGCCAGCGCTTACTGGAA | 75.0 | Training | Training | 51 |
| 64 | NM_006101 | 1623 | GTTCAAAAGCTGGATGATC | 79.0 | Test | Training | 52 |
| 65 | NM_006101 | 186 | GGCCTCTATACCCCTCAAA | 74.4 | Test | Training | 53 |
| 66 | NM_006101 | 968 | AGAACCGAATCGTCTAGAG | 80.3 | Test | Training | 54 |
| 67 | NM_000859 | 253 | CACGATGCATAGCCATCCT | 25.0 | Training | Training | 55 |
| 68 | NM_000859 | 1075 | CAGAGACAGAATCTACACT | 45.0 | Training | Training | 56 |
| 69 | NM_000859 | 1720 | CAACAGAAGGTTGTCTTGT | 50.0 | Training | Training | 57 |
| 70 | NM_000859 | 2572 | TTGTGTGTGGGACCGTAAT | 80.0 | Training | Training | 58 |
| 71 | NM_000875 | 276 | GCTCACGGTCATTACCGAG | 63.9 | Training | Training | 59 |
| 72 | NM_000875 | 441 | CCTGAGGAACATTACTCGG | 0.0 | Training | Training | 60 |
| 73 | NM_000875 | 483 | TGCTGACCTCTGTTACCTC | 50.0 | Training | Training | 61 |
| 74 | NM_000875 | 777 | CGACACGGCCTGTGTAGCT | 58.0 | Training | Training | 62 |
| 75 | NM_000875 | 987 | CGGCAGCCAGAGCATGTAC | 63.0 | Training | Training | 63 |
| 76 | NM_000875 | 1320 | CCAGAACTTGCAGCAACTG | 70.0 | Training | Training | 64 |
| 81 | NM_000875 | 351 | CCTCACGGTCATCCGCGGC | 0.0 | Training | Training | 65 |
| 83 | NM_000875 | 387 | CTACGCCCTGGTCATCTTC | 32.0 | Training | Training | 66 |
| 84 | NM_000875 | 417 | TCTCAAGGATATTGGGCTT | 54.0 | Training | Training | 67 |
| 85 | NM_000875 | 423 | GGATATTGGGCTTTACAAC | 71.0 | Training | Training | 68 |
| 86 | NM_000875 | 450 | CATTACTCGGGGGGCCATC | 53.0 | Training | Training | 69 |
| 87 | NM_000875 | 481 | AATGCTGACCTCTGTTACC | 54.6 | Training | Training | 70 |
| 117 | NM_004523 | 1689 | CTGGATCGTAAGAAGGCAG | 74.7 | Training | Test | 71 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 118 | NM_004523 | 484 | TGGAAGGTGAAAGGTCACC | 16.0 | Training | Test | 72 |
| 119 | NM_004523 | 802 | GGACAACTGCAGCTACTCT | 84.1 | Training | Test | 73 |
| 139 | NM_002358 | 219 | TACGGACTCACCTTGCTTG | 83.0 | Training | Training | 74 |
| 144 | NM_001315 | 779 | GTATATACATTCAGCTGAC | 78.5 | Training | | 75 |
| 145 | NM_001315 | 1080 | GGAACACCCCCGCTTATC | 27.2 | Training | | 76 |
| 146 | NM_001315 | 1317 | GTGGCCGATCCTTATGATC | 81.3 | Training | | 77 |
| 152 | NM_001315 | 607 | ATGTGATTGGTCTGTTGGA | 95.0 | Training | | 78 |
| 153 | NM_001315 | 1395 | GTCATCAGCTTTGTGCCAC | 92.0 | Training | | 79 |
| 154 | NM_001315 | 799 | TAATTCACAGGGACCTAAA | 82.0 | Training | | 80 |
| 155 | NM_001315 | 1277 | TGCCTACTTTGCTCAGTAC | 95.0 | Training | | 81 |
| 193 | NM_001315 | 565 | CCTACAGAGAACTGCGGTT | 90.0 | Training | | 82 |
| 190 | NM_001315 | 763 | TTCTCCGAGGTCTAAAGTA | 87.0 | Training | | 83 |
| 192 | NM_001315 | 1314 | CCAGTGGCCGATCCTTATG | 89.0 | Training | | 84 |
| 194 | NM_001315 | 1491 | GGCCTTTTCACGGGAACTC | 97.0 | Training | | 85 |
| 201 | NM_016195 | 2044 | CTGAAGAAGCTACTGCTTG | 80.3 | Test | Training | 86 |
| 202 | NM_016195 | 4053 | GACATGCGAATGACACTAG | 75.9 | Test | Training | 87 |
| 203 | NM_016195 | 3710 | AGAGGAACTCTCTGCAAGC | 84.7 | Test | Training | 88 |
| 204 | NM_014875 | 4478 | AAACTGGGAGGCTACTTAC | 93.0 | Test | Training | 89 |
| 205 | NM_014875 | 1297 | ACTGACAACAAAGTGCAGC | 37.0 | Test | Training | 90 |
| 206 | NM_014875 | 5130 | CTCACATTGTCCACCAGGA | 91.6 | Test | Training | 91 |
| 210 | NM_004523 | 4394 | GACCTGTGCCTTTTAGAGA | 63.7 | Training | Test | 92 |
| 211 | NM_004523 | 2117 | GACTTCATTGACAGTGGCC | 71.0 | Training | Test | 93 |
| 212 | NM_004523 | 799 | AAAGGACAACTGCAGCTAC | 49.0 | Training | Test | 94 |
| 213 | NM_000314 | 2753 | TGGAGGGGAATGCTCAGAA | 40.0 | Training | Training | 95 |
| 214 | NM_000314 | 2510 | TAAAGATGGCACTTTCCCG | 79.0 | Training | Training | 96 |
| 215 | NM_000314 | 2935 | AAGGCAGCTAAAGGAAGTG | 55.0 | Training | Training | 97 |
| 234 | NM_007054 | 963 | TATTGGGCCAGCAGATTAC | 76.9 | Training | Training | 98 |
| 235 | NM_007054 | 593 | TTATGACGCTAGGCCACAA | 74.4 | Training | Training | 99 |
| 236 | NM_007054 | 1926 | GGAGAAAGATCCCTTTGAG | 78.3 | Training | Training | 100 |
| 237 | NM_006845 | 324 | ACAAAAACGGAGATCCGTC | 72.2 | Training | Training | 101 |
| 238 | NM_006845 | 2206 | ATAAGCAGCAAGAAACGGC | 30.9 | Training | Training | 102 |
| 239 | NM_006845 | 766 | GAATTTCGGGCTACTTTGG | 65.8 | Training | Training | 103 |
| 240 | NM_005163 | 454 | CGCACCTTCCATGTGGAGA | 86.8 | Training | Training | 104 |
| 241 | NM_005163 | 1777 | AGACGTTTTTGTGCTGTGG | 76.0 | Training | Training | 105 |
| 242 | NM_005163 | 1026 | GCTGGAGAACCTCATGCTG | 87.8 | Training | Training | 106 |
| 243 | NM_005733 | 2139 | CTCTACCACTGAAGAGTTG | 90.7 | Training | Training | 107 |
| 244 | NM_005733 | 1106 | AAGTGGGTCGTAAGAACCA | 82.5 | Training | Training | 108 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 245 | NM_005733 | 696 | GAAGCTGTCCCTGCTAAAT | 93.4 | Training | Training | 109 |
| 246 | NM_001813 | 3928 | GAAGAGATCCCAGTGCTTC | 86.8 | Test | Training | 110 |
| 247 | NM_001813 | 4456 | TCTGAAAGTGACCAGCTCA | 82.5 | Test | Training | 111 |
| 248 | NM_001813 | 2293 | GAAAATGAAGCTTTGCGGG | 78.4 | Test | Training | 112 |
| 249 | NM_005030 | 1135 | AAGAAGAACCAGTGGTTCG | 83.0 | Test | Test | 113 |
| 250 | NM_005030 | 572 | CCGAGTTATTCATCGAGAC | 93.6 | Test | Test | 114 |
| 251 | NM_005030 | 832 | AAGAGACCTACCTCCGGAT | 85.0 | Test | Test | 115 |
| 255 | NM_001315 | 3050 | AATATCCTCAGGGGTGGAG | 36.0 | Training | | 116 |
| 256 | NM_001315 | 1526 | GTGCCTCTTGTTGCAGAGA | 88.0 | Training | | 117 |
| 257 | NM_001315 | 521 | GAAGCTCTCCAGACCATTT | 96.0 | Training | | 118 |
| 261 | NM_006218 | 456 | AGAAGCTGTGGATCTTAGG | 65.3 | Test | Training | 119 |
| 262 | NM_006218 | 3144 | TGATGCACATCATGGTGGC | 68.9 | Test | Training | 120 |
| 263 | NM_006218 | 2293 | CTAGGAAACCTCAGGCTTA | 94.7 | Test | Training | 121 |
| 264 | NM_000075 | 1073 | GCGAATCTCTGCCTTTCGA | 79.0 | Training | Training | 122 |
| 265 | NM_000075 | 685 | CAGTCAAGCTGGCTGACTT | 78.0 | Training | Training | 123 |
| 266 | NM_000075 | 581 | GGATCTGATGCGCCAGTTT | 77.0 | Training | Training | 124 |
| 288 | NM_020242 | 1829 | GCACAACTCCTGCAAATTC | 87.4 | Training | Training | 125 |
| 289 | NM_020242 | 3566 | GATGGAAGAGCCTCTAAGA | 82.7 | Training | Training | 126 |
| 290 | NM_020242 | 2631 | ACGAAAAGCTGCTTGAGAG | 73.4 | Training | Training | 127 |
| 291 | NM_004073 | 570 | GAAGACCATCTGTGGCACC | 65.0 | Training | Training | 128 |
| 292 | NM_004073 | 1977 | TCAGGGACCAGCTTTACTG | 60.0 | Training | Training | 129 |
| 293 | NM_004073 | 958 | GTTACCAAGAGCCTCTTTG | 75.0 | Training | Training | 130 |
| 294 | NM_005026 | 3279 | AACCAAAGTGAACTGGCTG | 56.3 | Training | Training | 131 |
| 295 | NM_005026 | 2121 | GATCGGCCACTTCCTTTTC | 70.9 | Training | Training | 132 |
| 296 | NM_005026 | 4004 | AGAGATCTGGGCCTCATGT | 67.3 | Training | Training | 133 |
| 303 | NM_000051 | 5373 | AGTTCGATCAGCAGCTGTT | 60.9 | Training | Training | 134 |
| 304 | NM_000051 | 3471 | TAGATTGTTCCAGGACACG | 71.2 | Training | Training | 135 |
| 305 | NM_000051 | 7140 | GAAGTTGGATGCCAGCTGT | 56.3 | Training | Training | 136 |
| 309 | NM_004064 | 1755 | TGGTGATCACTCCAGGTAG | 25.3 | Training | Training | 137 |
| 310 | NM_004064 | 1505 | TGTCCCTTTCAGAGACAGC | 5.0 | Training | Training | 138 |
| 311 | NM_004064 | 1049 | GACGTCAAACGTAAACAGC | 50.2 | Training | Training | 139 |
| 312 | NM_006219 | 1049 | AAGTTCATGTCAGGGCTGG | 76.6 | Test | Training | 140 |
| 313 | NM_006219 | 2631 | CAAAGATGCCCTTCTGAAC | 88.9 | Test | Training | 141 |
| 314 | NM_006219 | 453 | AATGCGCAAATTCAGCGAG | 32.9 | Test | Training | 142 |
| 339 | NM_003600 | 437 | GCACAAAAGCTTGTCTCCA | 96.0 | Test | Training | 143 |
| 340 | NM_003600 | 1071 | TTGCAGATTTTGGGTGGTC | 37.0 | Test | Training | 144 |
| 341 | NM_003600 | 1459 | ACAGTCTTAGGAATCGTGC | 61.1 | Test | Training | 145 |
| 342 | NM_004958 | 1476 | AGGACTTCGCCCATAAGAG | 61.8 | Test | Training | 146 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 343 | NM_004958 | 5773 | CAACCTCCAGGATACACTC | 80.9 | Test | Training | 147 |
| 344 | NM_004958 | 7886 | CCAACTTTCTAGCTGCTGT | 71.1 | Test | Training | 148 |
| 348 | NM_004856 | 1999 | GAATGTGAGCGTAGAGTGG | 92.2 | Training | Training | 149 |
| 349 | NM_004856 | 1516 | CCATTGGTTACTGACGTGG | 87.7 | Training | Training | 150 |
| 350 | NM_004856 | 845 | AACCCAAACCTCCACAATC | 71.8 | Training | Training | 151 |
| 369 | XM_294563 | 117 | GAAAGAAGCAGTTGACCTC | 59.9 | Training | Training | 152 |
| 370 | XM_294563 | 2006 | CTAAAAGCTGGGTGGACTC | 69.4 | Training | Training | 153 |
| 371 | XM_294563 | 389 | GAAAGCACCTCTTTGTGTG | 64.2 | Training | Training | 154 |
| 399 | NM_000546 | 1286 | TGAGGCCTTGGAACTCAAG | 17.8 | | | 155 |
| 400 | NM_000546 | 2066 | CCTCTTGGTCGACCTTAGT | 74.5 | | | 156 |
| 401 | NM_000546 | 1546 | GCACCCAGGACTTCCATTT | 93.2 | | | 157 |
| 417 | NM_001184 | 3790 | GAAACTGCAGCTATCTTCC | 75.8 | Training | Training | 158 |
| 418 | NM_001184 | 7717 | GTTACAATGAGGCTGATGC | 73.0 | Training | Training | 159 |
| 419 | NM_001184 | 5953 | TCACGACTCGCTGAACTGT | 78.8 | Training | Training | 160 |
| 453 | NM_005978 | 323 | GACCGACCCTGAAGCAGAA | 91.3 | Test | Test | 161 |
| 454 | NM_005978 | 254 | TTCCAGGAGTATGCTGTTT | 74.4 | Test | Test | 162 |
| 455 | NM_005978 | 145 | GGAACTTCTGCACAAGGAG | 96.5 | Test | Test | 163 |
| 465 | NM_000551 | 495 | TGTTGACGGACAGCCTATT | 75.5 | Test | Training | 164 |
| 466 | NM_000551 | 1056 | GGCATTGGCATCTGCTTTT | 89.7 | Test | Training | 165 |
| 467 | NM_000551 | 3147 | GTGAATGAGACACTCCAGT | 82.2 | Test | Training | 166 |
| 468 | NM_002658 | 1944 | GAGCTGGTGTCTGATTGTT | 82.8 | Test | Training | 167 |
| 469 | NM_002658 | 1765 | GTGTAAGCAGCTGAGGTCT | 44.4 | Test | Training | 168 |
| 470 | NM_002658 | 232 | CTGCCCAAAGAAATTCGGA | 47.8 | Test | Training | 169 |
| 507 | NM_003391 | 792 | ATTTGCCCGCGCATTTGTG | 27.2 | Test | Training | 170 |
| 508 | NM_003391 | 2171 | AGAAGATGAATGGTCTGGC | 69.4 | Test | Training | 171 |
| 509 | NM_003391 | 981 | AACGGGCGATTATCTCTGG | 43.3 | Test | Training | 172 |
| 540 | NM_002387 | 3490 | GACTTAGAGCTGGGAATCT | 83.7 | Test | Training | 173 |
| 541 | NM_002387 | 4098 | AGTTGAGGAGGTTTCTGCA | 86.1 | Test | Training | 174 |
| 542 | NM_002387 | 1930 | GGATTATATCCAGCAGCTC | 82.3 | Test | Training | 175 |
| 585 | NM_014885 | 509 | GTGGCTGGATTCATGTTCC | 81.5 | Training | Training | 176 |
| 586 | NM_014885 | 798 | CAAGGCATCCGTTATATCT | 84.7 | Training | Training | 177 |
| 587 | NM_014885 | 270 | ACCAGGATTTGGAGTGGAT | 84.7 | Training | Training | 178 |
| 639 | NM_001274 | 250 | CTGAAGAAGCAGTCGCAGT | 77.7 | | | 179 |
| 640 | NM_001274 | 858 | ATCGATTCTGCTCCTCTAG | 86.2 | | | 180 |
| 641 | NM_001274 | 1332 | TGCCTGAAAGAGACTTGTG | 85.4 | | | 181 |
| 651 | NM_001259 | 807 | TCTTGGACGTGATTGGACT | 89.8 | Training | Training | 182 |
| 652 | NM_001259 | 1036 | AGAAAACCTGGATTCCCAC | 88.9 | Training | Training | 183 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 653 | NM_001259 | 556 | ACCACAGAACATTCTGGTG | 89.3 | Training | Training | 184 |
| 672 | NM_003161 | 2211 | GAAAGCCAGACAACTTCTG | 87.1 | Test | Training | 185 |
| 673 | NM_003161 | 1223 | CTCTCAGTGAAAGTGCCAA | 91.2 | Test | Training | 186 |
| 674 | NM_003161 | 604 | GACACTGCCTGCTTTTACT | 98.1 | Test | Training | 187 |
| 678 | NM_004972 | 3526 | AAGAACCTGGTGAAAGTCC | 57.2 | Training | Training | 188 |
| 679 | NM_004972 | 4877 | GAAGTGCAGCAGGTTAAGA | 54.8 | Training | Training | 189 |
| 680 | NM_004972 | 1509 | AGCCGAGTTGTAACTATCC | 74.9 | Training | Training | 190 |
| 684 | NM_007194 | 1245 | GATCACAGTGGCAATGGAA | 80.9 | | | 191 |
| 685 | NM_007194 | 1432 | AAACTCTTGGAAGTGGTGC | 39.2 | | | 192 |
| 686 | NM_007194 | 2269 | ATGAATCCACAGCTCTACC | 44.6 | | | 193 |
| 687 | NM_007313 | 3866 | GAATGGAAGCCTGAACTGA | 92.4 | Test | Training | 194 |
| 688 | NM_007313 | 2451 | AGACATCATGGAGTCCAGC | 5.0 | Test | Training | 195 |
| 689 | NM_007313 | 1296 | CAAGTTCTCCATCAAGTCC | 91.1 | Test | Training | 196 |
| 711 | NM_139049 | 129 | GGAATAGTATGCGCAGCTT | 92.5 | Test | Training | 197 |
| 712 | NM_139049 | 369 | GTGATTCAGATGGAGCTAG | 89.0 | Test | Training | 198 |
| 713 | NM_139049 | 969 | CACCCGTACATCAATGTCT | 77.0 | Test | Training | 199 |
| 858 | NM_001253 | 522 | TCATTGGAAGAACAGCGGC | 0.0 | Test | Training | 200 |
| 859 | NM_001253 | 2571 | AAGAAGACGTTCAGCGACA | 93.5 | Test | Training | 201 |
| 860 | NM_001253 | 911 | AAAAAGCCTGCCCTTGGTT | 88.1 | Test | Training | 202 |
| 1110 | NM_006101 | 1847 | CTTGCAACGTCTGTTAGAG | 72.3 | Test | Training | 203 |
| 1111 | NM_006101 | 999 | CTGAAGGCTTCCTTACAAG | 82.9 | Test | Training | 204 |
| 1112 | NM_006101 | 1278 | CAGAAGTTGTGGAATGAGG | 79.1 | Test | Training | 205 |
| 1182 | NM_016231 | 1302 | GCAATGAGGACAGCTTGTG | 79.8 | Test | Training | 206 |
| 1183 | NM_016231 | 1829 | TGTAGCTTTCCACTGGAGT | 79.3 | Test | Training | 207 |
| 1184 | NM_016231 | 1019 | TCTCCTTGTGAACAGCAAC | 62.5 | Test | Training | 208 |
| 1212 | NM_001654 | 1072 | AGTGAAGAACCTGGGGTAC | 79.3 | Test | Training | 209 |
| 1213 | NM_001654 | 595 | GTTCCACCAGCATTGTTCC | 86.2 | Test | Training | 210 |
| 1214 | NM_001654 | 1258 | GAATGAGATGCAGGTGCTC | 86.9 | Test | Training | 211 |
| 1287 | NM_005417 | 2425 | CAATTCGTCGGAGGCATCA | 73.9 | Test | Training | 212 |
| 1288 | NM_005417 | 1077 | GGGGAGTTTGCTGGACTTT | 66.4 | Test | Training | 213 |
| 1289 | NM_005417 | 3338 | GCAGTGCCTGCCTATGAAA | 68.2 | Test | Training | 214 |
| 1290 | NM_001982 | 3223 | CTAGACCTAGACCTAGACT | 63.5 | Test | Training | 215 |
| 1291 | NM_001982 | 3658 | GAGGATGTCAACGGTTATG | 49.4 | Test | Training | 216 |
| 1292 | NM_001982 | 2289 | CAAAGTCTTGGCCAGAATC | 45.3 | Test | Training | 217 |
| 1293 | NM_005400 | 249 | GATCGAGCTGGCTGTCTTT | 85.4 | Test | Training | 218 |
| 1294 | NM_005400 | 1326 | GGTCTTAAAGAAGGACGTC | 63.4 | Test | Training | 219 |
| 1295 | NM_005400 | 1848 | TGAGGACGACCTATTTGAG | 0.0 | Test | Training | 220 |
| 1317 | NM_002086 | 465 | TGAGCTGGTGGATTATCAC | 85.5 | Test | Test | 221 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 1318 | NM_002086 | 183 | CTGGTACAAGGCAGAGCTT | 95.5 | Test | Test | 222 |
| 1319 | NM_002086 | 720 | CCGGAACGTCTAAGAGTCA | 92.3 | Test | Test | 223 |
| 1332 | NM_006219 | 2925 | TACAGAAAAGTTTGGCCGG | 20.1 | Test | Training | 224 |
| 1333 | NM_006219 | 2346 | AATGAAGCCTTTGTGGCTG | 22.4 | Test | Training | 225 |
| 1334 | NM_006219 | 2044 | GTGCACATTCCTGCTGTCT | 79.0 | Test | Training | 226 |
| 1335 | NM_003600 | 1618 | CCTCCCTATTCAGAAAGCT | 84.2 | Test | Training | 227 |
| 1336 | NM_003600 | 650 | GACTTTGAAATTGGTCGCC | 52.1 | Test | Training | 228 |
| 1337 | NM_003600 | 538 | CACCCAAAAGAGCAAGCAG | 96.3 | Test | Training | 229 |
| 1338 | XM_294563 | 2703 | TAAGCCTGGTGGTGATCTT | 78.1 | Training | Training | 230 |
| 1339 | XM_294563 | 1701 | AAGGTCTTTACGCCAGTAC | 29.5 | Training | Training | 231 |
| 1340 | XM_294563 | 789 | GGAATGTATCCGAGCACTG | 73.5 | Training | Training | 232 |
| 1386 | NM_033360 | 493 | GGACTCTGAAGATGTACCT | 91.0 | Test | Training | 233 |
| 1387 | NM_033360 | 897 | GGCATACTAGTACAAGTGG | 84.8 | Test | Training | 234 |
| 1388 | NM_033360 | 704 | GAAAAGACTCCTGGCTGTG | 0.0 | Test | Training | 235 |
| 1389 | NM_024408 | 4735 | CTTTGAATGCCAGGGGAAC | 91.6 | Test | Training | 236 |
| 1390 | NM_024408 | 2674 | CCAAGGAACCTGCTTTGAT | 96.4 | Test | Training | 237 |
| 1391 | NM_024408 | 5159 | GACTCAGACCACTGCTTCA | 95.8 | Test | Training | 238 |
| 1392 | NM_000435 | 6045 | GCTGCTGTTGGACCACTTT | 0.0 | Test | Training | 239 |
| 1393 | NM_000435 | 5495 | TGCCAACTGAAGAGGATGA | 0.0 | Test | Training | 240 |
| 1394 | NM_000435 | 4869 | TGATCACTGCTTCCCCGAT | 0.0 | Test | Training | 241 |
| 1410 | AF308602 | 770 | ATATCGACGATTGTCCAGG | 36.7 | Test | Training | 242 |
| 1411 | AF308602 | 3939 | AGGCAAGCCCTGCAAGAAT | 81.3 | Test | Training | 243 |
| 1412 | AF308602 | 1644 | CACTTACACCTGTGTGTGC | 81.3 | Test | Training | 244 |
| 1581 | NM_005633 | 3593 | TATCAGACCGGACCTCTAT | 70.8 | Test | Training | 245 |
| 1582 | NM_005633 | 364 | ATTGACCACCAGGTTTCTG | 1.4 | Test | Training | 246 |
| 1583 | NM_005633 | 3926 | CTTACAAAAGGGAGCACAC | 66.9 | Test | Training | 247 |
| 1620 | NM_002388 | 1097 | GTCTCAGCTTCTGCGGTAT | 95.0 | Test | Training | 248 |
| 1621 | NM_002388 | 286 | AGGATTTTGTGGCCTCCAT | 94.6 | Test | Training | 249 |
| 1622 | NM_002388 | 2268 | TCCAGGTTGAAGGCATTCA | 92.5 | Test | Training | 250 |
| 1629 | NM_012193 | 3191 | TTGGCAAAGGCTCCTTGTA | 80.0 | Test | Test | 251 |
| 1630 | NM_012193 | 5335 | CCATCTGCTTGAGCTACTT | 85.0 | Test | Test | 252 |
| 1631 | NM_012193 | 2781 | GTTGACTTACCTGACGGAC | 43.1 | Test | Test | 253 |
| 1632 | NM_004380 | 3708 | GACATCCCGAGTCTATAAG | 85.3 | Test | Training | 254 |
| 1633 | NM_004380 | 339 | TGGAGGAGAATTAGGCCTT | 81.1 | Test | Training | 255 |
| 1634 | NM_004380 | 5079 | GCACAAGGAGGTCTTCTTC | 79.0 | Test | Training | 256 |
| 1641 | NM_017412 | 2331 | CAGATCACTCCAGGCATAG | 97.3 | Test | Training | 257 |
| 1643 | NM_017412 | 2783 | ATGTGTGGTGACTGCTTTG | 95.7 | Test | Training | 258 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 1695 | NM_001903 | 2137 | TGACATCATTGTGCTGGCC | 38.4 | Test | Training | 259 |
| 1696 | NM_001903 | 655 | CGTTCCGATCCTCTATACT | 97.9 | Test | Training | 260 |
| 1697 | NM_001903 | 3117 | TGACCAAAGATGACCTGTG | 40.1 | Test | Training | 261 |
| 1815 | NM_020168 | 3064 | GAGAAAGAATGGGGTCGGT | 85.0 | Training | Training | 262 |
| 1816 | NM_020168 | 681 | CGACATCCAGAAGTTGTCA | 86.1 | Training | Training | 263 |
| 1817 | NM_020168 | 1917 | TGAGGAGCAGATTGCCACT | 72.1 | Training | Training | 264 |
| 2502 | NM_000271 | 237 | GAGGTACAATTGCGAATAT | 87.0 | Training | Training | 265 |
| 2503 | NM_000271 | 559 | TACTACGTCGGACAGAGTT | 76.0 | Training | Training | 266 |
| 2504 | NM_000271 | 1783 | AACTACAATAACGCCACTG | 39.0 | Training | Training | 267 |
| 2505 | NM_000271 | 2976 | GCCACAGTCGTCTTGCTGT | 84.0 | Training | Training | 268 |
| 2512 | NM_005030 | 245 | GGGCGGCTTTGCCAAGTGC | 88.6 | Test | Test | 269 |
| 2513 | NM_005030 | 1381 | CACGCCTCATCCTCTACAA | 90.5 | Test | Test | 270 |
| 2514 | NM_005030 | 834 | GAGACCTACCTCCGGATCA | 91.0 | Test | Test | 271 |
| 2521 | NM_000314 | 1316 | CCCACCACAGCTAGAACTT | 93.0 | Training | Training | 272 |
| 2522 | NM_000314 | 1534 | CTATTCCCAGTCAGAGGCG | 89.0 | Training | Training | 273 |
| 2523 | NM_000314 | 2083 | CAGTAGAGGAGCCGTCAAA | 90.0 | Training | Training | 274 |
| 2524 | NM_006622 | 1928 | CAGTTCACTATTACGCAGA | 65.0 | Training | Training | 275 |
| 2525 | NM_006622 | 586 | TGTTACGAGATGACAGATT | 73.0 | Training | Training | 276 |
| 2526 | NM_006622 | 1252 | AACCCAGAGGATCGTCCCA | 70.0 | Training | Training | 277 |
| 2527 | NM_139164 | 200 | CTGTTTGGAGAAAACCCTC | 79.0 | Training | Training | 278 |
| 2528 | NM_139164 | 568 | GACAACCCAAACCAGAGTC | 71.0 | Training | Training | 279 |
| 2529 | NM_139164 | 488 | GTCTTGACTGGGATGAAAA | 66.0 | Training | Training | 280 |
| 2530 | NM_139164 | 578 | ACCAGAGTCTTTTGACAGG | 82.0 | Training | Training | 281 |
| 2546 | NM_014875 | 1090 | TAGACCACCCATTGCTTCC | 63.5 | Test | Training | 282 |
| 2547 | NM_014875 | 1739 | AGAGCCTTCGAAGGCTTCA | 73.2 | Test | Training | 283 |
| 2548 | NM_014875 | 3563 | GACCATAGCATCCGCCATG | 87.1 | Test | Training | 284 |
| 2602 | NM_002387 | 2655 | TAGCTCTGCTAGAGGAGGA | 71.0 | Test | Training | 285 |
| 2603 | NM_002387 | 1418 | ACAGAACGGCTGAATAGCC | 43.5 | Test | Training | 286 |
| 2604 | NM_002387 | 941 | GAGAATGAGAGCCTGACTG | 81.0 | Test | Training | 287 |
| 2605 | NM_016231 | 1683 | GGAAACAGAGTGCCTCTCT | 55.3 | Test | Training | 288 |
| 2606 | NM_016231 | 915 | CCACTCAGCTCAGATCATG | 82.3 | Test | Training | 289 |
| 2607 | NM_016231 | 737 | TCTGGTCTCTTGCAAAAGG | 30.3 | Test | Training | 290 |
| 2611 | NM_004380 | 4230 | ATTTTTGCGGCGCCAGAAT | 79.0 | Test | Training | 291 |
| 2612 | NM_004380 | 2197 | GAAAACGGAGGTCGCGTT | 85.9 | Test | Training | 292 |
| 2613 | NM_004380 | 5701 | GAAAACAAATGCCCCGTGC | 55.4 | Test | Training | 293 |
| 2614 | NM_005978 | 276 | TGGCACTCATCACTGTCAT | 91.8 | Test | Test | 294 |
| 2615 | NM_005978 | 229 | TGAGAACAGTGACCAGCAG | 91.9 | Test | Test | 295 |
| 2616 | NM_005978 | 369 | GGGCCCAGGACTGTTGATG | 94.5 | Test | Test | 296 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 2617 | NM_017412 | 3128 | AGAGATGGGCATTGTTTCC | 94.3 | Test | Training | 297 |
| 2618 | NM_017412 | 814 | GCTCATGGAGATGTTTGGT | 88.7 | Test | Training | 298 |
| 2619 | NM_017412 | 1459 | AGCATTGCTGTTTCACGCC | 93.1 | Test | Training | 299 |
| 2620 | NM_001654 | 1902 | TTGAGCTGCTGCAACGGTC | 67.2 | Test | Training | 300 |
| 2621 | NM_001654 | 1006 | GTCCCCACATTCCAAGTCA | 90.0 | Test | Training | 301 |
| 2622 | NM_001654 | 2327 | CCTCTCTGGAATTTGTGCC | 85.7 | Test | Training | 302 |
| 2623 | NM_002658 | 202 | CAAGTACTTCTCCAACATT | 87.2 | Test | Training | 303 |
| 2624 | NM_002658 | 181 | TGGAGGAACATGTGTGTCC | 0.0 | Test | Training | 304 |
| 2625 | NM_002658 | 436 | TTACTGCAGGAACCCAGAC | 0.0 | Test | Training | 305 |
| 2629 | NM_006218 | 1334 | TGGCTTTGAATCTTTGGCC | 3.5 | Test | Training | 306 |
| 2630 | NM_006218 | 2613 | AGGTGCACTGCAGTTCAAC | 53.8 | Test | Training | 307 |
| 2631 | NM_006218 | 1910 | TTCAGCTAGTACAGGTCCT | 78.0 | Test | Training | 308 |
| 2632 | NM_003161 | 1834 | TTGATTCCTCGCGACATCT | 88.3 | Test | Training | 309 |
| 2633 | NM_003161 | 1555 | GCTTTTCCCATGATCTCCA | 90.7 | Test | Training | 310 |
| 2634 | NM_003161 | 217 | CTTGGCATGGAACATTGTG | 61.4 | Test | Training | 311 |
| 2635 | NM_003391 | 2072 | GCCTCAGAAAGGGATTGCT | 79.1 | Test | Training | 312 |
| 2636 | NM_003391 | 1318 | GCTCTGGATGTGCACACAT | 60.5 | Test | Training | 313 |
| 2637 | NM_003391 | 1734 | GTGTCTCAAAGGAGCTTTC | 87.1 | Test | Training | 314 |
| 2641 | AF308602 | 4260 | ATTCAACGGGCTCTTGTGC | 0.0 | Test | Training | 315 |
| 2642 | AF308602 | 1974 | GATCGATGGCTACGAGTGT | 84.0 | Test | Training | 316 |
| 2643 | AF308602 | 5142 | CATCCCCTACAAGATCGAG | 41.6 | Test | Training | 317 |
| 2644 | NM_024408 | 8232 | GCAACTTTGGTCTCCTTTC | 91.0 | Test | Training | 318 |
| 2645 | NM_024408 | 10503 | GCAATTGGCTGTGATGCTC | 86.6 | Test | Training | 319 |
| 2646 | NM_024408 | 8643 | GAGACAAGTTAACTCGTGC | 89.4 | Test | Training | 320 |
| 2647 | NM_007313 | 4222 | TCCTGGCAAGAAAGCTTGA | 65.6 | Test | Training | 321 |
| 2648 | NM_007313 | 3237 | AAACCTCTACACGTTCTGC | 53.5 | Test | Training | 322 |
| 2649 | NM_007313 | 302 | CTAAAGGTGAAAAGCTCCG | 67.8 | Test | Training | 323 |
| 2650 | NM_000551 | 631 | GATCTGGAAGACCACCCAA | 70.9 | Test | Training | 324 |
| 2651 | NM_000551 | 4678 | CAGAACCCAAAAGGGTAAG | 0.0 | Test | Training | 325 |
| 2652 | NM_000551 | 4382 | AGGAAATAGGCAGGGTGTG | 4.3 | Test | Training | 326 |
| 2653 | NM_001903 | 1888 | AGCAGTGCTGATGATAAGG | 89.1 | Test | Training | 327 |
| 2654 | NM_001903 | 2606 | AAGCCATTGGTGAAGAGAG | 91.9 | Test | Training | 328 |
| 2655 | NM_001903 | 1583 | TGTGTCATTGCTCTCCAAG | 90.3 | Test | Training | 329 |
| 2656 | NM_002388 | 842 | GCAGATGAGCAAGGATGCT | 86.8 | Test | Training | 330 |
| 2657 | NM_002388 | 1754 | GTACATCCATGTGGCCAAA | 94.6 | Test | Training | 331 |
| 2658 | NM_002388 | 2642 | TGGGTCATGAAAGCTGCCA | 93.1 | Test | Training | 332 |
| 2662 | NM_005633 | 3251 | GAACACCGTTAACACCTCC | 31.2 | Test | Training | 333 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 2663 | NM_005633 | 2899 | ATAACAGGAGAGATCCAGC | 21.7 | Test | Training | 334 |
| 2664 | NM_005633 | 2607 | TGGTGTCCTTGAGGTTGTC | 75.1 | Test | Training | 335 |
| 2665 | NM_033360 | 329 | ACCTGTCTCTTGGATATTC | 81.4 | Test | Training | 336 |
| 2666 | NM_033360 | 529 | TAAATGTGATTTGCCTTCT | 47.8 | Test | Training | 337 |
| 2667 | NM_033360 | 585 | GAAGTTATGGAATTCCTTT | 94.2 | Test | Training | 338 |
| 2668 | NM_139049 | 745 | CACCATGTCCTGAATTCAT | 80.7 | Test | Training | 339 |
| 2669 | NM_139049 | 433 | TCAAGCACCTTCATTCTGC | 42.6 | Test | Training | 340 |
| 2670 | NM_139049 | 550 | CGAGTTTTATGATGACGCC | 79.9 | Test | Training | 341 |
| 2671 | NM_002086 | 555 | ATACGTCCAGGCCCTCTTT | 87.9 | Test | Test | 342 |
| 2672 | NM_002086 | 392 | TGCAGCACTTCAAGGTGCT | 36.9 | Test | Test | 343 |
| 2673 | NM_002086 | 675 | CGGGCAGACCGGCATGTTT | 92.6 | Test | Test | 344 |
| 2674 | NM_004958 | 5024 | GACATGAGAACCTGGCTCA | 77.8 | Test | Training | 345 |
| 2675 | NM_004958 | 2155 | CTTGCAGGCCTTGTTTGTG | 83.2 | Test | Training | 346 |
| 2676 | NM_004958 | 6955 | TAATACAGCTGGGGACGAC | 52.3 | Test | Training | 347 |
| 2677 | NM_012193 | 467 | AGAACCTCGGCTACAACGT | 71.5 | Test | Test | 348 |
| 2678 | NM_012193 | 473 | TCGGCTACAACGTGACCAA | 51.3 | Test | Test | 349 |
| 2679 | NM_012193 | 449 | TCCGCATCTCCATGTGCCA | 37.5 | Test | Test | 350 |
| 2680 | NM_005400 | 665 | TCACAAAGTGTGCTGGGTT | 43.9 | Test | Training | 351 |
| 2681 | NM_005400 | 2178 | CCAGGAGGAATTCAAAGGT | 41.6 | Test | Training | 352 |
| 2682 | NM_005400 | 1022 | GCTCACCATCTGAGGAAGA | 64.2 | Test | Training | 353 |
| 2686 | NM_001982 | 948 | TGACAGTGGAGCCTGTGTA | 65.8 | Test | Training | 354 |
| 2687 | NM_001982 | 1800 | CTTTCTGAATGGGGAGCCT | 61.7 | Test | Training | 355 |
| 2688 | NM_001982 | 2860 | TACACACACCAGAGTGATG | 0.0 | Test | Training | 356 |
| 2692 | NM_016195 | 5331 | ATGAAGGAGAGTGATCACC | 10.5 | Test | Training | 357 |
| 2693 | NM_016195 | 4829 | AATGGCAGTGAAACACCCT | 67.3 | Test | Training | 358 |
| 2694 | NM_016195 | 1480 | AAGTTTGTGTCCCAGACAC | 80.5 | Test | Training | 359 |
| 2695 | NM_000435 | 2107 | AATGGCTTCCGCTGCCTCT | 0.0 | Test | Training | 360 |
| 2696 | NM_000435 | 5193 | GAACATGGCCAAGGGTGAG | 15.5 | Test | Training | 361 |
| 2697 | NM_000435 | 7273 | GAGTCTGGGACCTCCTTCT | 0.0 | Test | Training | 362 |
| 2802 | NM_004523 | 46 | CCAGGGAGACTCCGGCCCC | 6.7 | Training | Test | 363 |
| 2803 | NM_004523 | 132 | GGGACCGTCATGGCGTCGC | 8.2 | Training | Test | 364 |
| 2804 | NM_004523 | 221 | ATTTAATTTGGCAGAGCGG | 0.0 | Training | Test | 365 |
| 2805 | NM_004523 | 322 | GCTCAAGGAAAACATACAC | 76.2 | Training | Test | 366 |
| 2806 | NM_004523 | 365 | TACTAAACAGATTGATGTT | 77.9 | Training | Test | 367 |
| 2807 | NM_004523 | 581 | TACTGATAATGGTACTGAA | 93.8 | Training | Test | 368 |
| 2808 | NM_004523 | 716 | AGGAGTGATAATTAAAGGT | 84.8 | Training | Test | 369 |
| 2809 | NM_004523 | 852 | GTTTTCTCTGTTACAATAC | 85.4 | Training | Test | 370 |
| 2810 | NM_004523 | 995 | TGGAAATATAAATCAATCC | 0.0 | Training | Test | 371 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 2811 | NM_004523 | 1085 | ACTAACTAGAATCCTCCAG | 0.0 | Training | Test | 372 |
| 2812 | NM_004523 | 1174 | AAACTCTGAGTACATTGGA | 81.9 | Training | Test | 373 |
| 2813 | NM_004523 | 1375 | TAACTGTTCAAGAAGAGCA | 14.1 | Training | Test | 374 |
| 2814 | NM_004523 | 1570 | AAGAAGAATATATCACATC | 0.0 | Training | Test | 375 |
| 2815 | NM_004523 | 1706 | AGTTGACCAACACAATGCA | 86.0 | Training | Test | 376 |
| 2816 | NM_004523 | 2197 | TACATGAACTACAAGAAAA | 90.0 | Training | Test | 377 |
| 2817 | NM_004523 | 2858 | GACTAAGCTTAATTGCTTT | 87.0 | Training | Test | 378 |
| 2818 | NM_004523 | 3089 | GGGGCAGTATACTGAAGAA | 64.5 | Training | Test | 379 |
| 2819 | NM_004523 | 3878 | TTCTTGTATATTATTAAGT | 0.0 | Training | Test | 380 |
| 2820 | NM_004523 | 4455 | TCTATAATTTATATTCTTT | 9.3 | Training | Test | 381 |
| 2821 | NM_004523 | 4648 | TACAAAGAATAAATTTTCT | 23.5 | Training | Test | 382 |
| 2823 | NM_005030 | 45 | CAGCGCAGCTTCGGGAGCA | 72.1 | Training | Test | 383 |
| 2824 | NM_005030 | 131 | CGGAGTTGCAGCTCCCGGA | 85.7 | Training | Test | 384 |
| 2825 | NM_005030 | 303 | GGCAAGATTGTGCCTAAGT | 80.1 | Training | Test | 385 |
| 2826 | NM_005030 | 346 | GGGAGAAGATGTCCATGGA | 100.0 | Training | Test | 386 |
| 2827 | NM_005030 | 432 | GACTTCGTGTTCGTGGTGT | 89.3 | Training | Test | 387 |
| 2828 | NM_005030 | 519 | GCCCGATACTACCTACGGC | 86.2 | Training | Test | 388 |
| 2829 | NM_005030 | 648 | GGACTGGCAACCAAAGTCG | 86.7 | Training | Test | 389 |
| 2830 | NM_005030 | 777 | TGTATCATGTATACCTTGT | 84.3 | Training | Test | 390 |
| 2831 | NM_005030 | 821 | TTCTTGCCTAAAAGAGACC | 26.8 | Training | Test | 391 |
| 2832 | NM_005030 | 907 | TCCAGAAGATGCTTCAGAC | 90.8 | Training | Test | 392 |
| 2833 | NM_005030 | 952 | ACGAGCTGCTTAATGACGA | 87.7 | Training | Test | 393 |
| 2834 | NM_005030 | 1038 | TCGATTGCTCCCAGCAGCC | 31.4 | Training | Test | 394 |
| 2835 | NM_005030 | 1082 | CACAGTCCTCAATAAAGGC | 62.9 | Training | Test | 395 |
| 2836 | NM_005030 | 1214 | CAATGCCTCCAAGCCCTCG | 0.0 | Training | Test | 396 |
| 2837 | NM_005030 | 1300 | AGTGGGTGGACTATTCGGA | 84.9 | Training | Test | 397 |
| 2838 | NM_005030 | 1515 | TACATGAGCGAGCACTTGC | 20.3 | Training | Test | 398 |
| 2839 | NM_005030 | 1860 | CTCAAGGCCTCCTAATAGC | 74.2 | Training | Test | 399 |
| 2840 | NM_005030 | 1946 | CCGCGGTGCCATGTCTGCA | 79.7 | Training | Test | 400 |
| 2841 | NM_005030 | 2075 | CCCCTCCCCCTCAACCCCA | 34.6 | Training | Test | 401 |
| 3041 | NM_014875 | 4629 | ATTTTCTAGAAAACGGTAA | 91.8 | | | 402 |
| 3042 | NM_014875 | 77 | GAGGGGCGAAGTTTCGGCA | 71.2 | | | 403 |
| 3043 | NM_014875 | 243 | CTGGGACCGGGMGCCGGA | 0.0 | | | 404 |
| 3044 | NM_014875 | 5094 | CTTCTACTTCTGTTGGCAG | 85.9 | | | 405 |
| 3045 | NM_014875 | 4354 | ACTTACTATTCAGACTGCA | 85.7 | | | 406 |
| 3046 | NM_014875 | 524 | GCCCTCACCCACAGTAGCC | 68.1 | | | 407 |
| 3047 | NM_014875 | 5349 | CAGAGGAATGCACACCCAG | 73.6 | | | 408 |

TABLE II-continued

A library of 377 siRNA

| BioID | accession number | start position | 19mer sequence | % silencing | Set 1 | Set 2 | SEQ ID NO |
|---|---|---|---|---|---|---|---|
| 3048 | NM_014875 | 4824 | GATTGATTAGATCTCTTGA | 91.3 | | | 409 |
| 3049 | NM_014875 | 3014 | GTGAGTATTATCCCAGTTG | 41.5 | | | 410 |
| 3050 | NM_014875 | 2959 | ATCTGGGGTGCTGATTGCT | 46.3 | | | 411 |
| 3051 | NM_014875 | 1514 | GTGACAGTGGCAGTACGCG | 67.7 | | | 412 |
| 3052 | NM_014875 | 1114 | TCAGACTGAAGTTGTTAGA | 80.8 | | | 413 |
| 3053 | NM_014875 | 2079 | GTTGGCTAGAATTGGGAAA | 91.8 | | | 414 |
| 3054 | NM_014875 | 3560 | GAAGACCATAGCATCCGCC | 74.8 | | | 415 |

Tables III show alignments of IGF1R-73 early kinetics genes with the antisense strand of IGF1R-73. Tables IVA and B show alignments of IGF1R-73 early kinetics genes with the sense and antisense strand of IGF1R-73, respectively. Tables VA and B show alignments of MAPK14-193 early kinetics genes with the sense and antisense strand of MAPK4-193, respectively. In these tables, UPPERCASE indicates complementary base, lowercase indicates non-complementary base, GRAY-SHADED indicates the position of gap in alignment on the siRNA strand, Contig start indicates the start position of longest contiguous stretch of alignment, and Contig length indicates the length of longest contiguous stretch of alignment.

TABLE III

Alignments of IGF1R-73 early kinetics genes
with the antisense strand of IGF1R-73

IGF1R-73 antisense strand sequence
G A G G T A A C A G A G G T C A G C A

| NM_006070 | t A G G c t t g t t g G G T C A G C g |
| NM_006291 | a g c a T c t t g G A c G T C A G C A |

TABLE III-continued

Alignments of IGF1R-73 early kinetics genes
with the antisense strand of IGF1R-73

IGF1R-73 antisense strand sequence
G A G G T A A C A G A G G T C A G C A

| NM_001814 | t A t a a A g a A G A G G g C A G C A |
| NM_014320 | c A G G T A A C A G A G G a C A G t A |
| AF167706 | c A G a a g c C A G A G c T C A G t A |
| AF179224 | t g G c c t t g g c A G G T C A G C A |
| AK000808 | a g a G g A g g A t g G G T C A G C c |
| NM_005765 | t g a G T A A C A G A G G a C A G C t |
| NM_019086 | G A G G g A A C A G A G G T C A G g A |

TABLE IVA

Alignments of IGF1R-73 12 hour signature genes, showing
identity to the sense strand of IGF1R-73
IGF1R-73 sense strand sequence

| accession | T G C T G A C C T C T G T T A C C T C | contig start | contig length |
|---|---|---|---|
| Contig45859_RC | − − − − − A t a a t c a T T A C C T t | 8 | 6 |
| NM_005638 | T a C T G g C a T C T G T T A t C T a | 9 | 7 |
| NM_003369 | a G C T G A g C T C T G C T g t a C t | 2 | 5 |
| Z49105 | c c C c t c a C T C T G T T t C C T g | 8 | 7 |
| AF070648 | a t t a c c a a c C T G T T A C C T a | 10 | 9 |
| NM_003721 | c G C T G A C C T C a c c a C g a a | 2 | 9 |
| AF167706 | g G g a G A g t g C T G T g A C C T C | 15 | 5 |
| AF072928 | a G C a G A − C T C T G c T A C C c g | 8 | 5 |
| AK000745 | T G t T a A C a T C T G T T t C a g g | 9 | 6 |
| NM_014637 | T G C T G c C C T C a t a g c a g a g | 1 | 5 |
| AK001846 | T G g g a g C t T C T G T T A a C T t | 9 | 7 |

TABLE IVA-continued

Alignments of IGF1R-73 12 hour signature genes, showing identity to the sense strand of IGF1R-73

IGF1R-73 sense strand sequence

| accession | T G C T G A C C T C T G T T A C C T C | contig start | contig length |
|---|---|---|---|
| NM_005765 | a t g g a t t g a a T G T T A C C T g | 11 | 8 |
| NM_006358 | a a C T G A C a g C T G c c A C C T t | 3 | 5 |
| NM_004157 | g c C T G A C C T C g t c g A a t T C | 3 | 8 |
| NM_014814 | a G C T G A a C T C T t c c t t g a C | 2 | 5 |
| NM_019086 | T t t T t c t C a C T G T T A C t g a | 10 | 7 |
| NM_003011 | c a C C G A g C T C T G T g g g a a a | 8 | 6 |
| NM_017443 | a c C T t A C ▨ T C T G c T A C t g t | 9 | 5 |
| NM_006804 | a G C T G A C C C g a G a c t t g g a | 2 | 7 |
| AK000808 | c G C g t t a a c C T G T T c C C T t | 10 | 5 |
| NM_016031 | g G C T a c C C T C T G a T g g g g t | 7 | 6 |
| Contig1462_RC | a a a g a A g C T C T G T c A C a a t | 8 | 6 |
| NM_005321 | c c a g t g C C T C T G c T t C C g g | 7 | 6 |
| NM_013397 | c a t T G A C C T C ▨ G g c A C C T C | 3 | 7 |
| NM_003765 | c G a a G A C C c C T t T T t g T a | 5 | 4 |
| Contig47067_RC | g a a T c t t a a g T G T T A C a g g | 11 | 6 |
| Contig49512_RC | T G C T G A t g c t T c c a g t a g a | 1 | 6 |
| Contig47994_RC | T t C c t A g t T C T G T T t t c T G | 9 | 6 |
| Contig48185_RC | a a g a G c C C T − T t T T A C C T g | 13 | 6 |

TABLE IV B

Alignments of IGF1R-73 12 hour signature genes, showing identity to the antisense strand of IGF1R-73

IGF1R-73 antisense strand sequence

| accession | G A G G T A A C A G A G G T C A G C A | contig Start | contig length |
|---|---|---|---|
| NM_019086 | G A G G g A A C A G A G G T C A G g A | 6 | 12 |
| NM_005765 | t g a G T A A C A G A G G a C A G C t | 4 | 10 |
| NM_016031 | c A c a c A g a A G A G G T C A G C A | 9 | 11 |
| NM_014637 | c t a a g g A C A G A G G T C A G a t | 7 | 11 |
| NM_003011 | G A G t T A g g A G A G G T C A t C A | 9 | 8 |
| AK000745 | t g a a a t t a A G A G G T C A G C A | 9 | 11 |
| AF070648 | c A a c T g A a t G A G G T C A G C A | 10 | 10 |
| NM_005638 | G A G G T g A C A G A G c a g A t t c | 7 | 6 |
| NM_003369 | G A G G T t A C t G c a G T C A G a t | 1 | 5 |
| AF072928 | c g a a c t A t A G A G G g C A G C A | 9 | 5 |

TABLE IV B-continued

Alignments of IGF1R-73 12 hour signature genes,
showing identity to the antisense strand of IGF1R-73
IGF1R-73 antisense strand sequence

| accession | G A G G T A A C A G A G G T C A G C A | contig Start | contig length |
|---|---|---|---|
| NM_014814 | t A c t a A A C A G A G t T C A a a A | 6 | 7 |
| AF167706 | c A G a a g c C A G A G c T C A G t A | 8 | 5 |
| AK001846 | t A c a a t g t A t t G G T C A G C A | 12 | 8 |
| NM_017443 | c A G a T c A C A G A G G — C A G C c | 7 | 7 |
| NM_006358 | t c t G g g t C A a A G G T C A a C A | 11 | 6 |
| NM_003765 | G g a a T A A C A G A G a g a t a C t | 5 | 8 |
| Z49105 | a t t t a t g a A G A G a T C A G C g | 14 | 5 |
| NM_004157 | t g a t g A A C A G A G a T ▨ A G a c | 6 | 7 |
| AK000808 | a g a G g A g g A t g G G T C A G C c | 12 | 7 |
| NM_003721 | c c G G T g t C A G A G G g C c c g c | 8 | 6 |
| Contig1462_RC | a t a t a c A C A t t t G T C A G C A | 13 | 7 |
| NM_006804 | a t a c c A A C A c A G G c a t c C g | 6 | 4 |
| NM_005321 | c A a G g c c a A G A a G c C A G C A | 15 | 5 |
| Contig47067_RC | t A c a c t t t A a A a G T C A G C A | 13 | 7 |
| Contig49512_RC | G A G G c A A C A a g a t T a A a a A | 1 | 4 |
| Contig47994_RC | G t c t g g A a A G A G c T C A t C t | 9 | 4 |
| Contig48185_RC | G A G a a A A C A G t c a a a t t t A | 6 | 5 |
| Contig45859_RC | t t a G T t t a A a A G G T C A a t c | 11 | 6 |
| NM_013397 | G A G t T ▨ t C A G A G G g C — — — — | 8 | 6 |

TABLE VA

Alignments of MAPK14-193 12 hour signature genes,
showing identity to the sense strand of MAPK14-193
MAPK14-193 sense strand sequence

| accession | C C T A C A G A G A A C T G C G G T T | contig start | contig length |
|---|---|---|---|
| NM_002271 | g C T A C A G A G A A C T G C a t c T | 2 | 14 |
| NM_017748 | t t T A C A G A G A A C T t C G G T a | 3 | 11 |
| NM_021033 | t C T A C A G A G A A C T G C a G c c | 2 | 14 |
| NM_004165 | a g g c C t c A G A A C T G C G G g T | 8 | 10 |
| NM_004583 | g C T A C A G A G g c a g G C c a g c | 2 | 8 |
| NM_013242 | a a T A t t t c t t c C T G C G G T T | 12 | 8 |
| NM_002946 | g a a g C A G g G A A C T t t G G T g | 9 | 5 |
| NM_002200 | t C T A C A G c c A g C T G g a G g c | 2 | 6 |

TABLE VB

Alignments of MAPK14-193 12 hour signature genes, showing identity to the antisense strand of MAPK14-193 MAPK14-193 antisense strand sequence

| accession | A A C C G C A G T T C T C T G T A G G | contig start | contig length |
|---|---|---|---|
| NM_002271 | g g C C G C c G T T C T C c t a A G a | 8 | 6 |
| NM_021033 | A A a C G a A t T T C a C T G T g t a | 13 | 4 |
| NM_013242 | g t a a G C A G T c C T g T G a g t G | 5 | 5 |
| NM_004583 | g A C a a C A G T T t g C T G T t c a | 6 | 5 |
| NM_004165 | c c t C t C g G T T C T C T a g g t c | 8 | 7 |
| NM_002946 | g t a C G C – G T T t T C T G g A G c | 12 | 4 |
| NM_002200 | c A C C G C A G a c a g a c c c t c | 2 | 7 |
| NM_017748 | c c a g a a A a c T C T C T G c A G a | 10 | 6 |

Strand preference was evaluated using the polling method and the 3'-biased method based on the alignment data of IGF1R-73 and MAPK14-193, and shown in Table VI and VII, respectively.

TABLE VI

Polling method of predicting strand bias

|  | MAPK14-193 |  | IGF1R-73 |  |
|---|---|---|---|---|
| timepoint (hours) | 12 | 24 | 12 | 24 |
| signature genes | 11 | 96 | 29 | 198 |
| antisense-identity score | 3 | 87 | 45 | 266 |
| sense-identity score | 45 | 142 | 23 | 164 |
| expected score | 5 | 47 | 14 | 97 |

The expected score corresponds to signature size and was calculated from the mean score per gene for 377 siRNAs (Table II) aligned with 24,975 mRNA sequences. The mean score per gene was 0.491, with a standard deviation of 0.0454.

It is seen that the sense-identity score exceeded the antisense-identity score at 12 and 24 hours for MAPK14-193. This corresponded to excess off-target activity of the antisense strand, as alignments with identity to the sense strand are complementary to the antisense strand of the siRNA and are expected to hybridize with it in the cell. At 12 hours, only the sense-identity score was above background, indicating that the direct off-target signature of this siRNA was likely to be due to the activity of the antisense strand. At 24 hours, both strands scored above background, presumably due to the onset of secondary regulations. However excess sense-identity was still detectable.

The antisense-identity score exceeded the sense-identity score at 12 and 24 hours for IGF1R-73. This corresponded to excess off-target activity of the sense strand, as alignments with identity to the antisense strand are complementary to the sense strand of the siRNA and are expected to hybridize with it in the cell. At 12 hours, the antisense-identity score was well above background, indicating that the majority of the direct off-target signature of this siRNA was likely to be due to the activity of the sense strand. The sense-identity score was slightly above background, which was not unexpected as the antisense strand showed weak silencing of the intended target and was thus known to be active as well. At 24 hours, both strands scored above background, presumably aided by the contributions of secondary regulations. However excess antisense-identity was still detectable.

TABLE VII

3'-biased method of predicting strand bias

|  | MAPK14-193 |  | IGF1R-73 |  |
|---|---|---|---|---|
| timepoint (hours) | 12 | 24 | 12 | 24 |
| signature genes | 11 | 96 | 29 | 198 |
| antisense-identity score | 0 | 9 | 10 | 58 |
| sense-identity score | 3 | 19 | 2 | 20 |
| expected score | 1 | 9 | 3 | 19 |

The expected score corresponded to signature size and was calculated from the mean score per gene for 377 siRNAs (Table II) aligned with 24,975 mRNA sequences. The mean score per gene was 0.0945, with a standard deviation of 0.0221.

It is seen that the sense-identity score exceeds the antisense-identity score at 12 and 24 hours for MAPK14-193. This corresponds to excess off-target activity of the antisense strand, as alignments with identity to the sense strand are complementary to the antisense strand of the siRNA and are expected to hybridize with it in the cell. At both 12 and 24 hours, only the sense-identity score is above background, indicating that the direct off-target signature of this siRNA is likely to be due to the activity of the antisense strand.

The antisense-identity score exceeds the sense-identity score at 12 and 24 hours for IGF1R-73. This corresponds to excess off-target activity of the sense strand, as alignments with identity to the antisense strand are complementary to the sense strand of the siRNA and are expected to hybridize with it in the cell. At 12 hours, only the antisense-identity score is above background, indicating that the direct off-target signature of this siRNA is likely to be due to the activity of the sense strand. The sense-identity score is below background at 12 hours and is not detected as contributing to the direct signature by this method. At 24 hours, both strands score above background, presumably aided by the contributions of secondary regulations. However excess antisense-identity score is still detectable.

In comparison with the polling method, the 3'-biased method appears relatively insensitive to detections due to secondary regulations or weak contributions by one of the siRNA strands.

6.4. Example 4

Base Composition Models for Prediction of Strand Preference of siRNAS

The mean difference in G/C content between good and bad siRNAs provides a model for G/C PSSMs which classify siRNA functional and resistant motifs. As it is known that both strands of the siRNA can be active (see, e.g., Elbashir et al., 2001, Genes Dev. 15:188-200), it was of interest to discover how well the G/C contents of both sense and antisense strands of siRNAs fit the model of siRNA functional target motif G/C content derived from the mean difference in G/C content between good and bad siRNAs. To this end, the reverse complements of good and bad siRNAs were examined. These reverse complements correspond to the hypothetical perfect match target sites for the sense strands of the siRNA duplexes. The reverse complements were compared to the actual good and bad siRNAs, represented by the actual perfect match target sites of the antisense strands of the siRNA duplexes.

FIG. 13A shows the difference between the mean G/C content of the reverse complements of bad siRNAs with the mean G/C content of the bad siRNAs themselves, within the 19mer siRNA duplex region. The difference between the mean G/C content of good and bad siRNAs is shown for comparison. The curves are smoothed over a window of 5 (or portion of a window of 5, at the edges of the sequence).

FIG. 13B shows the difference between the mean G/C content of the reverse complements of good siRNAs with the mean G/C content of bad siRNAs, within the 19mer siRNA duplex region. The difference between the mean G/C content of good and bad siRNAs is shown for comparison. The curves are smoothed over a window of 5 (or portion of a window of 5, at the edges of the sequence).

The reverse complements of bad siRNAs were seen to be even more different from the bad siRNAs themselves than are good siRNAs. On the average, the reverse complements of bad siRNAs had even stronger G/C content at the 5' end than the good siRNAs did and were similar in G/C content to good siRNAs at the 3' end. In contrast, the reverse complements of good siRNAs were seen to be substantially more similar to bad siRNAs than the good siRNAs were. On average, the reverse complements of good siRNAs hardly differed from bad siRNAs in G/C content at the 5' end and were only slightly less G/C rich than bad siRNAs at the 3' end.

These results appear to imply that the G/C PSSMs are distinguishing siRNAs with strong sense strands as bad siRNAs from siRNAs with weak sense strands as good siRNAs. An siRNA whose G/C PSSM score is greater than the G/C PSSM score of its reverse complement is predicted to have an antisense strand that is more active than its sense strand. In contrast, an siRNA whose G/C PSSM score is less than the G/C PSSM score of its reverse complement is predicted to have a sense strand that is more active than its antisense strand.

It has been shown that increased efficacy corresponds to greater antisense strand activity and lesser sense strand activity. Thus the G/C PSSMs of this invention would appear to distinguish good siRNAs with greater efficacy due to dominant antisense strand activity ("antisense-active" siRNAs) from siRNAs with dominant sense strand activity ("sense-active" siRNAs).

The relevance of comparison of G/C PSSMs of siRNAs and their reverse complements for prediction of strand bias was tested by comparison with estimation of strand bias from siRNA expression profiles by the 3'-biased method.

siRNAs and their reverse complements were scored using the smoothed G/C content difference between good and bad siRNAs within the 19mer, shown in FIG. 13A, as the weight matrix. The G/C PSSM score of each strand was the dot product of the siRNA strand G/C content with the G/C content difference matrix, following the score calculation method of curve model PSSMs.

siRNAs were called sense-active by the 3'-biased method of expression profile analysis if the antisense-identical score exceeded the sense-identical score. siRNAs were called sense-active by the G/C PSSM method if their reverse complement G/C PSSM score exceeded their own G/C PSSM score.

In FIG. 14, siRNAs were binned by measured silencing efficacy, and the frequency of sense-active calls by the expression profile and G/C PSSM methods was compared. Although these techniques are based on distinct analyses, the agreement is quite good. Both show that a higher proportion of low-silencing siRNAs vs. high-silencing siRNAs are predicted to be sense active. The correlation coefficient for (siRNA G/C PSSM score–reverse complement G/C PSSM score) vs. $\log_{10}$ (sense-identity score/antisense-identity score) is 0.59 for the set of 61 siRNAs binned in FIG. 14.

6.5. Example 5

Sense Strand Modification Alters Specificity of Sense-Active siRNA

This example illustrates that inactivation of the siRNA strand that is active in off-target silencing may improve the specificity of the siRNA.

FIG. 15 shows that sense strand modification alters specificity of "sense-active" siRNA. siRNAs were transfected into HeLa cells at a concentration of 100 nM. RNA was extracted 12 hours post-transfection and profiled against RNA from mock-transfected cells. On-target siRNAs contained two 2'-o-methyl substitutions in the sense strand to inactivate that strand and prevent it from functioning in gene silencing. The signature of siRNA 71, previously determined to be anti-sense-active, was not changed by the sense strand inactivation. In contrast, the signature of the siRNA 73, in which both strands are active, was significantly altered by sense-strand inactivation. In this situation, the sense strand was prevented from functioning in gene silencing, and potentially prevented from interacting with RISC, thus enabling the antisense strand to become dominant. This result indicates that chemical inactivation of the sense strand can alter the off-target signature of sense-active siRNAs, but does not eliminate it.

FIG. 16 shows strand bias in off-target regulation. siRNAs were aligned with signature genes. Bias towards alignment with the sense or antisense strands was determined by comparison of contiguous alignment lengths. Expected score for a random set is shown in gray. For siRNA 73, the signatures for the unmodified siRNA show identity to the antisense strand, indicating silencing due to the sense strand. With the sense-inactivated version of this siRNA, the signature genes now show identity to the sense strand, indicating silencing due to activity of the antisense strand. This verifies that both strands are functional for siRNA 73, with the sense strand being dominant. Inactivation of this strand allows the antisense strand to become dominant. For siRNA 71, signature genes show identity to the sense strand, verifying that the antisense strand is preferentially active in this duplex, and chemical inactivation of the sense strand does not alter this signature.

FIG. 17 shows that sense strand modification increases potency of "sense-active" siRNA. siRNA titration curve was used to assess potency, defined as ability to maintain silencing efficacy at lower concentration. siRNAs were transfected into HeLa cells at the indicated concentrations. RNA was extracted 24 hours post-transfection, and on-target silencing was measured by Real-time PCR. The sense-active siRNA (solid black line) showed decreased potency relative to the antisense-active siRNA (solid gray line.) This assay measures on-target silencing, which is a function of the activity of the antisense strand. The dominant activity of the sense strand in duplex 73 interfered with the activity of the antisense strand, thus limiting both potency and maximal efficacy. Chemical inactivation of the sense strand of this duplex significantly increased both potency and maximal efficacy (dashed black line,) presumably by freeing RISC for association with the antisense strand. This suggests that inactivation of the sense strand is one mechanism to achieve more potent siRNAs for more effective target gene silencing.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of designing a small interfering RNA ("siRNA") for silencing a first gene but not a second gene in a eukaryotic cell by RNA interference, comprising selecting an siRNA sequence that is characterized as:

(a) comprising a central contiguous nucleotide sequence of at least 11 nucleotides that is (i) identical to a sequence of a transcript of said first gene or (ii) identical to the reverse complement of a sequence of a transcript of said first gene;

(b) lacking any central contiguous nucleotide sequence of more than 10 nucleotides that is identical to a sequence of a transcript of said second gene and lacking any central contiguous nucleotide sequence of more than 10 nucleotides that is identical to the reverse complement of a sequence of a transcript of said second gene; and (c) lacking any 3' end contiguous nucleotide sequence of 8 or more nucleotides that is identical to a sequence of said transcript of said second gene and lacking any 3' end contiguous nucleotide sequence of 8 or more nucleotides that is identical to the reverse complement of a sequence of a transcript of said second gene;

said central contiguous nucleotide sequence being in the central region of said siRNA; said 3' end contiguous nucleotide sequence terminating within 3 nucleotides of the 3' end of said siRNA; wherein said selecting step is performed by a suitably programmed computer.

2. The method of claim 1, wherein said selecting is for an siRNA that is characterized as lacking any central contiguous nucleotide sequence of greater than 8 nucleotides in length that is identical to a sequence of said transcript of said second gene and lacking any central contiguous nucleotide sequence of greater than 8 nucleotides that is identical to the reverse complement of a sequence of a transcript of said second gene.

3. A method of designing a siRNA for silencing a first gene but not a second gene in a eukaryotic cell by RNA interference, comprising selecting an siRNA that is characterized as:
- (a) comprising a 3' end contiguous nucleotide sequence of 8 or more nucleotides that is (i) identical to a sequence of a transcript of said first gene or (ii) identical to the reverse complement of a sequence of a transcript of said first gene;
- (b) lacking any central contiguous nucleotide sequence of more than 10 nucleotides that is identical to a sequence of a transcript of said second gene and lacking any central contiguous nucleotide sequence of more than 10 nucleotides that is identical to the reverse complement of a sequence of a transcript of said second gene; and
- (c) lacking any 3' end contiguous nucleotide sequence of 8 or more nucleotides that is identical to a sequence of said transcript of said second gene and lacking any 3' end contiguous nucleotide sequence of 8 or more nucleotides that is identical to the reverse complement of a sequence of a transcript of said second gene;

said central contiguous nucleotide sequence being in the central region of said siRNA; said 3' end contiguous nucleotide sequence terminating within 3 nucleotides of the 3' end of said siRNA; wherein said selecting step is performed by a suitably programmed computer.

4. The method of claim 3, wherein said selecting is for an siRNA that is characterized as lacking any central contiguous nucleotide sequence of greater than 8 nucleotides in length that is identical to a sequence of said transcript of said second gene and lacking any central contiguous nucleotide sequence of greater than 8 nucleotides that is identical to the reverse complement of a sequence of a transcript of the second gene.

5. The method of claim 1 wherein said central contiguous nucleotide sequence in (a) is 11-15 nucleotides in length.

6. The method of claim 5, wherein said central contiguous nucleotide sequence in (a) is 14-15 nucleotides in length.

7. The method of claim 5, wherein said central contiguous nucleotide sequence in (a) is 13 nucleotides in length.

8. The method of claim 5, wherein said central contiguous nucleotide sequence in (a) is 12 nucleotides in length.

9. The method of claim 5, wherein said central contiguous nucleotide sequence in (a) is 11 nucleotides in length.

10. The method of claim 3, wherein said 3' end contiguous nucleotide sequence in (a) is 9-15 nucleotides in length.

11. The method of claim 10, wherein said 3' end contiguous nucleotide sequence in (a) is 9-12 nucleotides in length.

12. The method of claim 11, wherein said 3' end contiguous nucleotide sequence in (a) is 10 nucleotides in length.

13. The method of claim 11, wherein said 3' end contiguous nucleotide sequence in (a) is 9 nucleotides in length.

14. A computer program product for use in conjunction with a computer system, the computer program product comprising a computer readable storage medium and a computer program mechanism embedded therein, the computer program mechanism being for designing an siRNA for silencing a first gene but not a second gene in a eukaryotic cell by RNA interference, the computer program mechanism comprising executable instructions for performing a method comprising selecting an siRNA sequence that is characterized as:
- (a) comprising a central contiguous nucleotide sequence of at least 11 nucleotides that is (i) identical to a sequence of a transcript of said first gene or (ii) identical to the reverse complement of a sequence of a transcript of said first gene;
- (b) lacking any central contiguous nucleotide sequence of more than 10 nucleotides that is identical to a sequence of a transcript of said second gene and lacking any central contiguous nucleotide sequence of more than 10 nucleotides that is identical to the reverse complement of a sequence of a transcript of said second gene; and
- (c) lacking any 3' end contiguous nucleotide sequence of 8 or more nucleotides that is identical to a sequence of said transcript of said second gene and lacking any 3' end contiguous nucleotide sequence of 8 or more nucleotides that is identical to the reverse complement of a sequence of a transcript of said second gene;

said central contiguous nucleotide sequence being in the central region of said siRNA; said 3' end contiguous nucleotide sequence terminating within 3 nucleotides of the 3' end of said siRNA.

15. The computer program product of claim 14, wherein said selecting is for an siRNA that is characterized as lacking a any central contiguous nucleotide sequence of greater than 8 nucleotides in length that is identical to a sequence of said transcript of said second gene and lacking any central contiguous nucleotide sequence of greater than 8 nucleotides that is identical to the reverse complement of a sequence of a transcript of said second gene.

16. The computer program product of claim 14 wherein said central contiguous nucleotide sequence in (a) is 11-15 nucleotides in length.

17. The computer program product of claim 16, wherein said central contiguous nucleotide sequence in (a) is 14-15 nucleotides in length.

18. The computer program product of claim 16, wherein said central contiguous nucleotide sequence in (a) is 13 nucleotides in length.

19. The computer program product of claim 16, wherein said central contiguous nucleotide sequence in (a) is 12 nucleotides in length.

20. The computer program product of claim 16, wherein said central contiguous nucleotide sequence in (a) is 11 nucleotides in length.

21. A computer program product for use in conjunction with a computer system, the computer program product comprising a computer readable storage medium and a computer program mechanism embedded therein, the computer program mechanism being for designing an siRNA for silencing a first gene but not a second gene in a eukaryotic cell by RNA interference, the computer program mechanism comprising executable instructions for performing a method comprising selecting an siRNA sequence that is characterized as:
- (a) comprising a 3' end contiguous nucleotide sequence of 8 or more nucleotides that is (i) identical to a sequence of said transcript of said first gene or (ii) identical to the reverse complement of a sequence of a transcript of said first gene;
- (b) lacking any central contiguous nucleotide sequence of more than 10 nucleotides that is identical to a sequence of a transcript of said second gene and lacking any central contiguous nucleotide sequence of more than 10 nucleotides that is identical to the reverse complement of a sequence of a transcript of said second gene; and
- (c) lacking any 3' end contiguous nucleotide sequence of 8 or more nucleotides that is identical to a sequence of said transcript of said second gene and lacking any 3' end contiguous nucleotide sequence of 8 or more nucleotides that is identical to the reverse complement of a sequence of a transcript of said second gene;

said central contiguous nucleotide sequence being in the central region of said siRNA; said 3' end contiguous nucleotide sequence terminating within 3 nucleotides of the 3' end of said siRNA.

22. The computer program product of claim 21, wherein said selecting is of an siRNA that is characterized as lacking any central contiguous nucleotide sequence of greater than 8 nucleotides in length that is identical to a sequence of said transcript of said second gene and lacking any central contiguous nucleotide sequence of greater than 8 nucleotides that is identical to the reverse complement of a sequence of a transcript of the second gene.

23. The computer program product of claim 21, wherein said 3' end contiguous nucleotide sequence in (a) is 9-15 nucleotides in length.

24. The computer program product of claim 23, wherein said 3' end contiguous nucleotide sequence in (a) is 9-12 nucleotides in length.

25. The computer program product of claim 24, wherein said 3' end contiguous nucleotide sequence in (a) is 10 nucleotides in length.

26. The computer program product of claim 24, wherein said 3' end contiguous nucleotide sequence in (a) is 9 nucleotides in length.

27. A computer system for designing an siRNA for silencing a first gene but not a second gene in a eukaryotic cell by RNA interference, the computer system comprising:
a central processing unit;
a memory, coupled to the central processing unit, the memory storing one or more programs that cause the central processing unit to perform a method comprising selecting an siRNA sequence that is characterized as:
(a) comprising a central contiguous nucleotide sequence of at least 11 nucleotides that is (i) identical to a sequence of a transcript of said first gene or (ii) identical to the reverse complement of a sequence of a transcript of said first gene;
(b) lacking any central contiguous nucleotide sequence of more than 10 nucleotides that is identical to a sequence of a transcript of said second gene and lacking any central contiguous nucleotide sequence of more than 10 nucleotides that is identical to the reverse complement of a sequence of a transcript of said second gene; and
(c) lacking any 3' end contiguous nucleotide sequence of 8 or more nucleotides that is identical to a sequence of said transcript of said second gene and lacking any 3' end contiguous nucleotide sequence of 8 or more nucleotides that is identical to the reverse complement of a sequence of a transcript of said second gene;
said central contiguous nucleotide sequence being in the central region of said siRNA; said 3' end contiguous nucleotide sequence terminating within 3 nucleotides of the 3' end of said siRNA.

28. The computer system of claim 27, wherein said selecting is for an siRNA that is characterized as lacking any central contiguous nucleotide sequence of greater than 8 nucleotides in length that is identical to a sequence of said transcript of said second gene and lacking any central contiguous nucleotide sequence of greater than 8 nucleotides that is identical to the reverse complement of a sequence of a transcript of said second gene.

29. The computer system of claim 27 wherein said central contiguous nucleotide sequence in (a) is 11-15 nucleotides in length.

30. The computer system of claim 29, wherein said central contiguous nucleotide sequence in (a) is 14-15 nucleotides in length.

31. The computer system of claim 29, wherein said central contiguous nucleotide sequence in (a) is 13 nucleotides in length.

32. The computer system of claim 29, wherein said central contiguous nucleotide sequence in (a) is 12 nucleotides in length.

33. The computer system of claim 29, wherein said central contiguous nucleotide sequence in (a) is 11 nucleotides in length.

34. A computer system for designing an siRNA for silencing a first gene but not a second gene in a eukaryotic cell by RNA interference, the computer system comprising:
a central processing unit;
a memory, coupled to the central processing unit, the memory storing one or more programs that cause the central processing unit to perform a method comprising selecting an siRNA sequence that is characterized as:
(a) comprising a 3' end contiguous nucleotide sequence of 8 or more nucleotides that is (i) identical to a sequence of said transcript of said first gene or (ii) identical to the reverse complement of a sequence of a transcript of said first gene;
(b) lacking any central contiguous nucleotide sequence of more than 10 nucleotides that is identical to a sequence of a transcript of said second gene and lacking any central contiguous nucleotide sequence of more than 10 nucleotides that is identical to the reverse complement of a sequence of a transcript of said second gene; and
(c) lacking any 3' end contiguous nucleotide sequence of 8 or more nucleotides that is identical to a sequence of said transcript of said second gene and lacking any 3' end contiguous nucleotide sequence of 8 or more nucleotides that is identical to the reverse complement of a sequence of a transcript of said second gene;
said central contiguous nucleotide sequence being in the central region of said siRNA; said 3' end contiguous nucleotide sequence terminating within 3 nucleotides of the 3' end of said siRNA.

35. The computer system of claim 34, wherein said selecting is of an siRNA that is characterized as lacking any central contiguous nucleotide sequence of greater than 8 nucleotides in length that is identical to a sequence of said transcript of said second gene and lacking any central contiguous nucleotide sequence of greater than 8 nucleotides in length that is identical to the reverse complement of a sequence of a transcript of said second gene.

36. The computer system of claim 34, wherein said 3' end contiguous nucleotide sequence in (a) is 9-15 nucleotides in length.

37. The computer system of claim 36, wherein said 3' end contiguous nucleotide sequence in (a) is 9-12 nucleotides in length.

38. The computer system of claim 37, wherein said 3' end contiguous nucleotide sequence in (a) is 10 nucleotides in length.

39. The computer system of claim 37, wherein said 3' end contiguous nucleotide sequence in (a) is 9 nucleotides in length.

40. A method of designing a small interfering RNA ("siRNA") for silencing a first gene but not a second gene in a eukaryotic cell by RNA interference, comprising:
- (a) selecting an siRNA sequence that is characterized as (i) comprising a central contiguous nucleotide sequence of at least 11 nucleotides that is (1) identical to a sequence of a transcript of said first gene or (2) identical to the reverse complement of a sequence of a transcript of said first gene; (ii) lacking any central contiguous nucleotide sequence of more than 10 nucleotides that is identical to a sequence of a transcript of said second gene and lacking any central contiguous nucleotide sequence of more than 10 nucleotides that is identical to the reverse complement of a sequence of a transcript of said second gene; and (iii) lacking any 3' end contiguous nucleotide sequence of 8 or more nucleotides that is identical to a sequence of said transcript of said second gene and lacking any 3' end contiguous nucleotide sequence of 8 or more nucleotides that is identical to the reverse complement of a sequence of a transcript of said second gene; said central contiguous nucleotide sequence being in the central region of said siRNA; said 3' end contiguous nucleotide sequence terminating within 3 nucleotides of the 3' end of said siRNA; and
- (b) performing an assay to evaluate the siRNA sequence selected according to (a) for efficacy in silencing the target gene.

41. A method of designing a siRNA for silencing a first gene but not a second gene in a eukaryotic cell by RNA interference, comprising:
- (a) selecting an siRNA that is characterized as (i) comprising a 3' end contiguous nucleotide sequence of 8 or more nucleotides that is (1) identical to a sequence of a transcript of said first gene or (2) identical to the reverse complement of a sequence of a transcript of said first gene; (ii) lacking any central contiguous nucleotide sequence of more than 10 nucleotides that is identical to a sequence of a transcript of said second gene and lacking any central contiguous nucleotide sequence of more than 10 nucleotides that is identical to the reverse complement of a sequence of a transcript of said second gene; and (iii) lacking any 3' end contiguous nucleotide sequence of 8 or more nucleotides that is identical to a sequence of said transcript of said second gene and lacking any 3' end contiguous nucleotide sequence of 8 or more nucleotides that is identical to the reverse complement of a sequence of a transcript of said second gene; said central contiguous nucleotide sequence being in the central region of said siRNA; said 3' end contiguous nucleotide sequence terminating within 3 nucleotides of the 3' end of said siRNA; and
- (b) performing an assay to evaluate the siRNA sequence selected according to (a) for efficacy in silencing the target gene.

* * * * *

UNITED STATES PATENT AND TRADEMARK OFFICE
CERTIFICATE OF CORRECTION

PATENT NO.       : 8,609,830 B2                                       Page 1 of 1
APPLICATION NO.  : 10/557219
DATED            : December 17, 2013
INVENTOR(S)      : Jackson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1909 days.

Signed and Sealed this
Twenty-second Day of September, 2015

Michelle K. Lee
*Director of the United States Patent and Trademark Office*

```
                           SEQUENCE LISTING

<160> NUMBER OF SEQ ID NOS: 522

<210> SEQ ID NO 1
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (MAPK14-1)

<400> SEQUENCE: 1
ccuacagaga acugcgguut t                                                   21

<210> SEQ ID NO 2
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (Pos. 4 mismatch with
      MAPK14)

<400> SEQUENCE: 2
ccugcagaga acugcgguut t                                                   21

<210> SEQ ID NO 3
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (Pos. 5 mismatch with
      MAPK14)

<400> SEQUENCE: 3
ccuaaagaga acugcgguut t                                                   21

<210> SEQ ID NO 4
<211> LENGTH: 21
<212> TYPE: DNA
<213> ORGANISM: Artificial Sequence
<220> FEATURE:
```

-continued

<221> NAME/KEY: misc_feature
<222> LOCATION: 1-19
<223> OTHER INFORMATION: siRNA sense strand (Pos.15 mismatch with
      MAPK14)

<400> SEQUENCE: 4
ccuacagaga acugagguut t                                          21

<210> SEQ ID NO 5
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (MAPK14-2)

<400> SEQUENCE: 5
augugauugg ucuguuggat t                                          21

<210> SEQ ID NO 6
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (MAPK14-3)

<400> SEQUENCE: 6
uucuccgagg ucuaaaguat t                                          21

<210> SEQ ID NO 7
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (MAPK14-4)

<400> SEQUENCE: 7
uaauucacag ggaccuaaat t                                          21

<210> SEQ ID NO 8
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (MAPK14-5)

<400> SEQUENCE: 8
ccaguggccg auccuuaugt t                                          21

<210> SEQ ID NO 9
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (MAPK14-6)

<400> SEQUENCE: 9
ugccuacuuu gcucaguact t                                          21

```
<210> SEQ ID NO 10
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (MAPK14-7)

<400> SEQUENCE: 10
gucaucagcu uugugccact t                                              21

<210> SEQ ID NO 11
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (MAPK14-8)

<400> SEQUENCE: 11
ggccuuuuca cgggaacuct t                                              21

<210> SEQ ID NO 12
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-1)

<400> SEQUENCE: 12
gcucacgguc auuaccgagt t                                              21

<210> SEQ ID NO 13
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-2)

<400> SEQUENCE: 13
ccugaggaac auuacucggt t                                              21

<210> SEQ ID NO 14
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-3)

<400> SEQUENCE: 14
ugcugaccuc uguuaccuct t                                              21

<210> SEQ ID NO 15
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-4)

<400> SEQUENCE: 15
```
cgacacggcc uguguagcut t        21

<210> SEQ ID NO 16
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-5)

<400> SEQUENCE: 16
gaugauucag auggccggat t        21

<210> SEQ ID NO 17
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-6)

<400> SEQUENCE: 17
cuugcagcaa cugugggact t        21

<210> SEQ ID NO 18
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-7)

<400> SEQUENCE: 18
ccucacgguc auccgcggct t        21

<210> SEQ ID NO 19
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-8)

<400> SEQUENCE: 19
cuacgcccug gucaucuuct t        21

<210> SEQ ID NO 20
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-9)

<400> SEQUENCE: 20
ucucaaggau auugggcuut t        21

<210> SEQ ID NO 21
<211> LENGTH: 21
<212> TYPE: DNA
<213> ORGANISM: Artificial Sequence
<220> FEATURE:
<221> NAME/KEY: misc_feature

```
<222> LOCATION: 1-19
<223> OTHER INFORMATION: siRNA sense strand (IGFIR-10)

<400> SEQUENCE: 21
ggauauuggg cuuacaact t                                           21

<210> SEQ ID NO 22
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-11)

<400> SEQUENCE: 22
cauuacucgg ggggccauct t                                          21

<210> SEQ ID NO 23
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (IGFIR-12)

<400> SEQUENCE: 23
aaugcugacc ucuguuacct t                                          21

<210> SEQ ID NO 24
<211> LENGTH: 21
<212> TYPE: RNA
<213> ORGANISM: Artificial Sequence
<220> FEATURE:
<223> OTHER INFORMATION: siRNA sense strand (IGFIR-13)

<400> SEQUENCE: 24
cauuaccgag uacuugcugc u                                          21

<210> SEQ ID NO 25
<211> LENGTH: 21
<212> TYPE: RNA
<213> ORGANISM: Artificial Sequence
<220> FEATURE:
<223> OTHER INFORMATION: siRNA sense strand (IGFIR-14)

<400> SEQUENCE: 25
cuugcugcug uuccgagugg c                                          21

<210> SEQ ID NO 26
<211> LENGTH: 21
<212> TYPE: RNA
<213> ORGANISM: Artificial Sequence
<220> FEATURE:
<223> OTHER INFORMATION: siRNA sense strand (IGFIR-15)

<400> SEQUENCE: 26
uccgaguggc uggccucgag a                                          21

<210> SEQ ID NO 27
<211> LENGTH: 21
<212> TYPE: RNA
<213> ORGANISM: Artificial Sequence
<220> FEATURE:
<223> OTHER INFORMATION: siRNA sense strand (IGFIR-16)

<400> SEQUENCE: 27
```

```
ggccucgaga gccucggaga c                                              21

<210> SEQ ID NO 28
<211> LENGTH: 21
<212> TYPE: DNA
<213> ORGANISM: Artificial Sequence
<220> FEATURE:
<221> NAME/KEY: misc_feature
<222> LOCATION: 1-19
<223> OTHER INFORMATION: siRNA sense strand (luc)

<400> SEQUENCE: 28
cguacgcgga auacuucgat t                                              21

<210> SEQ ID NO 29
<211> LENGTH: 19
<212> TYPE: DNA
<213> ORGANISM: Homo sapiens

<400> SEQUENCE: 29
cctacagaga actgcggtt                                                 19

<210> SEQ ID NO 30
<211> LENGTH: 19
<212> TYPE: DNA
<213> ORGANISM: Homo sapiens

<400> SEQUENCE: 30
gctacagaga actgcatct                                                 19

<210> SEQ ID NO 31
<211> LENGTH: 19
<212> TYPE: DNA
<213> ORGANISM: Homo sapiens

<400> SEQUENCE: 31
tctacagaga actgcagcc                                                 19

<210> SEQ ID NO 32
<211> LENGTH: 19
<212> TYPE: DNA
<213> ORGANISM: Homo sapiens

<400> SEQUENCE: 32
tttacagaga acttcggta                                                 19

<210> SEQ ID NO 33
<211> LENGTH: 19
<212> TYPE: DNA
<213> ORGANISM: Homo sapiens

<400> SEQUENCE: 33
cctcaaagaa cctgcggtt                                                 19

<210> SEQ ID NO 34
<211> LENGTH: 19
<212> TYPE: DNA
<213> ORGANISM: Homo sapiens

<400> SEQUENCE: 34
aggcctcaga actgcgggt                                                 19

<210> SEQ ID NO 35
<211> LENGTH: 19
```

```
<212> TYPE: DNA
<213> ORGANISM: Homo sapiens

<400> SEQUENCE: 35
gaagcaggga actttggtg                                                19

<210> SEQ ID NO 36
<211> LENGTH: 19
<212> TYPE: DNA
<213> ORGANISM: Homo sapiens

<400> SEQUENCE: 36
atgagctttg actgcggtt                                                19

<210> SEQ ID NO 37
<211> LENGTH: 19
<212> TYPE: DNA
<213> ORGANISM: Homo sapiens

<400> SEQUENCE: 37
aatatttctt cctgcggtt                                                19

<210> SEQ ID NO 38
<211> LENGTH: 19
<212> TYPE: DNA
<213> ORGANISM: Homo sapiens

<400> SEQUENCE: 38
aggagaaatg actgcggta                                                19

<210> SEQ ID NO 39
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 39
tgttgtccgg ctgatggac                                                19

<210> SEQ ID NO 40
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 40
actcttactg ctctccagt                                                19

<210> SEQ ID NO 41
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 41
cttaacacgg atgctggtg                                                19

<210> SEQ ID NO 42
<211> LENGTH: 19
<212> TYPE: DNA
```

```
<213> ORGANISM: Artificial Sequence
<220> FEATURE:
<223> OTHER INFORMATION: DNA sequence corresponding to siRNA sense
      strand in construction of siRNA library

<400> SEQUENCE: 42
ggagagcttt ctaggacct                                                19

<210> SEQ ID NO 43
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 43
agtcatcccg cagagccgc                                                19

<210> SEQ ID NO 44
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 44
atcgtagtgc ttgtactta                                                19

<210> SEQ ID NO 45
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 45
ggagacgtac cgctgcatc                                                19

<210> SEQ ID NO 46
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 46
gcagtgattg ctcagcagc                                                19

<210> SEQ ID NO 47
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 47
gagtttaccg accaccaag                                                19

<210> SEQ ID NO 48
<211> LENGTH: 19
<212> TYPE: DNA
<213> ORGANISM: Artificial Sequence
<220> FEATURE:
```

```
<223> OTHER INFORMATION: DNA sequence corresponding to siRNA sense
      strand in construction of siRNA library

<400> SEQUENCE: 48
tgcggatgcc attcagtgg                                              19

<210> SEQ ID NO 49
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 49
cacggttggc agagtctat                                              19

<210> SEQ ID NO 50
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 50
gcaagttgag ctctaccgc                                              19

<210> SEQ ID NO 51
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 51
tggccagcgc ttactggaa                                              19

<210> SEQ ID NO 52
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 52
gttcaaaagc tggatgatc                                              19

<210> SEQ ID NO 53
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 53
ggcctctata cccctcaaa                                              19

<210> SEQ ID NO 54
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library
```

<400> SEQUENCE: 54
agaaccgaat cgtctagag                                                    19

<210> SEQ ID NO 55
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 55
cacgatgcat agccatcct                                                    19

<210> SEQ ID NO 56
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 56
cagagacaga atctacact                                                    19

<210> SEQ ID NO 57
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 57
caacagaagg ttgtcttgt                                                    19

<210> SEQ ID NO 58
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 58
ttgtgtgtgg gaccgtaat                                                    19

<210> SEQ ID NO 59
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 59
gctcacggtc attaccgag                                                    19

<210> SEQ ID NO 60
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 60
cctgaggaac attactcgg 19

<210> SEQ ID NO 61
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 61
tgctgacctc tgttacctc 19

<210> SEQ ID NO 62
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 62
cgacacggcc tgtgtagct 19

<210> SEQ ID NO 63
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 63
cggcagccag agcatgtac 19

<210> SEQ ID NO 64
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 64
ccagaacttg cagcaactg 19

<210> SEQ ID NO 65
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 65
cctcacggtc atccgcggc 19

<210> SEQ ID NO 66
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 66
ctacgccctg gtcatcttc 19

<210> SEQ ID NO 67
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 67
tctcaaggat attgggctt                                              19

<210> SEQ ID NO 68
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 68
ggatattggg ctttacaac                                              19

<210> SEQ ID NO 69
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 69
cattactcgg ggggccatc                                              19

<210> SEQ ID NO 70
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 70
aatgctgacc tctgttacc                                              19

<210> SEQ ID NO 71
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 71
ctggatcgta agaaggcag                                              19

<210> SEQ ID NO 72
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 72
tggaaggtga aaggtcacc                                              19

<210> SEQ ID NO 73
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 73
ggacaactgc agctactct                                                  19

<210> SEQ ID NO 74
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 74
tacggactca ccttgcttg                                                  19

<210> SEQ ID NO 75
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 75
gtatatacat tcagctgac                                                  19

<210> SEQ ID NO 76
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 76
ggaacacccc ccgcttatc                                                  19

<210> SEQ ID NO 77
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 77
gtggccgatc cttatgatc                                                  19

<210> SEQ ID NO 78
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 78
atgtgattgg tctgttgga                                                  19

<210> SEQ ID NO 79
<211> LENGTH: 19

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 79
gtcatcagct ttgtgccac                                                19

<210> SEQ ID NO 80
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 80
taattcacag ggacctaaa                                                19

<210> SEQ ID NO 81
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 81
tgcctacttt gctcagtac                                                19

<210> SEQ ID NO 82
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 82
cctacagaga actgcggtt                                                19

<210> SEQ ID NO 83
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 83
ttctccgagg tctaaagta                                                19

<210> SEQ ID NO 84
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 84
ccagtggccg atccttatg                                                19

<210> SEQ ID NO 85
<211> LENGTH: 19
<212> TYPE: DNA
<213> ORGANISM: Artificial Sequence
```

-continued

```
<220> FEATURE:
<223> OTHER INFORMATION: DNA sequence corresponding to siRNA sense
      strand in construction of siRNA library

<400> SEQUENCE: 85
ggccttttca cgggaactc                                                19

<210> SEQ ID NO 86
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 86
ctgaagaagc tactgcttg                                                19

<210> SEQ ID NO 87
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 87
gacatgcgaa tgacactag                                                19

<210> SEQ ID NO 88
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 88
agaggaactc tctgcaagc                                                19

<210> SEQ ID NO 89
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 89
aaactgggag gctacttac                                                19

<210> SEQ ID NO 90
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 90
actgacaaca aagtgcagc                                                19

<210> SEQ ID NO 91
<211> LENGTH: 19
<212> TYPE: DNA
<213> ORGANISM: Artificial Sequence
<220> FEATURE:
<223> OTHER INFORMATION: DNA sequence corresponding to siRNA sense
``` strand in construction of siRNA library

<400> SEQUENCE: 91
ctcacattgt ccaccagga                                    19

<210> SEQ ID NO 92
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 92
gacctgtgcc ttttagaga                                    19

<210> SEQ ID NO 93
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 93
gacttcattg acagtggcc                                    19

<210> SEQ ID NO 94
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 94
aaaggacaac tgcagctac                                    19

<210> SEQ ID NO 95
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 95
tggaggggaa tgctcagaa                                    19

<210> SEQ ID NO 96
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 96
taaagatggc actttcccg                                    19

<210> SEQ ID NO 97
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 97
aaggcagcta aaggaagtg					19

<210> SEQ ID NO 98
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 98
tattgggcca gcagattac					19

<210> SEQ ID NO 99
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 99
ttatgacgct aggccacaa					19

<210> SEQ ID NO 100
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 100
ggagaaagat ccctttgag					19

<210> SEQ ID NO 101
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 101
acaaaaacgg agatccgtc					19

<210> SEQ ID NO 102
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 102
ataagcagca agaaacggc					19

<210> SEQ ID NO 103
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 103 gaatttcgggctactttgg 19

<210> SEQ ID NO 104
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 104
cgcaccttcc atgtggaga 19

<210> SEQ ID NO 105
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 105
agacgttttt gtgctgtgg 19

<210> SEQ ID NO 106
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 106
gctggagaac ctcatgctg 19

<210> SEQ ID NO 107
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 107
ctctaccact gaagagttg 19

<210> SEQ ID NO 108
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 108
aagtgggtcg taagaacca 19

<210> SEQ ID NO 109
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 109
gaagctgtcc ctgctaaat 19

```
<210> SEQ ID NO 110
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 110
gaagagatcc cagtgcttc                                              19

<210> SEQ ID NO 111
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 111
tctgaaagtg accagctca                                              19

<210> SEQ ID NO 112
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 112
gaaaatgaag ctttgcggg                                              19

<210> SEQ ID NO 113
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 113
aagaagaacc agtggttcg                                              19

<210> SEQ ID NO 114
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 114
ccgagttatt catcgagac                                              19

<210> SEQ ID NO 115
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 115
aagagaccta cctccggat                                              19

<210> SEQ ID NO 116
```

```
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 116
aatatcctca ggggtggag                                                    19

<210> SEQ ID NO 117
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 117
gtgcctcttg ttgcagaga                                                    19

<210> SEQ ID NO 118
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 118
gaagctctcc agaccattt                                                    19

<210> SEQ ID NO 119
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 119
agaagctgtg gatcttagg                                                    19

<210> SEQ ID NO 120
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 120
tgatgcacat catggtggc                                                    19

<210> SEQ ID NO 121
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 121
ctaggaaacc tcaggctta                                                    19

<210> SEQ ID NO 122
<211> LENGTH: 19
<212> TYPE: DNA
```

```
<213> ORGANISM: Artificial Sequence
<220> FEATURE:
<223> OTHER INFORMATION: DNA sequence corresponding to siRNA sense
      strand in construction of siRNA library

<400> SEQUENCE: 122
gcgaatctct gcctttcga                                                  19

<210> SEQ ID NO 123
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 123
cagtcaagct ggctgactt                                                  19

<210> SEQ ID NO 124
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 124
ggatctgatg cgccagttt                                                  19

<210> SEQ ID NO 125
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 125
gcacaactcc tgcaaattc                                                  19

<210> SEQ ID NO 126
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 126
gatggaagag cctctaaga                                                  19

<210> SEQ ID NO 127
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 127
acgaaaagct gcttgagag                                                  19

<210> SEQ ID NO 128
<211> LENGTH: 19
<212> TYPE: DNA
<213> ORGANISM: Artificial Sequence
<220> FEATURE:
```

<223> OTHER INFORMATION: DNA sequence corresponding to siRNA sense
      strand in construction of siRNA library

<400> SEQUENCE: 128
gaagaccatc tgtggcacc                                            19

<210> SEQ ID NO 129
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 129
tcagggacca gctttactg                                            19

<210> SEQ ID NO 130
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 130
gttaccaaga gcctctttg                                            19

<210> SEQ ID NO 131
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 131
aaccaaagtg aactggctg                                            19

<210> SEQ ID NO 132
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 132
gatcggccac ttccttttc                                            19

<210> SEQ ID NO 133
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 133
agagatctgg gcctcatgt                                            19

<210> SEQ ID NO 134
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 134
agttcgatca gcagctgtt                                                    19

<210> SEQ ID NO 135
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 135
tagattgttc caggacacg                                                    19

<210> SEQ ID NO 136
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 136
gaagttggat gccagctgt                                                    19

<210> SEQ ID NO 137
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 137
tggtgatcac tccaggtag                                                    19

<210> SEQ ID NO 138
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 138
tgtccctttc agagacagc                                                    19

<210> SEQ ID NO 139
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 139
gacgtcaaac gtaaacagc                                                    19

<210> SEQ ID NO 140
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 140
aagttcatgt cagggctgg                    19

<210> SEQ ID NO 141
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 141
caaagatgcc cttctgaac                    19

<210> SEQ ID NO 142
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 142
aatgcgcaaa ttcagcgag                    19

<210> SEQ ID NO 143
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 143
gcacaaaagc ttgtctcca                    19

<210> SEQ ID NO 144
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 144
ttgcagattt tgggtggtc                    19

<210> SEQ ID NO 145
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 145
acagtcttag gaatcgtgc                    19

<210> SEQ ID NO 146
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 146
aggacttcgc ccataagag                    19

```
<210> SEQ ID NO 147
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 147
caacctccag gatacactc                                              19

<210> SEQ ID NO 148
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 148
ccaactttct agctgctgt                                              19

<210> SEQ ID NO 149
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 149
gaatgtgagc gtagagtgg                                              19

<210> SEQ ID NO 150
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 150
ccattggtta ctgacgtgg                                              19

<210> SEQ ID NO 151
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 151
aacccaaacc tccacaatc                                              19

<210> SEQ ID NO 152
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 152
gaaagaagca gttgacctc                                              19
```

<210> SEQ ID NO 153
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 153
ctaaaagctg ggtggactc                                                19

<210> SEQ ID NO 154
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 154
gaaagcacct ctttgtgtg                                                19

<210> SEQ ID NO 155
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 155
tgaggccttg gaactcaag                                                19

<210> SEQ ID NO 156
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 156
cctcttggtc gaccttagt                                                19

<210> SEQ ID NO 157
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 157
gcacccagga cttccattt                                                19

<210> SEQ ID NO 158
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 158
gaaactgcag ctatcttcc                                                19

<210> SEQ ID NO 159
<211> LENGTH: 19

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 159
gttacaatga ggctgatgc                                                   19

<210> SEQ ID NO 160
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 160
tcacgactcg ctgaactgt                                                   19

<210> SEQ ID NO 161
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 161
gaccgaccct gaagcagaa                                                   19

<210> SEQ ID NO 162
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 162
ttccaggagt atgctgttt                                                   19

<210> SEQ ID NO 163
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 163
ggaacttctg cacaaggag                                                   19

<210> SEQ ID NO 164
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 164
tgttgacgga cagcctatt                                                   19

<210> SEQ ID NO 165
<211> LENGTH: 19
<212> TYPE: DNA
<213> ORGANISM: Artificial Sequence
```

```
<220> FEATURE:
<223> OTHER INFORMATION: DNA sequence corresponding to siRNA sense
      strand in construction of siRNA library

<400> SEQUENCE: 165
ggcattggca tctgctttt                                                19

<210> SEQ ID NO 166
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 166
gtgaatgaga cactccagt                                                19

<210> SEQ ID NO 167
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 167
gagctggtgt ctgattgtt                                                19

<210> SEQ ID NO 168
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 168
gtgtaagcag ctgaggtct                                                19

<210> SEQ ID NO 169
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 169
ctgcccaaag aaattcgga                                                19

<210> SEQ ID NO 170
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 170
atttgcccgc gcatttgtg                                                19

<210> SEQ ID NO 171
<211> LENGTH: 19
<212> TYPE: DNA
<213> ORGANISM: Artificial Sequence
<220> FEATURE:
<223> OTHER INFORMATION: DNA sequence corresponding to siRNA sense
``` strand in construction of siRNA library

<400> SEQUENCE: 171
agaagatgaa tggtctggc 19

<210> SEQ ID NO 172
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 172
aacgggcgat tatctctgg 19

<210> SEQ ID NO 173
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 173
gacttagagc tgggaatct 19

<210> SEQ ID NO 174
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 174
agttgaggag gtttctgca 19

<210> SEQ ID NO 175
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 175
ggattatatc cagcagctc 19

<210> SEQ ID NO 176
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 176
gtggctggat tcatgttcc 19

<210> SEQ ID NO 177
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

```
<400> SEQUENCE: 177
caaggcatcc gttatatct                                                   19

<210> SEQ ID NO 178
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 178
accaggattt ggagtggat                                                   19

<210> SEQ ID NO 179
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 179
ctgaagaagc agtcgcagt                                                   19

<210> SEQ ID NO 180
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 180
atcgattctg ctcctctag                                                   19

<210> SEQ ID NO 181
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 181
tgcctgaaag agacttgtg                                                   19

<210> SEQ ID NO 182
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 182
tcttggacgt gattggact                                                   19

<210> SEQ ID NO 183
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 183
```
agaaaacctg gattcccac         19

<210> SEQ ID NO 184
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 184
accacagaac attctggtg         19

<210> SEQ ID NO 185
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 185
gaaagccaga caacttctg         19

<210> SEQ ID NO 186
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 186
ctctcagtga aagtgccaa         19

<210> SEQ ID NO 187
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 187
gacactgcct gcttttact         19

<210> SEQ ID NO 188
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 188
aagaacctgg tgaaagtcc         19

<210> SEQ ID NO 189
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 189
gaagtgcagc aggttaaga         19

```
<210> SEQ ID NO 190
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 190
agccgagttg taactatcc                                                19

<210> SEQ ID NO 191
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 191
gatcacagtg gcaatggaa                                                19

<210> SEQ ID NO 192
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 192
aaactcttgg aagtggtgc                                                19

<210> SEQ ID NO 193
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 193
atgaatccac agctctacc                                                19

<210> SEQ ID NO 194
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 194
gaatggaagc ctgaactga                                                19

<210> SEQ ID NO 195
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 195
agacatcatg gagtccagc                                                19

<210> SEQ ID NO 196
```

<210> SEQ ID NO 196
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 196
caagttctcc atcaagtcc                                                  19

<210> SEQ ID NO 197
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 197
ggaatagtat gcgcagctt                                                  19

<210> SEQ ID NO 198
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 198
gtgattcaga tggagctag                                                  19

<210> SEQ ID NO 199
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 199
cacccgtaca tcaatgtct                                                  19

<210> SEQ ID NO 200
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 200
tcattggaag aacagcggc                                                  19

<210> SEQ ID NO 201
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 201
aagaagacgt tcagcgaca                                                  19

<210> SEQ ID NO 202
<211> LENGTH: 19
<212> TYPE: DNA

```
<213> ORGANISM: Artificial Sequence
<220> FEATURE:
<223> OTHER INFORMATION: DNA sequence corresponding to siRNA sense
      strand in construction of siRNA library

<400> SEQUENCE: 202
aaaaagcctg cccttggtt                                                  19

<210> SEQ ID NO 203
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 203
cttgcaacgt ctgttagag                                                  19

<210> SEQ ID NO 204
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 204
ctgaaggctt ccttacaag                                                  19

<210> SEQ ID NO 205
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 205
cagaagttgt ggaatgagg                                                  19

<210> SEQ ID NO 206
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 206
gcaatgagga cagcttgtg                                                  19

<210> SEQ ID NO 207
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 207
tgtagctttc cactggagt                                                  19

<210> SEQ ID NO 208
<211> LENGTH: 19
<212> TYPE: DNA
<213> ORGANISM: Artificial Sequence
<220> FEATURE:
```

<223> OTHER INFORMATION: DNA sequence corresponding to siRNA sense
      strand in construction of siRNA library

<400> SEQUENCE: 208
tctccttgtg aacagcaac                                              19

<210> SEQ ID NO 209
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 209
agtgaagaac ctggggtac                                              19

<210> SEQ ID NO 210
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 210
gttccaccag cattgttcc                                              19

<210> SEQ ID NO 211
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 211
gaatgagatg caggtgctc                                              19

<210> SEQ ID NO 212
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 212
caattcgtcg gaggcatca                                              19

<210> SEQ ID NO 213
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 213
ggggagtttg ctggacttt                                              19

<210> SEQ ID NO 214
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

```
<400> SEQUENCE: 214
gcagtgcctg cctatgaaa                                                19

<210> SEQ ID NO 215
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 215
ctagacctag acctagact                                                19

<210> SEQ ID NO 216
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 216
gaggatgtca acggttatg                                                19

<210> SEQ ID NO 217
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 217
caaagtcttg gccagaatc                                                19

<210> SEQ ID NO 218
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 218
gatcgagctg gctgtctttt                                               19

<210> SEQ ID NO 219
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 219
ggtcttaaag aaggacgtc                                                19

<210> SEQ ID NO 220
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 220
```
tgaggacgac ctatttgag						19

<210> SEQ ID NO 221
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 221
tgagctggtg gattatcac						19

<210> SEQ ID NO 222
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 222
ctggtacaag gcagagctt						19

<210> SEQ ID NO 223
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 223
ccggaacgtc taagagtca						19

<210> SEQ ID NO 224
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 224
tacagaaaag tttggccgg						19

<210> SEQ ID NO 225
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 225
aatgaagcct ttgtggctg						19

<210> SEQ ID NO 226
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 226
gtgcacattc ctgctgtct						19

```
<210> SEQ ID NO 227
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 227
cctccctatt cagaaagct                                               19

<210> SEQ ID NO 228
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 228
gactttgaaa ttggtcgcc                                               19

<210> SEQ ID NO 229
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 229
cacccaaaag agcaagcag                                               19

<210> SEQ ID NO 230
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 230
taagcctggt ggtgatctt                                               19

<210> SEQ ID NO 231
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 231
aaggtcttta cgccagtac                                               19

<210> SEQ ID NO 232
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 232
ggaatgtatc cgagcactg                                               19
```

<210> SEQ ID NO 233
<211> LENGTH: 19
<212> TYPE: DNA
<213> ORGANISM: Artificial Sequence
<220> FEATURE:
<223> OTHER INFORMATION: DNA sequence corresponding to siRNA sense
strand in construction of siRNA library

<400> SEQUENCE: 233
ggactctgaa gatgtacct                                                19

<210> SEQ ID NO 234
<211> LENGTH: 19
<212> TYPE: DNA
<213> ORGANISM: Artificial Sequence
<220> FEATURE:
<223> OTHER INFORMATION: DNA sequence corresponding to siRNA sense
strand in construction of siRNA library

<400> SEQUENCE: 234
ggcatactag tacaagtgg                                                19

<210> SEQ ID NO 235
<211> LENGTH: 19
<212> TYPE: DNA
<213> ORGANISM: Artificial Sequence
<220> FEATURE:
<223> OTHER INFORMATION: DNA sequence corresponding to siRNA sense
strand in construction of siRNA library

<400> SEQUENCE: 235
gaaaagactc ctggctgtg                                                19

<210> SEQ ID NO 236
<211> LENGTH: 19
<212> TYPE: DNA
<213> ORGANISM: Artificial Sequence
<220> FEATURE:
<223> OTHER INFORMATION: DNA sequence corresponding to siRNA sense
strand in construction of siRNA library

<400> SEQUENCE: 236
ctttgaatgc cagggaac                                                 19

<210> SEQ ID NO 237
<211> LENGTH: 19
<212> TYPE: DNA
<213> ORGANISM: Artificial Sequence
<220> FEATURE:
<223> OTHER INFORMATION: DNA sequence corresponding to siRNA sense
strand in construction of siRNA library

<400> SEQUENCE: 237
ccaaggaacc tgctttgat                                                19

<210> SEQ ID NO 238
<211> LENGTH: 19
<212> TYPE: DNA
<213> ORGANISM: Artificial Sequence
<220> FEATURE:
<223> OTHER INFORMATION: DNA sequence corresponding to siRNA sense
strand in construction of siRNA library

<400> SEQUENCE: 238
gactcagacc actgcttca                                                19

<210> SEQ ID NO 239
<211> LENGTH: 19

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 239
gctgctgttg gaccacttt                                              19

<210> SEQ ID NO 240
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 240
tgccaactga agaggatga                                              19

<210> SEQ ID NO 241
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 241
tgatcactgc ttccccgat                                              19

<210> SEQ ID NO 242
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 242
atatcgacga ttgtccagg                                              19

<210> SEQ ID NO 243
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 243
aggcaagccc tgcaagaat                                              19

<210> SEQ ID NO 244
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 244
cacttacacc tgtgtgtgc                                              19

<210> SEQ ID NO 245
<211> LENGTH: 19
<212> TYPE: DNA
<213> ORGANISM: Artificial Sequence
```

```
-continued

<220> FEATURE:
<223> OTHER INFORMATION: DNA sequence corresponding to siRNA sense
      strand in construction of siRNA library

<400> SEQUENCE: 245
tatcagaccg gacctctat                                              19

<210> SEQ ID NO 246
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 246
attgaccacc aggtttctg                                              19

<210> SEQ ID NO 247
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 247
cttacaaaag ggagcacac                                              19

<210> SEQ ID NO 248
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 248
gtctcagctt ctgcggtat                                              19

<210> SEQ ID NO 249
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 249
aggattttgt ggcctccat                                              19

<210> SEQ ID NO 250
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 250
tccaggttga aggcattca                                              19

<210> SEQ ID NO 251
<211> LENGTH: 19
<212> TYPE: DNA
<213> ORGANISM: Artificial Sequence
<220> FEATURE:
<223> OTHER INFORMATION: DNA sequence corresponding to siRNA sense
``` strand in construction of siRNA library

<400> SEQUENCE: 251
ttggcaaagg ctccttgta        19

<210> SEQ ID NO 252
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 252
ccatctgctt gagctactt        19

<210> SEQ ID NO 253
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 253
gttgacttac ctgacggac        19

<210> SEQ ID NO 254
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 254
gacatcccga gtctataag        19

<210> SEQ ID NO 255
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 255
tggaggagaa ttaggcctt        19

<210> SEQ ID NO 256
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 256
gcacaaggag gtcttcttc        19

<210> SEQ ID NO 257
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

```
<400> SEQUENCE: 257
cagatcactc caggcatag                                              19

<210> SEQ ID NO 258
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 258
atgtgtggtg actgctttg                                              19

<210> SEQ ID NO 259
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 259
tgacatcatt gtgctggcc                                              19

<210> SEQ ID NO 260
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 260
cgttccgatc ctctatact                                              19

<210> SEQ ID NO 261
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 261
tgaccaaaga tgacctgtg                                              19

<210> SEQ ID NO 262
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 262
gagaaagaat ggggtcggt                                              19

<210> SEQ ID NO 263
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 263
```
cgacatccag aagttgtca                                                19

<210> SEQ ID NO 264
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 264
tgaggagcag attgccact                                                19

<210> SEQ ID NO 265
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 265
gaggtacaat tgcgaatat                                                19

<210> SEQ ID NO 266
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 266
tactacgtcg gacagagtt                                                19

<210> SEQ ID NO 267
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 267
aactacaata acgccactg                                                19

<210> SEQ ID NO 268
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 268
gccacagtcg tcttgctgt                                                19

<210> SEQ ID NO 269
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 269
gggcggcttt gccaagtgc                                                19

```
<210> SEQ ID NO 270
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 270
cacgcctcat cctctacaa                                                  19

<210> SEQ ID NO 271
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 271
gagacctacc tccggatca                                                  19

<210> SEQ ID NO 272
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 272
cccaccacag ctagaactt                                                  19

<210> SEQ ID NO 273
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 273
ctattcccag tcagaggcg                                                  19

<210> SEQ ID NO 274
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 274
cagtagagga gccgtcaaa                                                  19

<210> SEQ ID NO 275
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 275
cagttcacta ttacgcaga                                                  19

<210> SEQ ID NO 276
```

```
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 276
tgttacgaga tgacagatt                                                       19

<210> SEQ ID NO 277
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 277
aacccagagg atcgtccca                                                       19

<210> SEQ ID NO 278
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 278
ctgtttggag aaaaccctc                                                       19

<210> SEQ ID NO 279
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 279
gacaacccaa accagagtc                                                       19

<210> SEQ ID NO 280
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 280
gtcttgactg ggatgaaaa                                                       19

<210> SEQ ID NO 281
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 281
accagagtct tttgacagg                                                       19

<210> SEQ ID NO 282
<211> LENGTH: 19
<212> TYPE: DNA
```

```
<213> ORGANISM: Artificial Sequence
<220> FEATURE:
<223> OTHER INFORMATION: DNA sequence corresponding to siRNA sense
      strand in construction of siRNA library

<400> SEQUENCE: 282
tagaccaccc attgcttcc                                                   19

<210> SEQ ID NO 283
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 283
agagccttcg aaggcttca                                                   19

<210> SEQ ID NO 284
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 284
gaccatagca tccgccatg                                                   19

<210> SEQ ID NO 285
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 285
tagctctgct agaggagga                                                   19

<210> SEQ ID NO 286
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 286
acagaacggc tgaatagcc                                                   19

<210> SEQ ID NO 287
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 287
gagaatgaga gcctgactg                                                   19

<210> SEQ ID NO 288
<211> LENGTH: 19
<212> TYPE: DNA
<213> ORGANISM: Artificial Sequence
<220> FEATURE:
```

<223> OTHER INFORMATION: DNA sequence corresponding to siRNA sense
      strand in construction of siRNA library

<400> SEQUENCE: 288
ggaaacagag tgcctctct                                                       19

<210> SEQ ID NO 289
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 289
ccactcagct cagatcatg                                                       19

<210> SEQ ID NO 290
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 290
tctggtctct tgcaaaagg                                                       19

<210> SEQ ID NO 291
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 291
atttttgcgg cgccagaat                                                       19

<210> SEQ ID NO 292
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 292
gaaaaacgga ggtcgcgtt                                                       19

<210> SEQ ID NO 293
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 293
gaaaacaaat gccccgtgc                                                       19

<210> SEQ ID NO 294
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 294
tggcactcat cactgtcat        19

<210> SEQ ID NO 295
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 295
tgagaacagt gaccagcag        19

<210> SEQ ID NO 296
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 296
gggcccagga ctgttgatg        19

<210> SEQ ID NO 297
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 297
agagatgggc attgtttcc        19

<210> SEQ ID NO 298
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 298
gctcatggag atgtttggt        19

<210> SEQ ID NO 299
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 299
agcattgctg tttcacgcc        19

<210> SEQ ID NO 300
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 300
ttgagctgct gcaacggtc                                            19

<210> SEQ ID NO 301
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 301
gtccccacat tccaagtca                                            19

<210> SEQ ID NO 302
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 302
cctctctgga atttgtgcc                                            19

<210> SEQ ID NO 303
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 303
caagtacttc tccaacatt                                            19

<210> SEQ ID NO 304
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 304
tggaggaaca tgtgtgtcc                                            19

<210> SEQ ID NO 305
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 305
ttactgcagg aacccagac                                            19

<210> SEQ ID NO 306
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 306
tggctttgaa tctttggcc                                            19

<210> SEQ ID NO 307
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 307
aggtgcactg cagttcaac                                                    19

<210> SEQ ID NO 308
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 308
ttcagctagt acaggtcct                                                    19

<210> SEQ ID NO 309
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 309
ttgattcctc gcgacatct                                                    19

<210> SEQ ID NO 310
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 310
gcttttccca tgatctcca                                                    19

<210> SEQ ID NO 311
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 311
cttggcatgg aacattgtg                                                    19

<210> SEQ ID NO 312
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 312
gcctcagaaa gggattgct                                                    19

```
<210> SEQ ID NO 313
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 313
gctctggatg tgcacacat                                                19

<210> SEQ ID NO 314
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 314
gtgtctcaaa ggagctttc                                                19

<210> SEQ ID NO 315
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 315
attcaacggg ctcttgtgc                                                19

<210> SEQ ID NO 316
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 316
gatcgatggc tacgagtgt                                                19

<210> SEQ ID NO 317
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 317
catcccctac aagatcgag                                                19

<210> SEQ ID NO 318
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 318
gcaactttgg tctcctttc                                                19

<210> SEQ ID NO 319
<211> LENGTH: 19
```

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 319
gcaattggct gtgatgctc                                                    19

<210> SEQ ID NO 320
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 320
gagacaagtt aactcgtgc                                                    19

<210> SEQ ID NO 321
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 321
tcctggcaag aaagcttga                                                    19

<210> SEQ ID NO 322
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 322
aaacctctac acgttctgc                                                    19

<210> SEQ ID NO 323
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 323
ctaaaggtga aaagctccg                                                    19

<210> SEQ ID NO 324
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 324
gatctggaag accacccaa                                                    19

<210> SEQ ID NO 325
<211> LENGTH: 19
<212> TYPE: DNA
<213> ORGANISM: Artificial Sequence
```

```
<220> FEATURE:
<223> OTHER INFORMATION: DNA sequence corresponding to siRNA sense
      strand in construction of siRNA library

<400> SEQUENCE: 325
cagaacccaa aagggtaag                                                    19

<210> SEQ ID NO 326
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 326
aggaaatagg cagggtgtg                                                    19

<210> SEQ ID NO 327
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 327
agcagtgctg atgataagg                                                    19

<210> SEQ ID NO 328
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 328
aagccattgg tgaagagag                                                    19

<210> SEQ ID NO 329
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 329
tgtgtcattg ctctccaag                                                    19

<210> SEQ ID NO 330
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 330
gcagatgagc aaggatgct                                                    19

<210> SEQ ID NO 331
<211> LENGTH: 19
<212> TYPE: DNA
<213> ORGANISM: Artificial Sequence
<220> FEATURE:
<223> OTHER INFORMATION: DNA sequence corresponding to siRNA sense
``` strand in construction of siRNA library

<400> SEQUENCE: 331
gtacatccat gtggccaaa                                                  19

<210> SEQ ID NO 332
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 332
tgggtcatga aagctgcca                                                  19

<210> SEQ ID NO 333
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 333
gaacaccgtt aacacctcc                                                  19

<210> SEQ ID NO 334
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 334
ataacaggag agatccagc                                                  19

<210> SEQ ID NO 335
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 335
tggtgtcctt gaggttgtc                                                  19

<210> SEQ ID NO 336
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 336
acctgtctct tggatattc                                                  19

<210> SEQ ID NO 337
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library -continued

```
<400> SEQUENCE: 337
taaatgtgat ttgccttct                                                    19

<210> SEQ ID NO 338
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 338
gaagttatgg aattccttt                                                    19

<210> SEQ ID NO 339
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 339
caccatgtcc tgaattcat                                                    19

<210> SEQ ID NO 340
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 340
tcaagcacct tcattctgc                                                    19

<210> SEQ ID NO 341
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 341
cgagttttat gatgacgcc                                                    19

<210> SEQ ID NO 342
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 342
atacgtccag gccctcttt                                                    19

<210> SEQ ID NO 343
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 343
```
tgcagcactt caaggtgct 19

<210> SEQ ID NO 344
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 344
cgggcagacc ggcatgttt 19

<210> SEQ ID NO 345
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 345
gacatgagaa cctggctca 19

<210> SEQ ID NO 346
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 346
cttgcaggcc ttgtttgtg 19

<210> SEQ ID NO 347
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 347
taatacagct ggggacgac 19

<210> SEQ ID NO 348
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 348
agaacctcgg ctacaacgt 19

<210> SEQ ID NO 349
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 349
tcggctacaa cgtgaccaa 19

```
<210> SEQ ID NO 350
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 350
tccgcatctc catgtgcca                                                   19

<210> SEQ ID NO 351
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 351
tcacaaagtg tgctgggtt                                                   19

<210> SEQ ID NO 352
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 352
ccaggaggaa ttcaaaggt                                                   19

<210> SEQ ID NO 353
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 353
gctcaccatc tgaggaaga                                                   19

<210> SEQ ID NO 354
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 354
tgacagtgga gcctgtgta                                                   19

<210> SEQ ID NO 355
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 355
ctttctgaat ggggagcct                                                   19

<210> SEQ ID NO 356
```

<211> LENGTH: 19
    <212> TYPE: DNA
    <213> ORGANISM: Artificial Sequence
    <220> FEATURE:
    <223> OTHER INFORMATION: DNA sequence corresponding to siRNA sense
          strand in construction of siRNA library

<400> SEQUENCE: 356
tacacacacc agagtgatg                                                        19

<210> SEQ ID NO 357
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 357
atgaaggaga gtgatcacc                                                        19

<210> SEQ ID NO 358
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 358
aatggcagtg aaacaccct                                                        19

<210> SEQ ID NO 359
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 359
aagtttgtgt cccagacac                                                        19

<210> SEQ ID NO 360
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 360
aatggcttcc gctgcctct                                                        19

<210> SEQ ID NO 361
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 361
gaacatggcc aagggtgag                                                        19

<210> SEQ ID NO 362
<211> LENGTH: 19
<212> TYPE: DNA

```
<213> ORGANISM: Artificial Sequence
<220> FEATURE:
<223> OTHER INFORMATION: DNA sequence corresponding to siRNA sense
      strand in construction of siRNA library

<400> SEQUENCE: 362
gagtctggga cctccttct                                                     19

<210> SEQ ID NO 363
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 363
ccagggagac tccggcccc                                                     19

<210> SEQ ID NO 364
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 364
gggaccgtca tggcgtcgc                                                     19

<210> SEQ ID NO 365
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 365
atttaatttg gcagagcgg                                                     19

<210> SEQ ID NO 366
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 366
gctcaaggaa aacatacac                                                     19

<210> SEQ ID NO 367
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 367
tactaaacag attgatgtt                                                     19

<210> SEQ ID NO 368
<211> LENGTH: 19
<212> TYPE: DNA
<213> ORGANISM: Artificial Sequence
<220> FEATURE:
```

```
<223> OTHER INFORMATION: DNA sequence corresponding to siRNA sense
      strand in construction of siRNA library

<400> SEQUENCE: 368
tactgataat ggtactgaa                                                19

<210> SEQ ID NO 369
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 369
aggagtgata attaaaggt                                                19

<210> SEQ ID NO 370
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 370
gttttctctg ttacaatac                                                19

<210> SEQ ID NO 371
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 371
tggaaatata aatcaatcc                                                19

<210> SEQ ID NO 372
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 372
actaactaga atcctccag                                                19

<210> SEQ ID NO 373
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 373
aaactctgag tacattgga                                                19

<210> SEQ ID NO 374
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library
```

```
<400> SEQUENCE: 374
taactgttca agaagagca                                            19

<210> SEQ ID NO 375
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 375
aagaagaata tatcacatc                                            19

<210> SEQ ID NO 376
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 376
agttgaccaa cacaatgca                                            19

<210> SEQ ID NO 377
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 377
tacatgaact acaagaaaa                                            19

<210> SEQ ID NO 378
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 378
gactaagctt aattgcttt                                            19

<210> SEQ ID NO 379
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 379
ggggcagtat actgaagaa                                            19

<210> SEQ ID NO 380
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 380
```
ttcttgtata ttattaagt                                            19

<210> SEQ ID NO 381
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 381
tctataattt atattcttt                                            19

<210> SEQ ID NO 382
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 382
tacaaagaat aaattttct                                            19

<210> SEQ ID NO 383
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 383
cagcgcagct tcgggagca                                            19

<210> SEQ ID NO 384
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 384
cggagttgca gctcccgga                                            19

<210> SEQ ID NO 385
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 385
ggcaagattg tgcctaagt                                            19

<210> SEQ ID NO 386
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 386
gggagaagat gtccatgga                                            19

```
<210> SEQ ID NO 387
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 387
gacttcgtgt tcgtggtgt                                               19

<210> SEQ ID NO 388
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 388
gcccgatact acctacggc                                               19

<210> SEQ ID NO 389
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 389
ggactggcaa ccaaagtcg                                               19

<210> SEQ ID NO 390
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 390
tgtatcatgt ataccttgt                                               19

<210> SEQ ID NO 391
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 391
ttcttgccta aaagagacc                                               19

<210> SEQ ID NO 392
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 392
tccagaagat gcttcagac                                               19
```

<210> SEQ ID NO 393
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 393
acgagctgct taatgacga                                               19

<210> SEQ ID NO 394
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 394
tcgattgctc ccagcagcc                                               19

<210> SEQ ID NO 395
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 395
cacagtcctc aataaaggc                                               19

<210> SEQ ID NO 396
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 396
caatgcctcc aagccctcg                                               19

<210> SEQ ID NO 397
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 397
agtgggtgga ctattcgga                                               19

<210> SEQ ID NO 398
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 398
tacatgagcg agcacttgc                                               19

<210> SEQ ID NO 399
<211> LENGTH: 19

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 399
ctcaaggcct cctaatagc                                              19

<210> SEQ ID NO 400
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 400
ccgcggtgcc atgtctgca                                              19

<210> SEQ ID NO 401
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 401
cccctccccc tcaacccca                                              19

<210> SEQ ID NO 402
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 402
attttctaga aaacggtaa                                              19

<210> SEQ ID NO 403
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 403
gaggggcgaa gtttcggca                                              19

<210> SEQ ID NO 404
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 404
ctgggaccgg gaagccgga                                              19

<210> SEQ ID NO 405
<211> LENGTH: 19
<212> TYPE: DNA
<213> ORGANISM: Artificial Sequence
```

```
<220> FEATURE:
<223> OTHER INFORMATION: DNA sequence corresponding to siRNA sense
      strand in construction of siRNA library

<400> SEQUENCE: 405
cttctacttc tgttggcag                                              19

<210> SEQ ID NO 406
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 406
acttactatt cagactgca                                              19

<210> SEQ ID NO 407
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 407
gccctcaccc acagtagcc                                              19

<210> SEQ ID NO 408
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 408
cagaggaatg cacacccag                                              19

<210> SEQ ID NO 409
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 409
gattgattag atctcttga                                              19

<210> SEQ ID NO 410
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 410
gtgagtatta tcccagttg                                              19

<210> SEQ ID NO 411
<211> LENGTH: 19
<212> TYPE: DNA
<213> ORGANISM: Artificial Sequence
<220> FEATURE:
<223> OTHER INFORMATION: DNA sequence corresponding to siRNA sense
```

-continued strand in construction of siRNA library

<400> SEQUENCE: 411
atctggggtg ctgattgct                                               19

<210> SEQ ID NO 412
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 412
gtgacagtgg cagtacgcg                                               19

<210> SEQ ID NO 413
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 413
tcagactgaa gttgttaga                                               19

<210> SEQ ID NO 414
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 414
gttggctaga attgggaaa                                               19

<210> SEQ ID NO 415
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 415
gaagaccata gcatccgcc                                               19

<210> SEQ ID NO 416
<211> LENGTH: 19
<212> TYPE: DNA
<213> ORGANISM: Homo sapiens
<220> FEATURE:
<223> OTHER INFORMATION: IGF1R-73

<400> SEQUENCE: 416
gaggtaacag aggtcagca                                               19

<210> SEQ ID NO 417
<211> LENGTH: 19
<212> TYPE: DNA
<213> ORGANISM: Homo sapiens
<220> FEATURE:
<223> OTHER INFORMATION: IGF1R-73 early kinetics gene

<400> SEQUENCE: 417
taggcttgtt gggtcagcg                                                19

<210> SEQ ID NO 418
<211> LENGTH: 19
<212> TYPE: DNA
<213> ORGANISM: Homo sapiens
<220> FEATURE:
<223> OTHER INFORMATION: IGF1R-73 early kinetics gene

<400> SEQUENCE: 418
agcatcttgg acgtcagca                                                19

<210> SEQ ID NO 419
<211> LENGTH: 19
<212> TYPE: DNA
<213> ORGANISM: Homo sapiens
<220> FEATURE:
<223> OTHER INFORMATION: IGF1R-73 early kinetics gene

<400> SEQUENCE: 419
tataaagaag agggcagca                                                19

<210> SEQ ID NO 420
<211> LENGTH: 19
<212> TYPE: DNA
<213> ORGANISM: Homo sapiens
<220> FEATURE:
<223> OTHER INFORMATION: IGF1R-73 early kinetics gene

<400> SEQUENCE: 420
caggtaacag aggacagta                                                19

<210> SEQ ID NO 421
<211> LENGTH: 19
<212> TYPE: DNA
<213> ORGANISM: Homo sapiens
<220> FEATURE:
<223> OTHER INFORMATION: IGF1R-73 early kinetics gene

<400> SEQUENCE: 421
cagaagccag agctcagta                                                19

<210> SEQ ID NO 422
<211> LENGTH: 19
<212> TYPE: DNA
<213> ORGANISM: Homo sapiens
<220> FEATURE:
<223> OTHER INFORMATION: IGF1R-73 early kinetics gene

<400> SEQUENCE: 422
tggccttggc aggtcagca                                                19

<210> SEQ ID NO 423
<211> LENGTH: 19
<212> TYPE: DNA
<213> ORGANISM: Homo sapiens
<220> FEATURE:
<223> OTHER INFORMATION: IGF1R-73 early kinetics gene

<400> SEQUENCE: 423
agaggaggat gggtcagcc                                                19

<210> SEQ ID NO 424
<211> LENGTH: 19
<212> TYPE: DNA
<213> ORGANISM: Homo sapiens
<220> FEATURE:

<223> OTHER INFORMATION: IGF1R-73 early kinetics gene

<400> SEQUENCE: 424
tgagtaacag aggacagct                                                    19

<210> SEQ ID NO 425
<211> LENGTH: 19
<212> TYPE: DNA
<213> ORGANISM: Homo sapiens
<220> FEATURE:
<223> OTHER INFORMATION: IGF1R-73 early kinetics gene

<400> SEQUENCE: 425
gagggaacag aggtcagga                                                    19

<210> SEQ ID NO 426
<211> LENGTH: 19
<212> TYPE: DNA
<213> ORGANISM: Artificial Sequence
<220> FEATURE:
<223> OTHER INFORMATION: IGF1R-73

<400> SEQUENCE: 426
tgctgacctc tgttacctc                                                    19

<210> SEQ ID NO 427
<211> LENGTH: 14
<212> TYPE: DNA
<213> ORGANISM: Homo sapiens
<220> FEATURE:
<223> OTHER INFORMATION: IGF1R-73 12 hour signature gene

<400> SEQUENCE: 427
ataatcatta cctt                                                         14

<210> SEQ ID NO 428
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 428
tactggcatc tgttatcta                                                    19

<210> SEQ ID NO 429
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 429
agctgagctc tgctgtact                                                    19

<210> SEQ ID NO 430
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 430
cccctcactc tgtttcctg                                                    19

<210> SEQ ID NO 431

```
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 431
attaccaacc tgttaccta                                                   19

<210> SEQ ID NO 432
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 432
cgctgacctc accaccgaa                                                   19

<210> SEQ ID NO 433
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 433
gggagagtgc tgtgacctc                                                   19

<210> SEQ ID NO 434
<211> LENGTH: 18
<212> TYPE: DNA
<213> ORGANISM: Homo sapiens
<220> FEATURE:
<223> OTHER INFORMATION: IGF1R-73 12 hour signature gene

<400> SEQUENCE: 434
agcagactct gctacccg                                                    18

<210> SEQ ID NO 435
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 435
tgttaacatc tgtttcagg                                                   19

<210> SEQ ID NO 436
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 436
tgctgccctc atagcagag                                                   19

<210> SEQ ID NO 437
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 437
```
tgggagcttc tgttaactt                                                    19

<210> SEQ ID NO 438
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 438
atggattgaa tgttacctg                                                    19

<210> SEQ ID NO 439
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 439
aactgacagc tgccaccTT                                                    19

<210> SEQ ID NO 440
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 440
gcctgacctc gtcgaattc                                                    19

<210> SEQ ID NO 441
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 441
agctgaactc ttccttgac                                                    19

<210> SEQ ID NO 442
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 442
tttttctcac tgttactga                                                    19

<210> SEQ ID NO 443
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 443
caccgagctc tgtgggaaa                                                    19

<210> SEQ ID NO 444
<211> LENGTH: 19
<212> TYPE: DNA
<213> ORGANISM: Homo sapiens
<220> FEATURE:

<223> OTHER INFORMATION: IGF1R-73 12 hour signature gene

<400> SEQUENCE: 444
accttacctc tgctactgt                                                19

<210> SEQ ID NO 445
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 445
agctgacccg agacttgga                                                19

<210> SEQ ID NO 446
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 446
cgcgttaacc tgttccctt                                                19

<210> SEQ ID NO 447
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 447
ggctaccctc tgatggggt                                                19

<210> SEQ ID NO 448
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 448
aaagaagctc tgtcacaat                                                19

<210> SEQ ID NO 449
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 449
ccagtgcctc tgcttccgg                                                19

<210> SEQ ID NO 450
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 450
cattgacctc tggcacctc                                                19

<210> SEQ ID NO 451

```
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 451
cgaagacccc tttttttgta                                              19

<210> SEQ ID NO 452
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 452
gaatcttaag tgttacagg                                               19

<210> SEQ ID NO 453
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 453
tgctgatgct tccagtaga                                               19

<210> SEQ ID NO 454
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 454
ttcctagttc tgttttctg                                               19

<210> SEQ ID NO 455
<211> LENGTH: 18
<212> TYPE: DNA
<213> ORGANISM: Homo sapiens
<220> FEATURE:
<223> OTHER INFORMATION: IGF1R-73 12 hour signature gene

<400> SEQUENCE: 455
aagagccctt tttacctg                                                18

<210> SEQ ID NO 456
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 456
gaggtaacag aggtcagca                                               19

<210> SEQ ID NO 457
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 457
```

```
gagggaacag aggtcagga                                                19
```

<210> SEQ ID NO 458
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 458

```
tgagtaacag aggacagct                                                19
```

<210> SEQ ID NO 459
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 459

```
cacacagaag aggtcagca                                                19
```

<210> SEQ ID NO 460
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 460

```
ctaaggacag aggtcagat                                                19
```

<210> SEQ ID NO 461
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 461

```
gagttaggag aggtcatca                                                19
```

<210> SEQ ID NO 462
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 462

```
tgaaattaag aggtcagca                                                19
```

<210> SEQ ID NO 463
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 463

```
caactgaatg aggtcagca                                                19
```

<210> SEQ ID NO 464
<211> LENGTH: 19
<212> TYPE: DNA
<213> ORGANISM: Homo sapiens
<220> FEATURE:

```
<223> OTHER INFORMATION: IGF1R-73 12 hour signature gene

<400> SEQUENCE: 464
gaggtgacag agcagattc                                                  19

<210> SEQ ID NO 465
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 465
gaggttactg cagtcagat                                                  19

<210> SEQ ID NO 466
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 466
cgaactatag agggcagca                                                  19

<210> SEQ ID NO 467
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 467
tactaaacag agttcaaaa                                                  19

<210> SEQ ID NO 468
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 468
cagaagccag agctcagta                                                  19

<210> SEQ ID NO 469
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 469
tacaatgtat tggtcagca                                                  19

<210> SEQ ID NO 470
<211> LENGTH: 18
<212> TYPE: DNA
<213> ORGANISM: Homo sapiens
<220> FEATURE:
<223> OTHER INFORMATION: IGF1R-73 12 hour signature gene

<400> SEQUENCE: 470
cagatcacag aggcagcc                                                   18

<210> SEQ ID NO 471
```

```
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 471
tctgggtcaa aggtcaaca                                            19

<210> SEQ ID NO 472
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 472
ggaataacag agagatact                                            19

<210> SEQ ID NO 473
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 473
atttatgaag agatcagcg                                            19

<210> SEQ ID NO 474
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 474
tgatgaacag agatcagac                                            19

<210> SEQ ID NO 475
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 475
agaggaggat gggtcagcc                                            19

<210> SEQ ID NO 476
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 476
ccggtgtcag agggcccgc                                            19

<210> SEQ ID NO 477
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 477
```

-continued

```
atatacacat ttgtcagca                                          19

<210> SEQ ID NO 478
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 478
ataccaacac aggcatccg                                          19

<210> SEQ ID NO 479
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 479
caaggccaag aagccagca                                          19

<210> SEQ ID NO 480
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 480
tacactttaa aagtcagca                                          19

<210> SEQ ID NO 481
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 481
gaggcaacaa gattaaaaa                                          19

<210> SEQ ID NO 482
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 482
gtctggaaag agctcatct                                          19

<210> SEQ ID NO 483
<211> LENGTH: 19
<212> TYPE: DNA
<213> ORGANISM: Homo sapiens
<220> FEATURE:
<223> OTHER INFORMATION: IGF1R-73 12 hour signature gene

<400> SEQUENCE: 483
gagaaaacag tcaaattta                                          19

<210> SEQ ID NO 484
<211> LENGTH: 19
<212> TYPE: DNA
<213> ORGANISM: Homo sapiens
<220> FEATURE:
```

```
<223> OTHER INFORMATION: IGF1R-73 12 hour signature gene

<400> SEQUENCE: 484 ttagttttaaa aggtcaatc                                              19

<210> SEQ ID NO 485
<211> LENGTH: 15
<212> TYPE: DNA
<213> ORGANISM: Homo sapiens
<220> FEATURE:
<223> OTHER INFORMATION: IGF1R-73 12 hour signature gene

<400> SEQUENCE: 485
gagttatcag agggc                                                   15

<210> SEQ ID NO 486
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 486
cctacagaga actgcggtt                                               19

<210> SEQ ID NO 487
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 487
gctacagaga actgcatct                                               19

<210> SEQ ID NO 488
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 488
tttacagaga acttcggta                                               19

<210> SEQ ID NO 489
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 489
tctacagaga actgcagcc                                               19

<210> SEQ ID NO 490
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 490
aggcctcaga actgcgggt                                               19

<210> SEQ ID NO 491
```

-continued

```
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 491
gctacagagg caggccagc                                                 19

<210> SEQ ID NO 492
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 492
aatatttctt cctgcggtt                                                 19

<210> SEQ ID NO 493
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 493
gaagcaggga actttggtg                                                 19

<210> SEQ ID NO 494
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 494
tctacagcca gctggaggc                                                 19

<210> SEQ ID NO 495
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 495
aaccgcagtt ctctgtagg                                                 19

<210> SEQ ID NO 496
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 496
ggccgccgtt ctcctaaga                                                 19

<210> SEQ ID NO 497
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 497
```

```
aaacgaattt cactgtgta                                                19

<210> SEQ ID NO 498
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 498
gtaagcagtc ctgtgagtg                                                19

<210> SEQ ID NO 499
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 499
gacaacagtt tgctgttca                                                19

<210> SEQ ID NO 500
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 500
cctctcggtt ctctaggtc                                                19

<210> SEQ ID NO 501
<211> LENGTH: 18
<212> TYPE: DNA
<213> ORGANISM: Homo sapiens
<220> FEATURE:
<223> OTHER INFORMATION: MAPK14-193 12 hour signature gene

<400> SEQUENCE: 501
gtacgcgttt tctggagc                                                 18

<210> SEQ ID NO 502
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 502
caccgcagac agacccctc                                                19

<210> SEQ ID NO 503
<211> LENGTH: 19
<212> TYPE: DNA
<213> ORGANISM: Homo sapiens
<220> FEATURE:
<223> OTHER INFORMATION: MAPK14-193 12 hour signature gene

<400> SEQUENCE: 503
ccagaaaact ctctgcaga                                                19

<210> SEQ ID NO 504
<211> LENGTH: 19
<212> TYPE: RNA
<213> ORGANISM: Artificial Sequence
<220> FEATURE:
```

Figure 7:
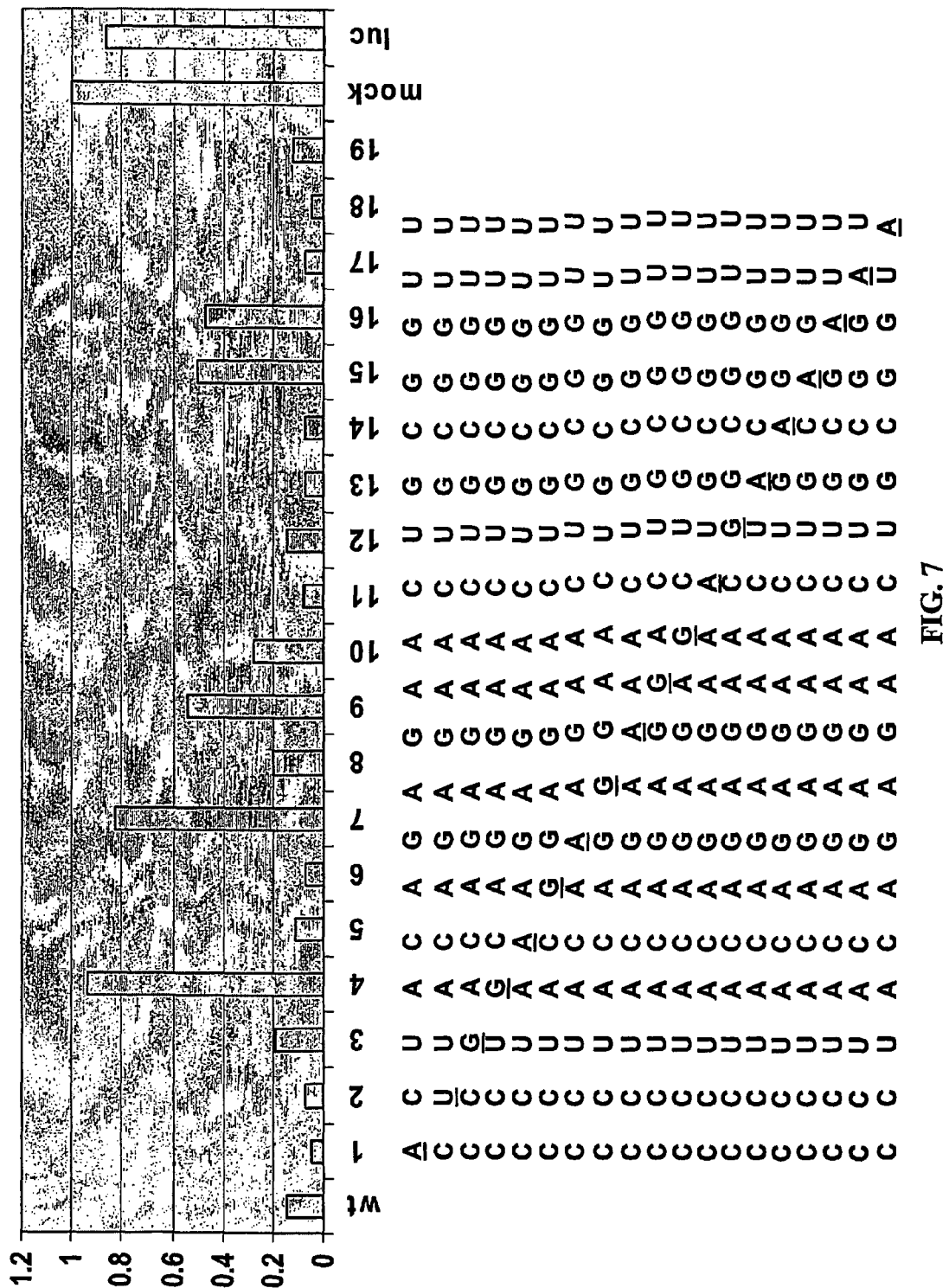
FIG. 7 shows effect of single nucleotide mismatch on knockdown of MAPK14 mRNA by siRNA oligo. The mismatch nucleotide is shown by underscore.

<223> OTHER INFORMATION: knockdown of MAPK14 mRNA by siRNA oligo (Fig.7)

<400> SEQUENCE: 504
acuacagaga acugcgguu                                                19

<210> SEQ ID NO 505
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 505
cuuacagaga acugcgguu                                                19

<210> SEQ ID NO 506
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 506
ccgacagaga acugcgguu                                                19

<210> SEQ ID NO 507
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 507
ccugcagaga acugcgguu                                                19

<210> SEQ ID NO 508
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 508
ccuaaagaga acugcgguu                                                19

<210> SEQ ID NO 509
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 509
ccuacggaga acugcgguu                                                19

<210> SEQ ID NO 510
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 510
ccuacaaaga acugcgguu                                                19

<210> SEQ ID NO 511

-continued

```
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 511
ccuacaggga acugcgguu                                                      19

<210> SEQ ID NO 512
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 512
ccuacagaaa acugcgguu                                                      19

<210> SEQ ID NO 513
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 513
ccuacagagg acugcgguu                                                      19

<210> SEQ ID NO 514
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 514
ccuacagaga gcugcgguu                                                      19

<210> SEQ ID NO 515
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 515
ccuacagaga aaugcgguu                                                      19

<210> SEQ ID NO 516
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 516
ccuacagaga acggcgguu                                                      19

<210> SEQ ID NO 517
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 517
```

```
ccuacagaga acuacgguu                                              19

<210> SEQ ID NO 518
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 518
ccuacagaga acugagguu                                              19

<210> SEQ ID NO 519
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 519
ccuacagaga acugcaguu                                              19

<210> SEQ ID NO 520
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 520
ccuacagaga acugcgauu                                              19

<210> SEQ ID NO 521
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 521
ccuacagaga acugcggau                                              19

<210> SEQ ID NO 522
<211> LENGTH: 19
<212> TYPE: RNA
<213> ORGANISM: Artificial Sequence
<220> FEATURE:
<223> OTHER INFORMATION: knockdown of MAPK14 mRNA by siRNA oligo (Fig.7)

<400> SEQUENCE: 522
ccuacagaga acugcggua                                              19
```